United States Patent [19]

Arnold et al.

[11] Patent Number: 5,713,367
[45] Date of Patent: *Feb. 3, 1998

[54] MEASURING AND ASSESSING CARDIAC ELECTRICAL STABILITY

[75] Inventors: Jeffrey M. Arnold, Wellesley; Paul Albrecht, Bedford; Kevin S. Librett, Boston; Richard J. Cohen, Waban, all of Mass.

[73] Assignee: Cambridge Heart, Inc., Bedford, Mass.

[ * ] Notice: The term of this patent shall not extend beyond the expiration date of Pat. No. 5,570,696.

[21] Appl. No.: 379,375

[22] Filed: Jan. 26, 1995

Related U.S. Application Data

[63] Continuation-in-part of Ser. No. 339,050, Nov. 14, 1994, abandoned, Ser. No. 187,275, Jan. 26, 1994, Pat. No. 5,570,696, and Ser. No. 339,032, Nov. 14, 1994, abandoned.

[51] Int. Cl.⁶ .................................................. A61B 5/0452
[52] U.S. Cl. .................................................. 128/704
[58] Field of Search .......................... 128/696, 702–705, 128/707, 920, 923, 924; 364/413.06

[56] References Cited

U.S. PATENT DOCUMENTS

| | | |
|---|---|---|
| 3,868,947 | 3/1975 | Holsinger . |
| 4,038,536 | 7/1977 | Feintuch ................................. 235/152 |
| 4,082,087 | 4/1978 | Howson . |
| 4,362,165 | 12/1982 | Carmon et al. ........................ 128/640 |
| 4,422,459 | 12/1983 | Simson ................................. 128/702 |
| 4,448,199 | 5/1984 | Schmid ................................. 128/639 |
| 4,458,691 | 7/1984 | Netravali ............................... 128/705 |
| 4,458,692 | 7/1984 | Simson ................................. 128/705 |
| 4,492,235 | 1/1985 | Sitrick ................................... 128/705 |
| 4,583,549 | 4/1986 | Manoli .................................. 128/640 |
| 4,630,204 | 12/1986 | Mortara ................................ 364/417 |
| 4,732,157 | 3/1988 | Kaplan et al. ........................ 128/696 |
| 4,751,931 | 6/1988 | Briller et al. ......................... 128/700 |
| 4,763,660 | 8/1988 | Kroll et al. ........................... 128/640 |
| 4,781,201 | 11/1988 | Wright et al. ........................ 128/671 |
| 4,793,361 | 12/1988 | DeFault ............................... 128/696 |
| 4,802,222 | 1/1989 | Weaver ................................ 381/35 |
| 4,802,491 | 2/1989 | Cohen et al. ........................ 128/702 |
| 4,955,381 | 9/1990 | Way et al. ........................... 128/640 |
| 4,979,110 | 12/1990 | Albrecht et al. ..................... 364/413.03 |

(List continued on next page.)

OTHER PUBLICATIONS

Adam et al., "Estimation of Ventricular Vulnerability to Fibrillation Through T–Wave Time Series Analysis", Computers in Cardiology, pp. 307–310 (1981).

Adam et al., "Ventricular Fibrillation and Fluctuations in the Magnitude of the Repolarization Vector", Computers in Cardiology, pp. 241–244 (1982).

(List continued on next page.)

*Primary Examiner*—Jeffrey R. Jastrzab
*Attorney, Agent, or Firm*—Fish & Richardson P.C.

[57] ABSTRACT

The alternans pattern of cycle-to-cycle variability in physiologic waveforms is assessed by applying transducers to a subject, recording physiologic signals, and analyzing the alternans pattern of variation in waveform morphology. Preferred embodiments include methods and apparatus for measuring and assessing alternans in the presence of physiologic stress, such as exercise, in order to induce or increase the amplitude of the alternans, improvements in signal processing to improve the sensitivity and specificity of the analysis, improvements to provide real-time analysis and feedback to the operator conducting the recording of physiologic signals, reduction in the effect of intercycle interval variability on waveform variability, reduction in the effects of respiration on the alternans measurement, improved means for determining the statistical significance of the alternans measurement, handling of abnormal beats such as atrial and ventricular premature beats, choosing of data epochs over which to perform the alternans measurement, using multiple electrodes to improve the accuracy of the alternans measurement, and combining measurement of alternans with other cardiovascular diagnostic tests to facilitate and improve the combined diagnostic capability.

152 Claims, 41 Drawing Sheets

U.S. PATENT DOCUMENTS

| | | | |
|---|---|---|---|
| 4,991,587 | 2/1991 | Blakeley et al. | 128/653 A |
| 5,010,888 | 4/1991 | Jadvar et al. | 128/696 |
| 5,117,828 | 6/1992 | Metzger et al. | 128/642 |
| 5,148,812 | 9/1992 | Verrier et al. | 128/704 |
| 5,188,116 | 2/1993 | Pommrehn et al. | 128/696 |
| 5,234,404 | 8/1993 | Tuttle et al. | 604/20 |
| 5,237,995 | 8/1993 | Cano | 128/640 |
| 5,259,387 | 11/1993 | dePinto | 128/696 |
| 5,265,617 | 11/1993 | Verrier et al. | 128/704 |
| 5,305,446 | 4/1994 | Leach et al. | 395/425 |
| 5,318,037 | 6/1994 | Evans et al. | 128/696 |
| 5,323,783 | 6/1994 | Henkin et al. | 128/703 |
| 5,341,811 | 8/1994 | Cano | 128/696 |
| 5,348,020 | 9/1994 | Hutson | 128/696 |
| 5,437,285 | 8/1995 | Verrier et al. | 128/702 |
| 5,560,370 | 10/1996 | Verrier et al. | 128/705 |
| 5,570,696 | 11/1996 | Arnold et al. | 128/707 |

OTHER PUBLICATIONS

Adam et al., "Fluctuations in T-Wave Morphology and Susceptibility to Ventricular Fibrillation", J. Electrocardiology 17:209–218 (1984).

Mortara, "Source Consistency Filtering —A New Tool for ECG Noise Reduction", IEEE, pp. 125–128 (1992).

Nearing et al., "Dynamic Tracking of Cardiac Vulnerability by Complex Demodulation of the T Wave", Science 252:437–252 (1991).

Nearing et al., "Personal Computer System for Tracking Cardiac Vulnerability by Complex Demodulation of the T Wave", J. Appl. Physiol. 74:2606–2612 (1993).

Pedretti et al., "Prediction of Late Arrhythmic Events After Acute Myocardial Infarction . . . Sustained Monomorphic Ventricular Tachycardia", Am. J. Cardiol. 71:1131–1141 (1993).

Ring et al., "Exercise–Induced ST Segment Alternans", American Heart Journal 111:1009–1011 (1986).

Ritzenberg et al., "Period Multupling–Evidence for Nonlinear Behavior of the Canine Heart", Nature 307:159–161 (1984).

Rosenbaum et al., "Electrical Alternans and Vulnerability to Ventricular Arrhythmias", New Engl. J. of Medicine 330:235–241 (1994).

Shvartsman et al., "Multichannel Signal Processing Based on Logic Averaging", IEEE Transactions on Biomedical Engineering 7:531–536 (1982).

Smith et al., "Subtle Alternating Electrocardiographic Morphology as an Indicator of Decreased Cardiac Electrical Stability", Computers in Cardiology, pp. 109–112 (1985).

Smith et al., "Electrical Alternans and Cardiac Electrical Instability", Circulation 77:110–121 (1988).

Smith, "The Stochastic Nature of Cardiac Electrical Instability: Theory and Experiment", thesis (1985).

Verrier et al., "Electrophysiologic Basis for T Wave Alternans as an Index of Vulnerability to Ventricular Fibrillation", Cardiovasc. Electrophysiol. 5:445–461 (1994).

Flowers et al., "Surface Recording of His–Purkinje Activity on an Every–beat Basis Without Digital Averaging" Circulation 63, No. 4, Apr., 1981, Division of Cardiology, University of Louisville, pp. 948–952.

Flowers et al., "Analysis of PR Subintervals in Normal Subjects and Early Studies in Patients With Abnormalities of the Conduction System Using Surface His Bundle Recordings", JACC vol. 2, No. 5, Nov. 1983:939–46.

Zimmermann et al., "Beat–tobeat detection of ventricular late potentials with high–resolution electrocardiography", American Heart Journal, Progress in Cardiology, vol. 121, No. 2, part 1, pp. 576–585.

El–Sherif et al., "Beat–to–Beat High–Resolution Electrocardiogram: Technical and Clinical Aspects", Progress in Cardiovascular Diseases, vol. XXXv, No. 6 (May/Jun.) 1993: pp. 407–415.

El–Sharif et al., "Appraisal of a Low Noise Electrocardiogram", J. Am. Coll. Cardiol. 1983:1(2):456–67.

Mortara, "Source Consistency Filtering–Application to Resting ECGs", Journal of Electrocardiol., vol. 25 Supplement, pp. 200–206, 1992.

Mortara, "Source Consistency Filtering —A New Tool for ECG Noise Reduction", In Computers in Cardiology, IEEE, pp. 125–128, Piscataway, NJ, 1991.

Cano et al., "Enhancement of Low–Level ECG Components in Noise with Time–sequenced Adaptive Filtering", Journal of Electrocardiology, vol. 23 Supplement, pp. 176–183, 1990.

Meyer et al., "Electrocardiogram Baseline Noise Extimation and Removal Using Cubic Splines and State–Space Computation Techniques", Computers and Biomedical Research 10, 459–470 (1977).

Evans et al., "Redundancy Reduction for Improved Display and Analysis of Body Surface Potential Maps", Circulation Research, vol. 49, No. 1, pp. 197–203, Jul. 1981.

Uijen et al., "The Number of Signals in Multilead ECGs in Individuals", Journal of Electrocardiology, vol. 26, No. 2, pp. 107–116, 1993.

Damen et al., "The Use of the Singular Value Decomposition in Electrocardiology", Medical & Biological Engineering & Computing, pp. 473–482, Jul., 1982.

Salerno et al., "Ventricular arrhythmias during acute myocardial ischaemia in man . . . ", European Heart Journal (1986) 7 (Supplement A), pp. 63–75.

Zareba et al., "T Wave Alternans," J Am Coll Cardiol (1994), vol. 23, pp. 1541–1546.

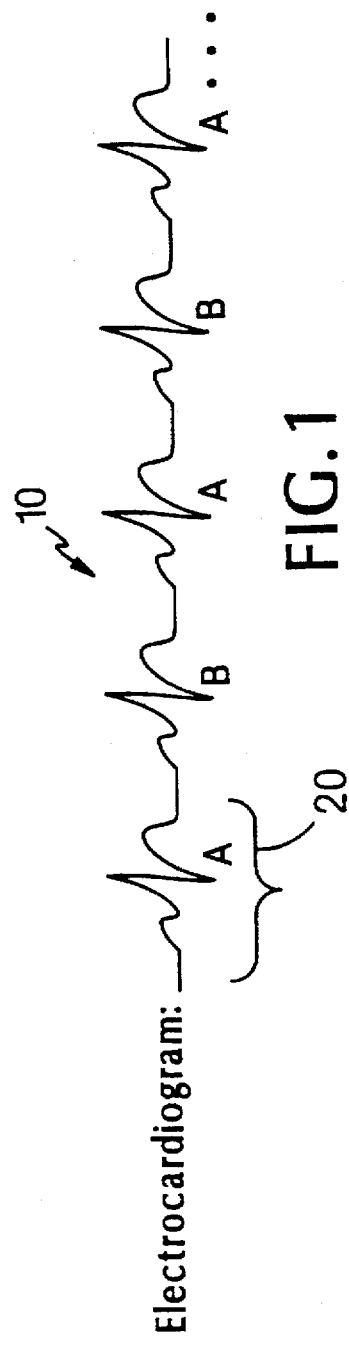
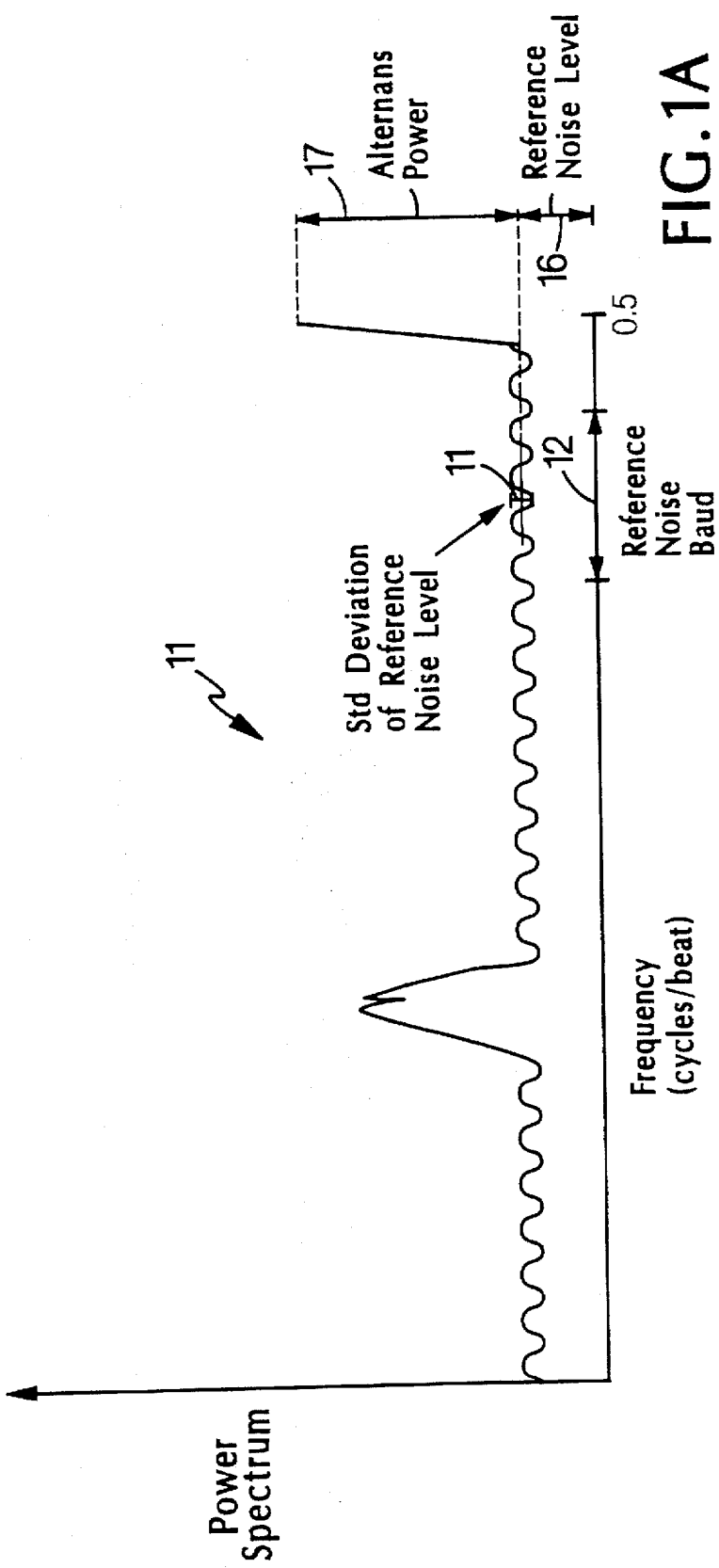

ECG & Noise

Respiration

Impedance

Reduced Noise ECG

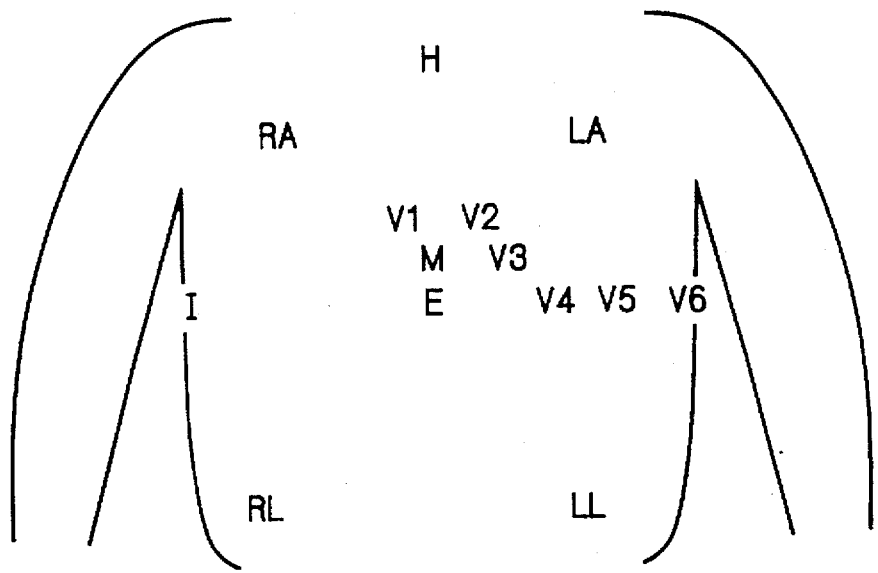

FIG. 22

| Electrode Name | Electrode Location | Type | Available Signals |
|---|---|---|---|
| RL | R. ILLIAC CREST | STANDARD | (DRIVEN GROUND) |
| RA | RIGHT SHOULDER | STANDARD | (REFERENCE) |
| LA | L. SHOULDER | STANDARD | LA |
| LL(F) | L. ILLIAC CREST | MULTIPLE | LLa, LLb, LLc, LLi |
| V1 | V1 | STANDARD | V1 |
| V2 | V2 | STANDARD | V2 |
| V3 | V3 | STANDARD | V3 |
| V4(C) | V4 | MULTIPLE | V4, V4a, V4i |
| V5 | V5 | STANDARD | V5 |
| V6(A) | V6 | MULTIPLE | V6, V6a, V6b, V6i |
| I | R. V6 POSITION | MULTIPLE | I, Ia, Ib, Ii |
| H | BELOW NECK | MULTIPLE | H, Ha, Hi |
| E | BETWEEN A & I | MULTIPLE | E, Ea, Ei |
| M | BACK | MULTIPLE | M, Ma, Mb, Mi |

FIG. 22A $$b(n) = $$

| Row | Signal | Row | Signal |
|-----|--------|-----|--------|
| 1 | LA | 17 | V6i |
| 2 | LL | 18 | I |
| 3 | LLa | 19 | Ia |
| 4 | LLb | 20 | Ib |
| 5 | LLc | 21 | Ii |
| 6 | LLi | 22 | H |
| 7 | V1 | 23 | Ha |
| 8 | V2 | 24 | Hi |
| 9 | V3 | 25 | E |
| 10 | V4 | 26 | Ea |
| 11 | V4a | 27 | Ei |
| 12 | V4i | 28 | M |
| 13 | V5 | 29 | Ma |
| 14 | V6 | 30 | Mb |
| 15 | V6a | 31 | Mi |
| 16 | V6b | 32 | Resp |

$$F_{xyz} = \begin{bmatrix} F_x \\ F_y \\ F_z \end{bmatrix}$$

$$D_{xyz}(n) = F_{xyz}B(n)$$
$$D_{V4}(n) = F_{V4}B(n)$$

FIG. 27

| Col | Signal | $F_x$ | $F_x$ | $F_x$ | $F_x$ |
|---|---|---|---|---|---|
| 1 | LA | | | | |
| 2 | LL | | 0.655 | | |
| 3 | LLa | | | | |
| 4 | LLb | | | | |
| 5 | LLc | | | | |
| 6 | LLi | | | | |
| 7 | V1 | | | | |
| 8 | V2 | | | | |
| 9 | V3 | | | | |
| 10 | V4 | 0.171 | | -0.231 | 1.000 |
| 11 | V4a | | | | |
| 12 | V4i | | | | |
| 13 | V5 | | | | |
| 14 | V6 | 0.610 | | 0.133 | |
| 15 | V6a | | | | |
| 16 | V6b | | | | |
| 17 | V6i | | | | |
| 18 | I | -0.781 | | -0.264 | |
| 19 | Ia | | | | |
| 20 | Ib | | | | |
| 21 | Ii | | | | |
| 22 | H | | -1.00 | | |
| 23 | Ha | | | | |
| 24 | Hi | | | | |
| 25 | E | | | -0.734 | |
| 26 | Ea | | | | |
| 27 | Ei | | | | |
| 28 | M | | 0.345 | 0.736 | |
| 29 | Ma | | | | |
| 30 | Mb | | | | |
| 31 | Mi | | | | |
| 32 | Resp | | | | |

|  | SENSITIVITY | SPECIFICITY | +PV | -PV | RR | p |
|---|---|---|---|---|---|---|
| REST | 50% | 91% | 80% | 71% | 2.8 | 0.14 |
| EX | 80% | 91% | 89% | 84% | 5.3 | 0.005 |
| REST/EX | 100% | 91% | 91% | 100% | >10 | <0.005 |

+PV: POSITIVE PREDICTIVE VALUE;   -PV: NEGATIVE PREDICTIVE VALUE;
RR: RELATIVE RISK;   p: SIGNIFICANCE LEVEL.

FIG. 41

MEASURING AND ASSESSING CARDIAC ELECTRICAL STABILITY

This application is a continuation-in-part of U.S. Ser. No. 08/339,050, filed Nov. 14, 1994, now abandoned entitled "Improved Method and Apparatus for Assessing Cardiac Electrical Stability," and a continuation-in-part of U.S. Ser. No. 08/187,275, filed Jan. 26, 1994, now U.S. Pat. No. 5,570,696 entitled "Improved Method and Apparatus for Assessing Myocardial Electrical Stability," both of which are herein incorporated by reference, and this application is also a continuation-in-part of U.S. Ser. No. 08/339,032, filed Nov. 14, 1994, now abandoned, entitled "Measuring a Physiologic Signal," which is herein incorporated by reference.

BACKGROUND OF THE INVENTION

This invention relates to schemes for measuring and assessing cardiac electrical stability, e.g., by measurement of alternans, a temporal pattern of cycle-to-cycle variability in the morphology of the electrocardiographic (ECG), or by measurement of other physiologic waveforms.

Disturbances of electrical conduction processes in the heart are a major cause of morbidity and mortality. Sudden cardiac death, resulting from disturbances of electrical conduction in the heart, is responsible for approximately 400,000 fatalities per year in the United States alone. The mechanism responsible for the great majority of sudden cardiac deaths is ventricular fibrillation, a disorganized pattern of electrical activity in the ventricles of the heart, which leads to a disorganized pattern of mechanical contraction and results in the cessation of effective pumping action and death. Another disturbance of heart conduction processes, ventricular tachycardia, also reduces the effectiveness of the pumping action of the heart and thereby cause loss of consciousness (syncope) or death. Even in cases where ventricular tachycardia itself does not cause death, ventricular tachycardia can degenerate into ventricular fibrillation, which is lethal.

Effective means are now available to treat patients with electrical instabilities of the heart. For example, the internal programmed cardioverter/defibrillator is effective in preventing sudden cardiac death. This implanted device can terminate ventricular tachycardia and fibrillation by delivering an electric shock to the heart. Also available are antiarrhythmic drugs, which modify the electrical properties of the heart. These drugs may be used to render the heart electrically more stable. However, under certain circumstances, these drugs can also cause the heart to become more susceptible to ventricular tachycardia and fibrillation.

The first step in preventing sudden cardiac death is to identify individuals at risk. A common procedure for identification of risk involves invasive electrophysiologic testing. In this procedure, a catheter with one or more electrodes is advanced through the vasculature until the electrodes are properly positioned in a patient's heart. The electrodes are used to deliver electrical impulses to the heart in a deliberate attempt to initiate ventricular tachycardia. Patients in whom sustained ventricular tachycardia or ventricular fibrillation is induced are deemed to be at enhanced risk of sustaining spontaneous ventricular tachycardia or fibrillation. This invasive procedure is only suitable for stratifying risk in individuals already known to be at high risk. Typically, this procedure is used in individuals who have been successfully resuscitated from an episode of sudden cardiac death. But such invasive electrophysiologic testing would not be preferred for screening large populations of individuals for risk of serious ventricular arrhythmias.

A variety of non-invasive measures have been used to stratify risk, including measurement of the ejection fraction of the heart, measurement of the signal average electrocardiogram, measurement of heart rate variability, and measurement of ambient ventricular ectopic activity on a 24 hour electrocardiogram. These methods generally are not considered sufficiently predictive of risk to justify invasive testing or treatment of an asymptomatic individual. What is desired is a test that is non-invasive and can be reasonably performed in a doctor's office or clinic during routine evaluation of patients for heart disease. It is also desirable that such a test be highly sensitive (i.e., it identifies almost all of the high risk patients) and sufficiently specific (i.e., most positive tests are correct) to justify invasive testing of those patients who test positive.

Recently, it has been determined that the measurement of minute levels of alternans is a powerful technique for assessing susceptibility to ventricular arrhythmias. Alternans is a pattern in which certain portions of the electrocardiographic or other physiologic waveforms, such as the ST segment and the T-wave of an electrocardiogram, alternate in shape in successive beats in an ABABAB... pattern (see FIG. 1). The alternans signal occurs at a fundamental frequency equal to half the heart rate and odd harmonics of the fundamental frequency. There have been, over the years, occasional reports of visible alternans in the electrocardiograms of humans. Alternans have also been associated with some rare disease states and with sudden death. Recently, it has been realized that the detection of microvolt levels of alternans during direct electrical pacing of the heart is generally indicative of cardiac electrical instability and predictive of an individual's susceptibility to ventricular arrhythmias.

What is needed is a scheme to make analysis of alternans a practical clinical tool for the assessment of cardiac electrical stability that can be reasonably used in a doctor's office or clinic.

SUMMARY OF THE INVENTION

In a general aspect, the invention features, a scheme for measuring alternans in at least one physiologic signal representative of activity of the heart of a patient, the physiologic signal including a sequence of substantially repeating physiologic waveforms, the method comprising the steps of: receiving a physiologic signal representative of activity of the heart of the patient whose physiologic condition is altered in such a manner to stress the heart of the patient without applying pacing stimuli to the heart; and digitally processing the physiologic signal to determine a level of alternans in the signal.

Embodiments according to this aspect of the invention may include one or more of the following features. The physiologic condition of the patient is altered in such a manner to stress the heart of the patient without applying pacing stimuli to the heart. Preferably, the physiologic condition of the patient is altered so that the patient's heart rate is above a predetermined rate. The physiologic condition of the patient is preferably altered so that the patient's heart rate is between about 90 and about 150 beats per minute. The physiologic condition of the patient is preferably altered by exercising the patient (e.g., by pedalling a bicycle, walking on a treadmill, or stair stepping). Preferably, a signal is produced for controlling the patient's exercise intensity. Preferably, the signal is produced to achieve a desired heart rate in the patient. Signals re preferably received representative of the patient's rate of exercise.

In certain preferred embodiments, a signal is prodcued for controlling the patient's rate of exercise. The patient's rate of exercise is preferably selected to be between about twenty-eight percent of the patient's heart rate and about forty-three percent of the patient's heart rate or between about fifty-seven percent of the patient's heart rate and about seventy-two percent of the patient's heart rate. The controlling signal is preferably produced to reduce noise that interfere with determining the level of alternans. The controlling signal is preferably produced to reduce noise having a substantially repeating component that repeats at a frequency of about one half the patient's heart rate or at a submultiple thereof. The controlling signal is preferably produced to reduce noise artifacts generated by one or more sources other than the patient's heart. The controlling signal is preferably produced to reduce noise artifacts generated as a result of exercise of the patient. The controlling signal is preferably produced to reduce noise artifacts generated as a result of respiration of the patient. The controlling signal is preferably produced based on a predetermined exercise protocol specifying target exercise rates.

In certain preferred embodiments, the signal is processed to reduce noise that interferes with determining the level of alternans. The determination of a level of alternans is preferably based on portions of the received signal corresponding to periods when the level of exercise falls within a predetermined range. The determination of a level of alternans is preferably based on portions of the received signal corresponding to periods when the patient's respiratory rate is different from the patient's heart rate and is different from sub-multiples of the patient's heart rate. Preferably, portions of the received signal are selected for the determination of alternans based on the presence of abnormal beats. The portions selected for the determination of alternans is based on a comparison of a weighted predetermined level.

Preferably, a signal representative of the determined level of alternans and a signal representative of the determined heart rate are simultaneously produced.

In certain preferred embodiments, interfering variability in the morphology of the substantially repeating waveforms is compensated for in the received signal. The the interfering variability that is compensated may be intercycle interval variability. The interfering variability that is compensated may be variability generated by the patient's respiratory activity.

In certain preferred embodiments the physiologic condition of the patient is altered by administering to the patient a pharmacological agent that stresses the heart of the patient (e.g., a beta-sympathetic agent, a parasympathetic blocking agent, and a vasodilator).

Also, the physiologic condition of the patient may be altered by applying negative body pressure to the lower body of the patient or by selecting the orientation of the patient's body to be different from a supine position. In certain embodiments, the physiologic condition of the patient is altered spontaneously.

In certain embodiments the measurements of alternans is conducted at the same time as other tests (e.g., when determining whether the patient has coronary artery disease by determining physiologic indices of ischemia in the patient).

A. The method of claim 1 or 2 wherein the processing step comprises processing physiologic signals from periods of time before the physiologic condition of the patient is altered.

Physiologic signals may be processed from periods of time after the physiologic condition of the patient is altered.

In certain embodiments, the following steps are performed: obtaining a second signal from the patient; determining a relationship between variability in the first and second received signals; and using the relationship in the determination of a level of alternans.

In another gernal aspect, the invention features a scheme for measuring alternans in at least one physiologic signal representative of activity of the heart of a patient, the physiologic signal including a sequence of substantially repeating physiologic waveforms, the method comprising the steps of: receiving a physiologic signal representative of activity of the heart of the patient; digitally processing the physiologic signal to determine a level of alternans in the signal; and producing a signal for controlling the physiologic condition of the patient in a manner such that the effects of interfering noise sources is reduced.

In yet another general aspect, the invention features a scheme for measuring alternans in at least one physiologic signal representative of activity of the heart of a patient, the physiologic signal including a sequence of substantially repeating physiologic waveforms, the method comprising the steps of: receiving a physiologic signal representative of activity of the heart of the patient after the physiologic condition of the patient has been altered in such a manner to stress the heart of the patient to achieve a heart rate above a predetermined rate; digitally processing the physiologic signal to determine a level of alternans in the signal.

In another aspect, the invention features a scheme for measuring alternans in at least one physiologic signal representative of activity of the heart of a patient, the physiologic signal including a sequence of substantially repeating physiologic waveforms, the method comprising the steps of: receiving a physiologic signal representative of activity of the heart of the patient; and digitally processing the physiologic signal to determine a level of alternans in the signal, wherein the processing step comprises processing the signal to reduce the effect of noise signals having a frequency at about half of the patient's heart rate or at about a submultiple half of the patient's heart rate.

In another general aspect, the invention features a scheme for measuring alternans in at least one physiologic signal representative of activity of the heart of a patient, the physiologic signal including a sequence of substantially repeating physiologic waveforms, the method comprising the steps of: receiving a physiologic signal representative of activity of the heart of the patient; digitally processing the physiologic signal to determine a level of alternans in the signal, wherein the processing step comprises characterizing one or more portions of the received signal based on one or more preselected criteria and using the characterization of the portions to determine a level of alternans in the signal.

In another general aspect, the invention features a real-time scheme for measuring alternans in at least one physiologic signal representative of activity of the heart of a patient, the physiologic signal including a sequence of substantially repeating physiologic waveforms, the method comprising the steps of: receiving a physiologic signal representative of activity of the heart of the patient; digitally processing the physiologic signal to determine a level of alternans in the signal; and simultaneously with the processing step, providing an output representative of the level of alternans.

In another aspect, the invention features a real-time scheme for measuring alternans in at least one physiologic signal representative of activity of the heart of a patient, the physiologic signal including a sequence of substantially repeating physiologic waveforms, the method comprising the steps of: receiving a physiologic signal representative of activity of the heart of the patient; digitally processing the received physiologic signal to determine a level of alternans and to determine a level of noise; and using the determined level of noise to assess the condition of the patient's heart to determine with a predetermined level of statistical certainty whether the alternans level is above an upper threshold or is below a lower threshold.

In another specific aspect, the invetion features an apparatus for measuring an alternans pattern of cycle-to-cycle morphology variations in a sequence of substantially repeating physiologic waveforms in at least one signal measured from a patient, the apparatus comprising: one or more transducers for respectively measuring one or more signals from a patient, at least one of said one or more transducers being positioned on the patient to measure a signal comprising a sequence of substantially repeating waveforms representative of one or more signals from the heart of the patient; a processor adapted to obtain, from said one or more measured signals, a measure of the level of alternans in said at least one representative signal for assessing the condition of the patient's heart; and a stressing device adapted to interact with the patient for altering the physiologic condition of the patient to controllably stress the heart of the patient to enhance the measurement of alternans.

In another aspect, the invention features an apparatus for measuring an alternans pattern of cycle-to-cycle morphology variations in a sequence of substantially repeating physiologic waveforms in at least one signal measured from a patient, said apparatus comprising: one or more transducers for respectively measuring one or more signals from a patient, at least one of said one or more transducers being coupled to the patient to measure a signal comprising a sequence of substantially repeating waveforms representative of one or more signals from the heart of the patient, said one or more transducers being adapted to remain coupled to the patient for a period in excess of about one hour; a recorder coupled to said one or more transducers and adapted to store signals measured by said one or more transducers for a period in excess of one hour; and a processor adapted to characterize portions of said measured signals corresponding to one or more periods according to one or more preselected criteria, and further adapted to obtain, from said one or more stored signals corresponding to said one or more selected periods, a measure of the level of alternans in said at least one representative signal for assessing the condition of the patient's heart.

In yet another aspect, the invention features an apparatus for measuring an alternans pattern of cycle-to-cycle morphology variations in a sequence of substantially repeating physiologic waveforms in at least one signal measured from a patient, said apparatus comprising: one or more transducers for respectively measuring one or more signals from a patient, at least one of said one or more transducers being coupled to the patient to measure a signal comprising a sequence of substantially repeating waveforms representative of one or more signals from the heart of the patient; a heart rate monitor coupled to at least one of said one or more transducers and adapted to measure the heart rate of the patient from signals measured by said at least one transducer; and a processor adapted to obtain, from said one or more measured signals and from said measured heart rate, a measure of the level of alternans in said at least one representative signal for assessing the condition of the patient's heart.

In another aspect, the invention features a scheme for measuring a pattern of cycle-to-cycle morphology variations in a sequence of substantially repeating physiologic waveforms in at least one signal measured from a patient, said method comprising the steps of: measuring one or more signals from a patient, at least one of said one or more signals comprising a sequence of substantially repeating waveforms representative of one or more signals from the heart of the patient; processing said one or measured signals to obtain a measure of the level of alternans in said one or more measured signals for assessing the condition of a patient's heart; and enhancing the measurement of the pattern of cycle-to-cycle morphology variations by reducing the effect of variability in the interval between adjacent waveforms in said at least one representative signal.

In another aspect, the invention features a scheme for measuring a pattern of cycle-to-cycle morphology variations in a sequence of substantially repeating physiologic waveforms in at least one signal measured from a patient, said method comprising the steps of: measuring one or more signals from a patient, at least one of said one or more signals comprising a sequence of substantially repeating waveforms representative of one or more signals from the heart of the patient; processing said one or measured signals to obtain a measure of the level of alternans in said one or more measured signals for assessing the condition of a patient's heart; and compensating for interfering variability in the morphology of the substantially repeating waveforms in the received signal.

In another aspect, the invention features a scheme for measuring an alternans pattern of cycle-to-cycle morphology variations in a sequence of substantially repeating waveforms in at least one signal measured from a patient, comprising the steps of: measuring one or more signals from a patient, at least one of said one or more signals comprising a sequence of substantially repeating waveforms representative of one or more signals from the heart of the patient; processing the one or more signals to compute a measure of alternans in the repeating waveforms; additionally processing the one or more signals to produce one or more of the following additional diagnostic tests: a multi-lead electrocardiogram, a signal averaged electrocardiogram, a test for the presence of coronary artery disease, an analysis of QRS complex variability, or physiologic system identification.

In another aspect, the invetion features an apparatus for measuring an alternans pattern of cycle-to-cycle morphology variations in a sequence of substantially repeating waveforms in at least one signal measured from a patient, said apparatus comprising: one or more transducers for respectively measuring one or more signals from a patient, at least one of said one or more transducers being coupled to the patient to measure at least one signal comprising a sequence of substantially repeating waveforms representative of one or more signals form the heart of the patient; a processor capable of processing the signals to produce one or more of the following additional diagnostic tests:a multi-lead electrocardiogram, a signal averaged electrocardiogram, a test for the presence of coronary artery disease, an analysis of QRS variability, or physiologic system identification.

Schemes embodying combination of the above features are also contemplated. Such combinations offer complementary improvements for the measurement of alternans.

Other features and advantages of the invention will become apparent from the following description and from the claims.

DESCRIPTION OF THE DRAWINGS

FIG. 1 is a diagrammatic plot of a typical ECG. FIG. 1A is a diagrammatic power spectrum of the ECG of FIG. 1.

FIG. 22 shows the placement location of electrodes on the body of a patient. FIG. 22A defines the location of the electrodes, shown in FIG. 7, their type, and defines the input signals that are recorded from these electrodes.

FIG. 27 is a table defining coefficients for combining the input signals to create the output signals.

FIG. 41 is a table of results from a clinical study testing the invention's ability to identify ventricular vulnerability.

DESCRIPTION OF THE PREFERRED EMBODIMENTS

Figure 2:
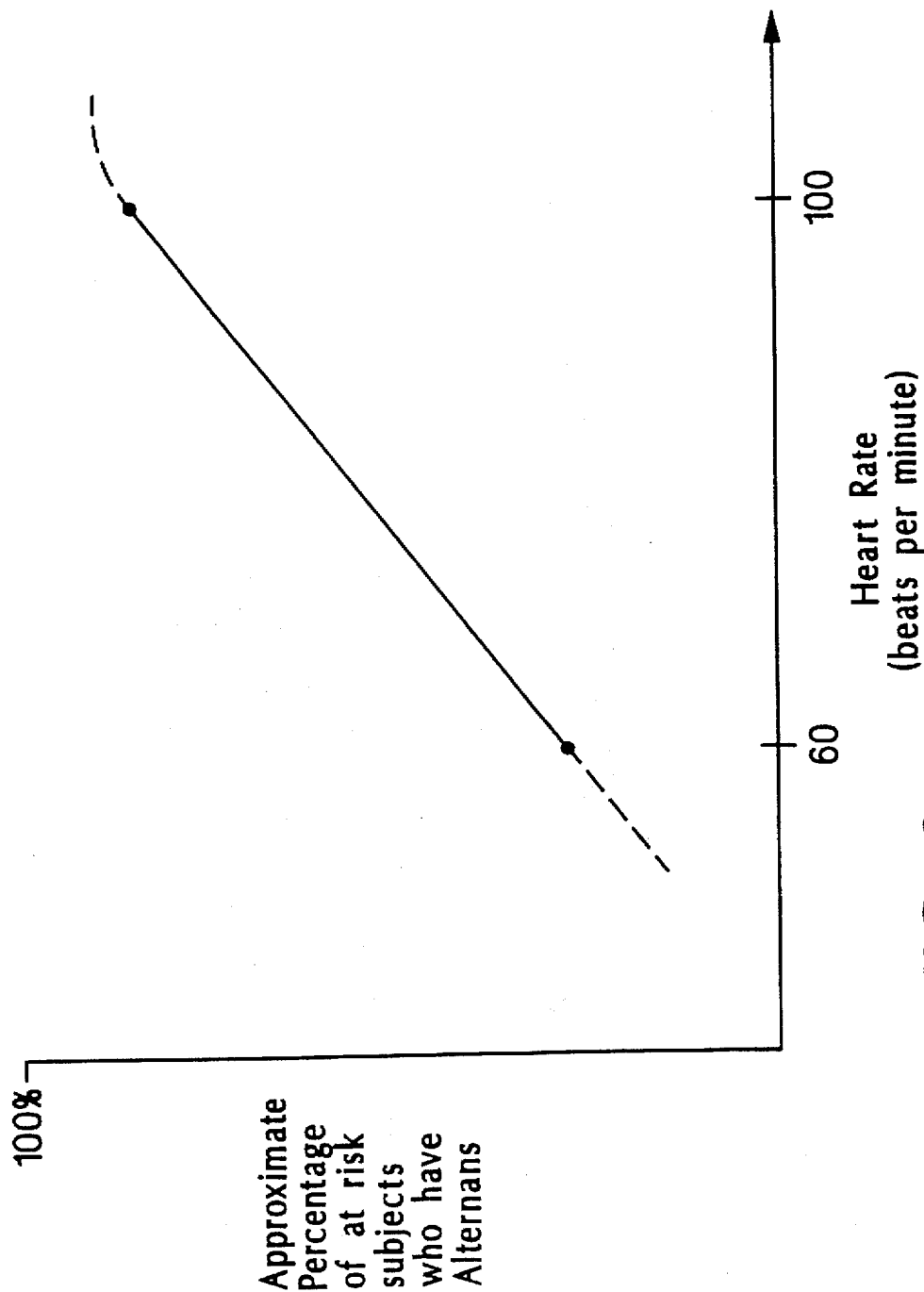
FIG. 2 is a plot of the approximate number of patients at risk for cardiac instability in whom alternans is observed plotted as a function of heart rate.

Referring to FIGS. 1 and 1A, a typical ECG signal 10 has a power spectrum 11 characterized by a reference band 12 that has a standard deviation 14 and a reference noise level 16. The alternans level 18 is measured from the energy level at the alternans frequency of one half the heart rate. As described in U.S. Pat. No. 4,802,491, which is incorporated herein by reference, the power spectrum 11 is determined by sampling a sequence of substantially repeating electrocardiographic waveforms 20, in this case T waves, and processing this sampled data. The alternans is estimated from the amplitude of the power spectrum at the alternans frequency (0.5 cycles per beat), as well as the mean and standard deviation of a reference noise band. The amplitude of the power spectrum at the alternans frequency is compared with the mean and standard deviation of the reference noise band to determine if alternans is present at a statistically significant level.

An alternans pattern of variability in an electrocardiogram with an amplitude even in the microvolt range is clinically significant (in contrast, an ECG typically has a peak amplitude in the millivolt range). An alternans pattern of variability is usually too small to be detected by visual inspection of an electrocardiogram. Alternans is also difficult to measure because it must be detected and quantified in the presence of other temporal patterns of beat-to-beat variability in the electrocardiographic waveform, which are usually larger in magnitude than the level of alternans. For example, skeletal muscle activity, electrode and cable motion, ambient electromagnetic activity in the room, and electrocardiograph amplifiers all introduce noise which cause subtle beat-to-beat variability in the shapes of electrocardiographic waveforms.

I. Measurement of Alternans in Association with Application of Physiologic Stress Data we have collected in patients susceptible to ventricular arrhythmias indicate that the incidence of alternans increases with heart rate. As illustrated in FIG. 2, as the heart rate increases from sixty to approximately ninety-five beats per minutes, the incidence of alternans increases in susceptible patients from under forty percent to approximately eighty percent. Based on this data, we believe that a sensitive clinical test to measure susceptibility to ventricular arrhythmias using currently known techniques requires that the heart rate be elevated to around this level.

As shown in FIG. 2, physiologic waveform variability may depend greatly on the repetition rate of the waveform. In the case of an electrocardiographic waveform, the magnitude of alternans in individual animals increases with heart rate when the heart is paced by electrodes placed within the heart. However, recent data we have collected from a population of subjects susceptible to ventricular arrhythmias indicates that the incidence of alternans also increases with heart rate. That is, at normal heart rates many or most patients who are susceptible to ventricular tachycardia do not appear to demonstrate alternans in their electrocardiogram even though they will when electrically paced at higher heart rates. By about 100 beats per minute (BPM) almost all patients susceptible to ventricular arrhythmias will demonstrate alternans. We believe that a sensitive clinical test to measure susceptibility to ventricular arrhythmias using currently known techniques requires that the heart rate be elevated to around this level.

We have realized that the measurement of alternans can be enhanced by altering the physiologic condition of the patient to controllably stress the patient's heart (i.e., by application of one or more selected physiologic stress techniques, e.g., as described below). Data we have collected indicates that application of a physiologic stress may increase the incidence and level of alternans in a population of subjects at risk for ventricular arrhythmias in a manner which is independent of the effect of the physiologic stress on the heart rate. In the clinical study presented below, we found that alternans measured during an exercise protocol designed to raise the heart rate to 100 beats per minute was a more accurate predictor of a patient's susceptibility to ventricular tachycardia for ventricular fibrillation than alternans measured during atrial pacing at 100 beats per minute. This indicates that the physiologic stress of exercise may have an effect independent of the effect of exercise on heart rate on inducing and/or raising the level of alternans. In addition, fewer than fifty percent of patients who had measurable levels of alternans during exercise were found to have measurable levels of alternans at rest. Thus, measurement of alternans in the presence of a physiologic stress appears to make the alternans measurement a more sensitive test for cardiac electrical instability independent of the change in heart rate resulting from the physiologic stress.

Altering the physiologic condition of the patient (e.g., by exercise, by administration of a suitable pharmacologic agent, by applying negative body pressure, or by changing the orientation of the patient's body) is easily achieved in a doctor's office or clinic. Also, using such techniques to control the application of physiologic stress enables a patient's heart rate, or elevation in heart rate, to be used to assess the general level of the physiological stress.

Altering the Physical Condition of a Patient

Figure 3:
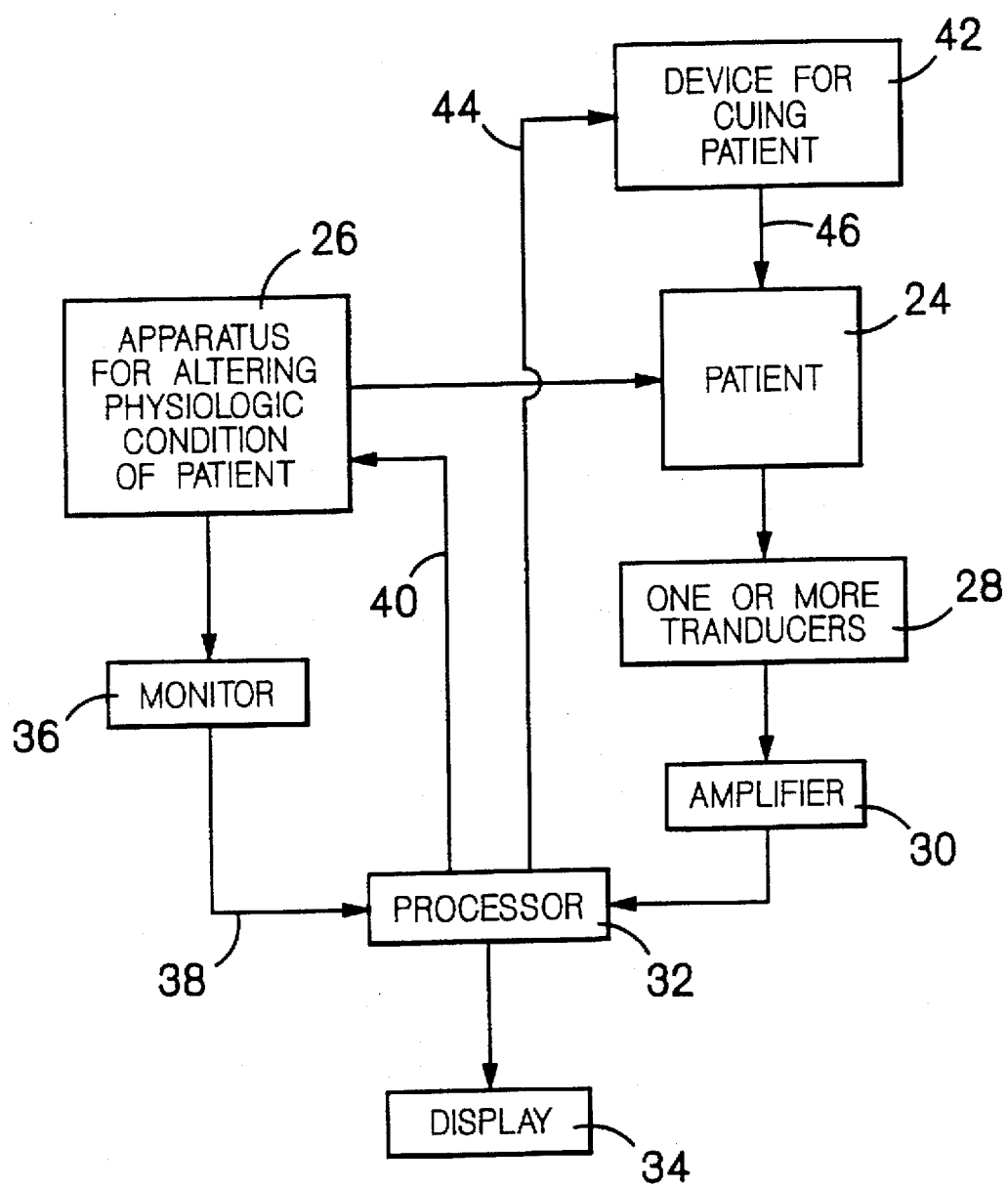
FIG. 3 is a schematic block diagram of a patient, an apparatus for altering the physical condition of the patient and an apparatus for measuring physiologic signals from the patient.

Referring to FIG. 3, a generalized scheme for measuring alternans during alteration of the physical condition of a patient 24 includes an apparatus 26 for altering the physical condition of the patient (e.g., as described below). One or more transducers 28 (e.g., ECG electrodes) are positioned on the surface of the patient to measure signals from the patient, at least one of which being representative of one or more signals from the patient's heart. The measured signals are amplified by an amplifier 30 and are subsequently received by a processor 32. The processor is adapted (e.g., in hardware or software) to obtain a measure of the level of alternans in at least one of the measured signals. This measure is displayed on a display 34 (e.g., a TV monitor or a chart recorder) for viewing by an operator.

A monitor 36 is included to provide to the processor signals 38 representative of the status of apparatus 26 (e.g., the pedal rate if the apparatus is a bicycle). The processor, based on status signals 38, adaptively controls the alteration of the physical condition of the patient by passing control signals to apparatus 26 over feedback loop 40. The processor may also selectively pass signals to a device 42 for cuing the patient over control path 44. Cuing device 42 delivers signals 46 to the patient specifying instructions for voluntary alterations of the patient's physical condition.

A. Exercise

In one embodiment, physiologic stress is non-invasively applied by having the subject exercise, for example, by pedaling on an upright bicycle, pedaling on a supine bicycle, walking on a treadmill, or stepping on stairs. Such method might include a means of measuring heart rate and using such measurement to adjust the level of exercise so that the heart rate is maintained within a desired range. In preferred embodiments of the invention, the patient exercises at a rate controlled so that his heart rate is greater than about 90 BPM, preferably greater than about 100 BPM, and more preferably between about 100 and about 150 BPM.

In one preferred embodiment of the invention, the method and apparatus of this invention is combined with the method and apparatus used to conduct physiologic stress tests for other purposes, for example exercise stress tests used to detect the presence of coronary artery disease. Apparatus for the latter usually includes a treadmill or bicycle or other equipment for performing controlled exercise and equipment for recording electrocardiographic signals. This combination of apparatus is desirable furthermore because for many patients in whom one would want to assess physiologic waveform variability, one would also wish to perform an exercise stress test to detect the presence of coronary artery disease.

The level of exercise may be altered to adjust the subject's heart rate in a variety of ways. For example, when a subject is exercising on a bicycle the resistance of the bicycle to pedaling may be altered and/or the subject may be instructed to alter the pedaling speed. For example, when a treadmill is being used the speed of the treadmill (or equivalently the patient's step rate) may be altered, or the incline of the treadmill may be altered. For example, when the physiologic stress is stair stepping the level of exercise may be altered by adjusting the step rate and/or the incline of the treadmill.

B. Pharmacologic Agent

In another embodiment, physiologic stress is non-invasively applied by administration of pharmacological agents known to simulate physiologic stress. Examples of drugs that are used include: parasympathetic blocking agents, such as atropine and glycopyrrulate; a beta-sympathetic agonist, such as isoproterenol, dopamine, and dobutamine; and a vasodilator, such as nitroprusside. We have found that beta-sympathetic agonists may be desired agents because beta-sympathetic stimulation enhances alternans independent of their effect on heart rate. In each case, the method of the invention may involve measuring heart rate and adjusting the dosage of the drug to maintain heart rate in the desired range. For example, this may be accomplished by intravenously infusing a solution of the drug and then progressively increasing the infusion rate until the heart rate achieves a desired level, e.g., greater than 90 BPM, preferably greater than 100 BPM, and more preferably between 100 and 150 BPM. Alternatively, the data could be collected during a standard pharmacological stress test conducted for other diagnostic purposes, e.g., a stress test used to detect coronary artery disease. Preferably, the only data segments analyzed are those in which the target heart achieves a desired level.

Example: Isoproternol Protocol

A presently preferred embodiment for measuring alternans in a patient by administering isoproterenol has the following protocol. Assure that standard ECG electrodes and X, Y, Z electrodes are properly positioned on the patient. In the event of adverse reaction to isoproterenol, have on hand the beta-sympathetic drug propranolol hydrochloride for intravenous administration in 1 mg doses to reverse the effects of isoproterenol on the cardiovascular and other systems. Via a peripheral intravenous line, administer isoproterenol at a rate of 0.5 micrograms per minute and gradually increase the infusion rate until the heart rate exceeds 100 beat per minute (range 100–110 beats per minute). Then adjust infusion rate to maintain heart rate in desired range. Monitor patient for evidence of arrhythmias on the electrocardiogram and/or the development of ischemia manifested by chest pain or significant ST segment shifts on the electrocardiogram. Continue recording ECG with Alt-ECG device until a sufficient amount of data has been collected, e.g., as determined by one or more of the techniques described below.

Example: Atropine Protocol

A presently preferred embodiment for measuring alternans in a patient by administering atropine has the following protocol. Place standard ECG electrodes and X, Y, Z electrodes on the patient. In the event of adverse reaction to atropine, have on hand physostigmine salicylate for intravenous administration in a dose of 0.5 to 1.0 mg to reverse the central and peripheral anticholinergic effects of atropine. Also have on hand physostigmine eye drops to reverse any ocular effects of the atropine. Via a peripheral intravenous line, administer an initial does of atropine 0.8 mg IV. Increase the dosage by 0.2 mg to 0.4 increments until the heart rate exceeds 100 bpm (range 100–110 bpm), or until a total cumulative does of 2.0 mg of atropine has been administered. Continue recording ECG until a sufficient amount of data has been collected, e.g., as determined by one or more of the techniques described below.

C. Negative Body Pressure

In certain situations, physiologic stress is non-invasively applied by means of applying lower body negative pressure (here negative pressure is taken to mean negative with respect to ambient atmospheric pressure). In one presently preferred embodiment, the lower extremities are placed in a negative pressure chamber, the heart rate is measured by a heart rate monitor, and the level of negative pressure is adjusted to maintain heart rate in the desired range.

D. Change of Body Orientation

In certain other situations, physiologic stress is non-invasively applied by means of change of body position, for example, by recording data while the patient is tilted on a tilt table or by recording data when the patient assumes a sitting or standing position. Physiologic signal recording in patients is most commonly obtained with the patient in the supine position. Substantial physiologic stress can be achieved by changing the orientation of the patient's body in the earth's gravitational field. This is preferably achieved by placing the patient on a tilt table and tilting the patient. Significant stress can also be achieved by having the patient assume a standing position, or even the sitting position—particularly in hemodynamically compromised patients. In this preferred embodiment, the patient's body position is changed to induce physiologic stress, physiologic signals are recorded while the patient is subjected to the stress, and the physiologic signals are analyzed for the presence of alternans.

II. Reducing Interfering Noise Signals:

A. Exercise Artifacts

One problem associated with the measurement of alternans associated with the application of a physiologic stress is that the physiologic stress itself can induce noise that interferes with the alternans measurement. For example, exercise may induce a rhythmic artifact at the alternans frequency (half of the heart rate). It is therefore desirable to choose modes of physiologic stress that induce as little rhythmic artifact as is practical. For example, one would wish to limit upper body movement to reduce motion artifact induced in the chest leads. Thus, bicycle exercise would be expected to be preferred over arm motion exercise.

In a preferred embodiment, the parameters of the physiologic stress are adjusted to minimize the interference with the alternans measurement. In certain preferred embodiments, where exercise is used as the physiologic stress, exercise parameters are adjusted in such a way to minimize the effect of rhythmic noise which interferes with the alternans measurement.

Example: Bicycle Exercise

During bicycle exercise, we have realized that the recorded electrocardiograms contains motion artifact at frequencies corresponding to the pedal rate and its harmonics. The pedal rate is set so that frequency content of the pedaling signal and the frequency content of the alternans signal are separated as much as is practical, consistent with achieving a target heart rate and comfortable pedal rates. The separation in the frequency domain between the pedaling signal's fundamental and second harmonic from the alternans signal's fundamental and third harmonic is improved by setting the pedal rate (the pedal rate and its second harmonic both lie between half the heart rate and three halves of the heart rate) at one-third or two-thirds of the heart rate. This is obtained by solving the equation:

$$PR - HR/2 = 3 \cdot HR/2 - 2 \cdot PR$$

where HR is the heart rate and PR is the pedal rate.

A reference frequency noise band is used to estimate the noise in the alternans measurement. In one presently preferred embodiment, this noise band is calculated, as described in Smith et al. ("Electrical alternans and cardiac electrical instability" by J. M. Smith et al., Circulation, 77, 1988, 110–121; which is herein incorporated by reference). According to the technique described in Smith et al., the noise band corresponds to the frequency band of 0.43 HR to 0.46 HR in the power spectrum. To minimize the overlap between the frequency content of the pedaling signal and the reference noise band, after taking into account the aliasing about the Nyquist frequency of HR/2, this noise band corresponds to the unaliased frequency bands of:

0.43 HR+nHR to 0.46 HR+nHR, and 0.54 HR+nHR to 0.57 HR+nHR where n is the set of non-negative integers. So if PR and 2 PR lie between the upper edge of the noise band at 0.57 HR and the lower edge of the noise band located at 1.43 HR, then 0.57 HR<PR<0.715 HR with PR optimally being set at 0.6425 HR. If PR lies between 0.57 HR and 1.43 HR but 2 PR lies between the band edges of 1.57 HR and 2.43 HR this implies 0.785 HR<PR<1.215 HR with PR optimally being equal to the HR. If PR is less than the band edge at 0.43 HR and 2 PR lies above the band edge at 0.57 HR this implies that 0.285 HR<PR>0.43 HR with an optimal frequency of 0.3575 HR.

Figure 4:
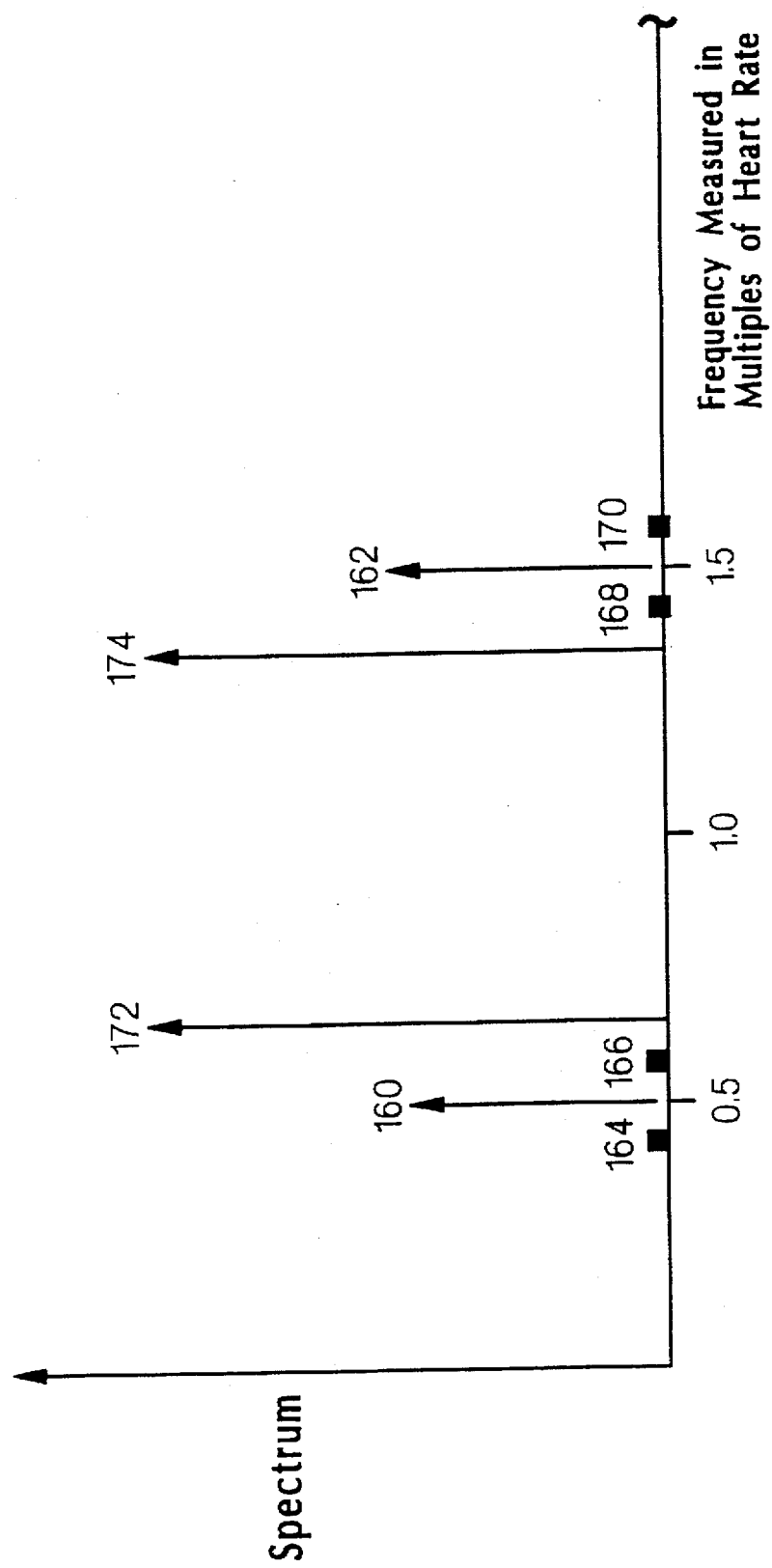
FIG. 4 is a plot of the frequency locations of alternans, reference noise bands, and pedaling motion artifacts.

Referring to FIG. 4, the frequency content of the alternans signal fundamental 160, the third harmonic of the alternans signal 162, the reference noise bands 164, 166, 168, 170, the first harmonic of a sample pedal rate 172 and the second harmonic of this sample pedal rate 174. Using such considerations, protocols may be established defining target pedaling rates for target heart rates:

| Target Heart Rate (beats per minute) | Target Pedal Rate (revolutions per minute) |
| --- | --- |
| 105–115 | 65–75 |
| 100–110 | 63–72 |
| 105–115 | 33–45 |
| 100–110 | 31–43 |

The subject is instructed to maintain the pedal rate in the desired range (the apparatus may measure the actual pedaling rate and display to the subject the actual pedaling rate and the target), and the resistance to pedaling is adjusted automatically by the apparatus or manually by the operator to maintain the heart rate within the desired range. The protocol in which the target pedaling rate is controlled near one-third of the heart rate is found to be particularly convenient and comfortable for many patients. In certain situations, the operator may choose a different protocol, depending on the ability of the patient.

In one preferred embodiment the pedal rate is controlled by the use of a metronome to cue the patient to pedal at the appropriate rate. For example, the patient wears ear phones that provide alternating audio tones cuing the patient to pedal alternately with the right and left foot. Alternatively, the patient is cued to pedal with the right and left foot by using alternating visual prompts.

In certain preferred embodiments, the apparatus has a tachometer to measure pedal rate as well as heart rate and measured data that does not fall within the specified limits of heart rate and pedal rate are ignored. Means of measuring pedal rate includes an electronic interface with a revolution rate meter on the bicycle, an accelerometer on the patient's leg, and means to analyze the electrocardiogram signal noise induced by pedaling (for example, by analyzing the variability in the PQ segment of the ECG which normally reflects no cardiac electrical activity).

Figure 5:
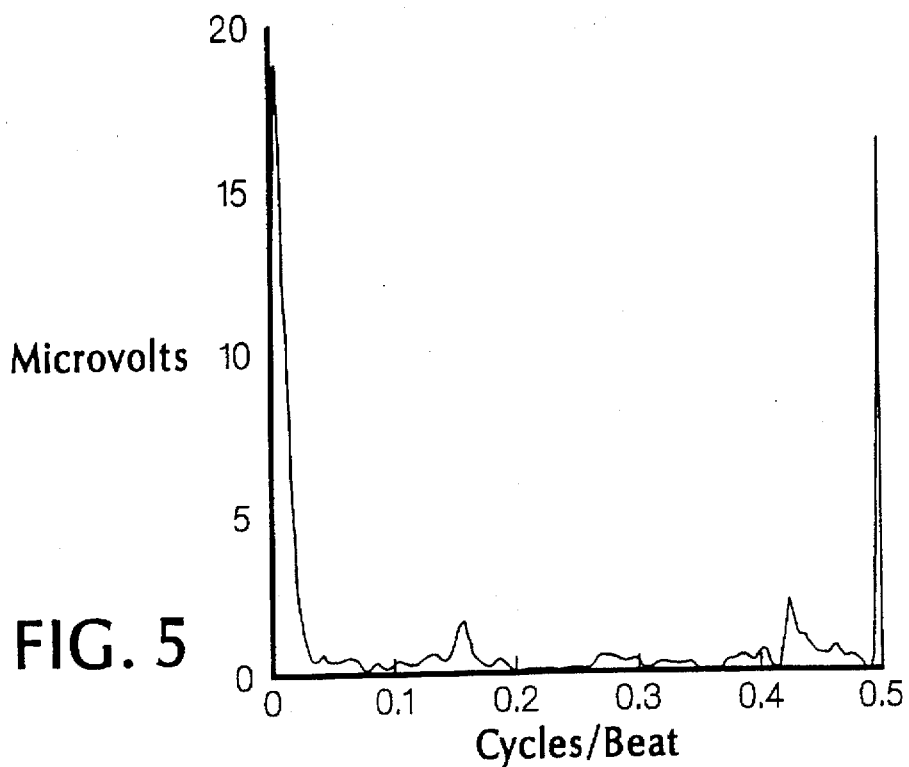
FIG. 5 is a plot of a power spectrum of data obtained during atrial pacing of the heart.
Figure 6:
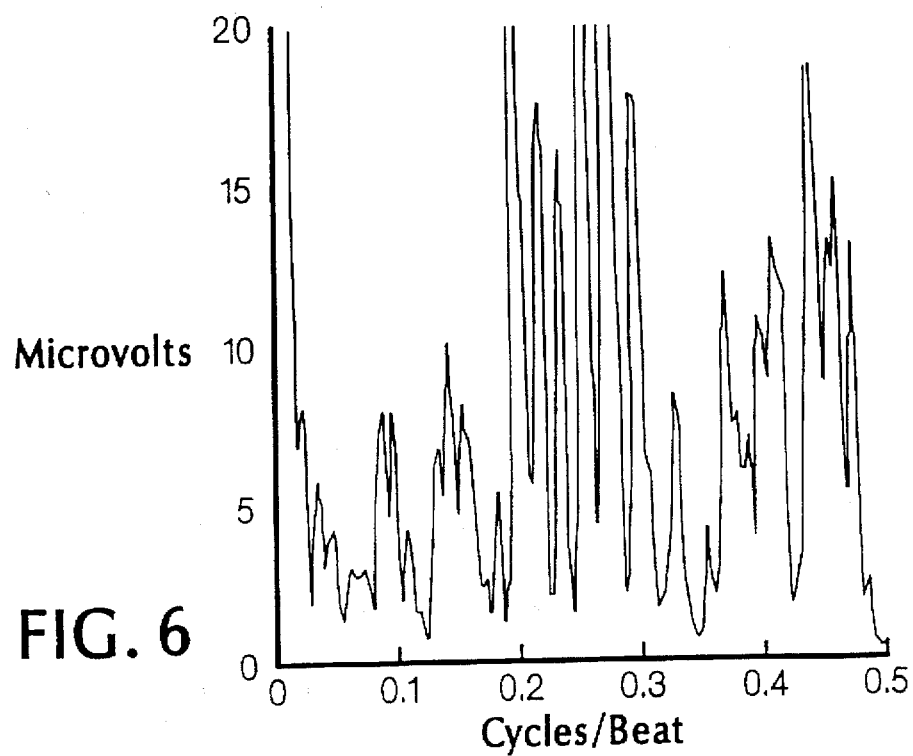
FIG. 6 is a plot of a power spectrum of data obtained during uncontrolled exercise.
Figure 7:
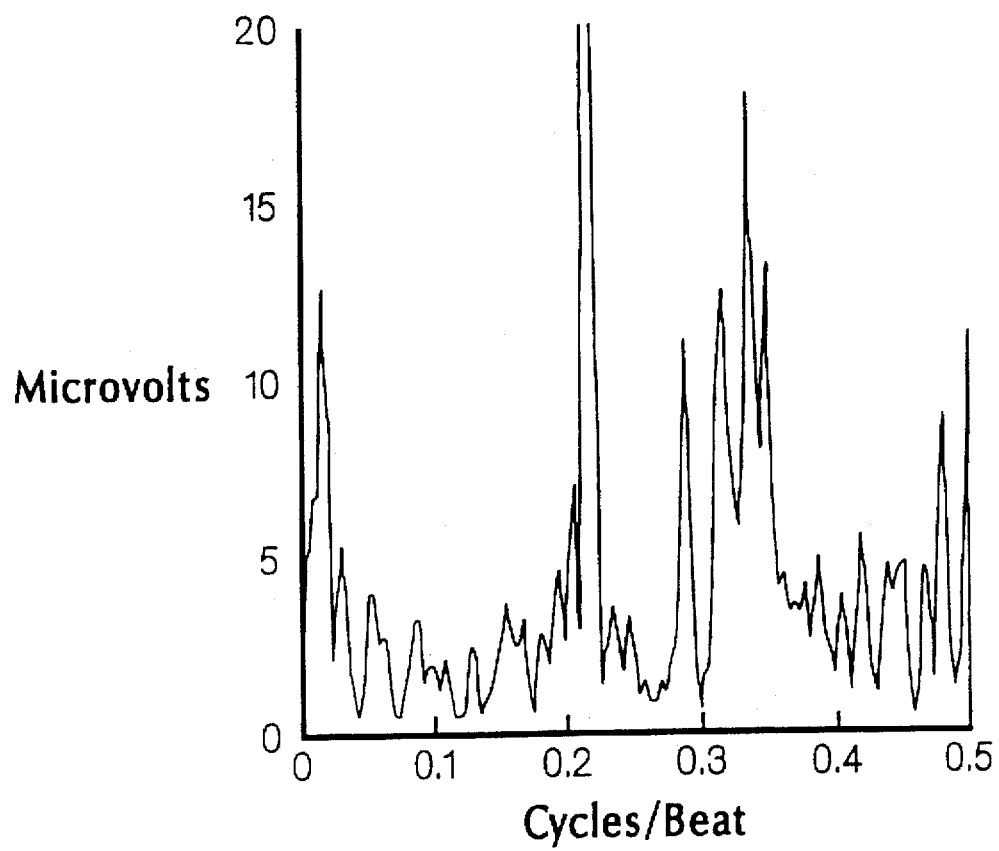
FIG. 7 is plot of a power spectrum of data obtained during bicycle exercise controlled according to the invention.

The importance of controlling pedal rate is illustrated in FIGS. 5, 6, and 7. These figures show respective plots of power spectra computed from a vector magnitude ECG signal obtained by computing the square root of the sum of the squares of the standard X,Y, and Z lead signals of the vectorcardiogram. The power spectra were computed over the T wave according to the method of U.S. Pat. No. 4,802,491 (cited above). FIG. 5 is a plot of a power spectrum obtained by processing data obtained during electrical pacing of the heart. Notice the low level of noise. FIG. 6 is a plot of a power spectrum computed from data obtained during uncontrolled exercise. Notice that the noise level is so high as to make estimation of alternans impossible. FIG. 7 is a plot of a power spectrum computed from data obtained during bicycle exercise where the pedal rate is controlled using a metronome according to the method of this invention. Notice that the artifact induced in the power spectrum resulting from the pedaling does not interfere with the estimation of the peak at the alternans frequency or the reference noise band. In this spectrum one also sees an artifact resulting from respiration which in this case also does not interfere with the alternans measurement.

Example: Other Exercise

Similar considerations apply to the conduct of a treadmill stress test, except that the during a treadmill test motion artifact is introduced into the electrocardiogram at a fundamental frequency of half the step rate and the harmonics of the fundamental. So the desired step rate ranges may be calculated by setting SR=2 PR where SR is the step rate on the treadmill and PR is the pedal rate calculated above for bicycle exercise. The operator may select a protocol with designated heart rate and step rate ranges. The apparatus may indicate to the subject his actual step rate and target range (for example near ⅓ the heart rate), using a means of measuring step rate such as an accelerometer or means to analyze the electrocardiogram signal noise induced by stepping. A metronome may be used to indicate the desired stepping rate. The operator may set the speed of the treadmill to make achieving the desired step rate comfortable to the subject, and then the incline of the treadmill may be adjusted manually by the operator or automatically by the apparatus so that the heart rate is maintained within the desired range. The analysis algorithm may ignore data segments in which the target heart rates and pedal rates do not fall within the desired ranges.

Similar considerations apply to conduct of stair stepping tests as well as to bicycle and treadmill tests.

B. Respiration Artifacts

Another preferred embodiment of the invention reduces the effect of interfering noise having frequency components that interfere with the alternans measurement generated by respiratory activity in the patient. We have realized that respiration is a rhythmic activity that may interfere with the alternans measurement. The interfering action of respiration is more pronounced during exercise when respiratory effort is intensified. Respiratory activity, or the harmonics of respiratory activity, may overlap with the alternans frequency or the reference noise bands. Generally, the fundamental frequency of respiration falls below the alternans frequency of one half the heart rate and can be simply removed by filtering or by looking at the power spectrum of the signal. However, we have learned that harmonics of respiratory activity may introduce a signal component at the alternans frequency, if the respiration occurs at or near a submultiple of the patient's heart rate. This kind of interference cannot be filtered out with passive filtering techniques.

In a preferred embodiment, the respiratory rate of the subject is controlled to be at a desired rate. The respiratory rate is preferably controlled by having the subject breath in response to a metronome that provides auditory or visual cues to the subject to initiate inspiration. The rate of the metronome is preferably set to a comfortable breathing rate that does not result in interference with alternans measurement resulting from respiration or its harmonics. For example, the metronome rates at either one-third or two-thirds the heart rate are convenient. The heart rate is monitored and the results are used to adjust the frequency of the metronome. In another embodiment, respiratory activity is monitored and respiratory activity signal is used to compensate for the interfering effects of respiration on the determination of alternans. This embodiment of the invention is discussed below.

To reduce the effect of respiration on alternans measurements, one may measure a signal closely related to respiration which is derived from the electrocardiogram signal itself. This signal is derived from measurements of the amplitude or vectorcardiographic spatial angle of electrocardiographic waves such as the QRS complex (e.g., see "Clinical Validation of the ECG-Derived Respiration (EDR) Technique," by G. B. Moody, R. G. Mark, M. A. Bump, J. S. Weinstein, A. D. Berman, J. E. Mietus, A. L. Goldberg, Computers in Cardiology 1986, IEEE Computer Society Press, Washington, D.C., 1987, which is herein incorporated by reference). This approach is convenient because it does not require a separate transducer and apparatus to measure a signal closely related to respiration.

Another way to use the electrocardiogram signal to reduce the effects of respiration is to use the amplitude or orientation of T-wave itself. One method involves measurement of the energy in the T-wave measurements occurring at frequency bands at even sub-multiples of the heart rate and rejecting data segments where such energy is high (as described above). Another method involves development of a continuous respiration signal which is phase locked to the T-wave (or other respiration-related signal) using phase-locked loop techniques well known in the art, and to develop signals at harmonics of the respiration signal using the same phase-locked loop techniques. The electrocardiogram could then be corrected for respiration using these phase-locked signals and the multi-dimensional linear finite impulse moving average filter described above.

III. Signal Processing

A. Abnormal Beats

Grossly abnormal waveforms, such as premature atrial and ventricular beats, disrupt subtle temporal pattern of beat-of-beat variability in waveform morphology, such as alternans. Abnormal beats can cause phase resetting of the alternans sequence so that instead of an ABABABABABAB type of pattern, a pattern of the type ABABAPBABABA might result or a pattern of the type ABABAPABABAB might result, where P designates a premature beat. The premature beat can be readily identified and in the prior art has generally been replaced with a mean beat (average of A and B). However the since the phase of all the beats following the premature beats may be reset, the overall energy at the alternans frequency (i.e., at exactly half the heart rate) may be reduced. Thus, analysis of the beat sequence, even excluding the premature beat itself, is subject to large errors. It is found that premature beats located in the middle section of a data epoch tend to cause the largest error in the estimation of alternans. For example, if the voltage of a point on the T-Wave is represented by the sequence $V_n = V_o + a(-1)^n$ where n is the beat number, a is the amplitude of the alternating component, and $V_o$ is the mean voltage. Then, the squared amplitude of the alternating component, $a^2$, can be obtained by multiplying $V_n$ by $(-1)^n$, summing over n=1 ... N where N is the number of beats in the sequence, dividing by N, and squaring the result. This computation is equivalent, within a proportionality constant, to computing the magnitude of the power spectrum at the alternans frequency (0.5 cycles per beat). However, if the sequence $V_n$ has a phase reversal precisely half-way through the sequence, then the computation results in a value of zero. The result of the computation approaches the correct value of $a^2$ as the phase reversal approaches the beginning or end of the sequence Abnormal beats may be identified by determining if their morphology differs from the normal waveform morphology by more than a predetermined threshold or if the preceding intercycle interval differs from the mean intercycle interval by more than some predetermined threshold. Once the abnormal beats are identified, it is generally advantageous to choose a data epoch with few or no abnormal beats. If some abnormal beats remain in the data epoch to be analyzed for the presence of alternans, the level of alternans may be computed according to one of the following preferred embodiments.

Example: Estimating Alternans Over a Frequency Band

Figure 8:
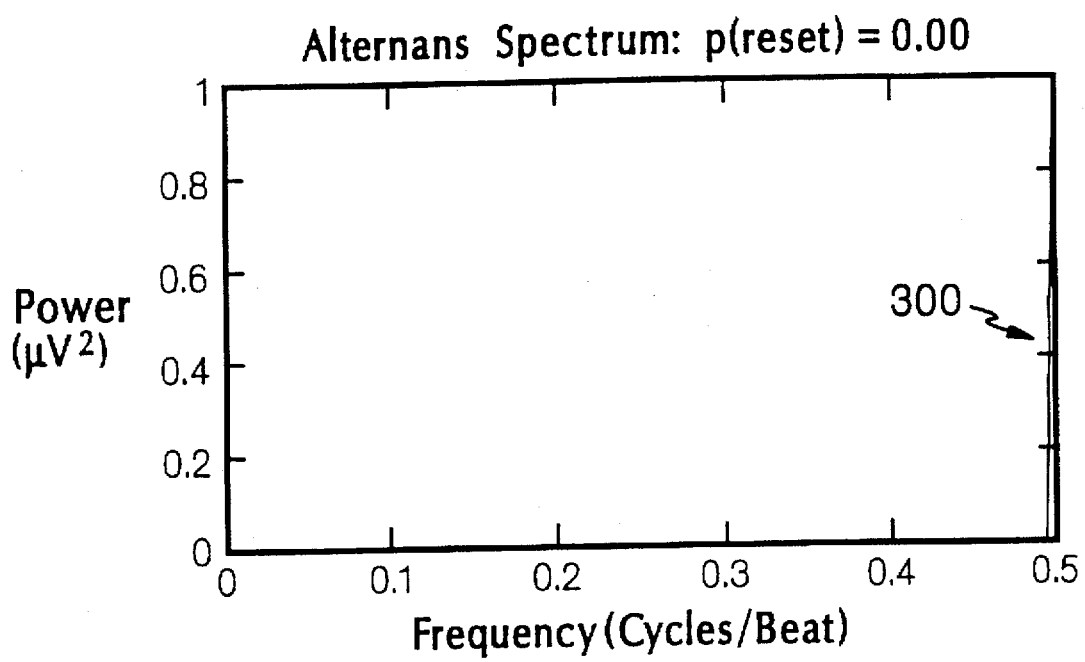
FIGS. 8 and 8A are respective power spectra plots corresponding to a "perfect" alternans pattern and a pattern in which it is assumed that there is a 5% probability of phase-resetting at each beat.
Figure 8A:
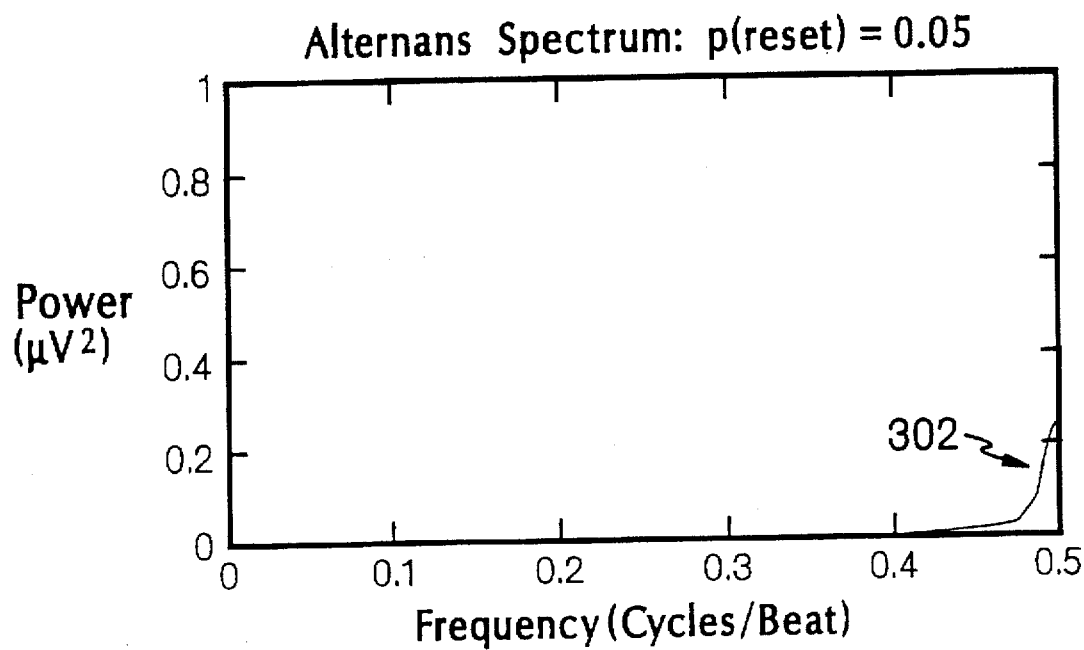

According to one embodiment of the invention, the abnormal beats are replaced with the mean normal beat and then the power spectrum is computed according to one of the methods known in the art (e.g., Cohen et al., U.S. Pat. No. 4,802,491, cited above). As shown in FIGS. 8 and 8A, the presence of phase resettings tends to broaden the peak at the alternans frequency. Referring to FIG. 8, for a "perfect" alternans sequence [+1, −1, +1, −1, ... ] of 128 points, the alternans spectrum has a clean, sharp spike 300 at the alternans frequency. When an alternans sequence has a 5% probability of phase-resetting at a given beat, the alternans peak 302 is broadened, as shown in FIG. 8A. Thus the level of alternans, in the presence of abnormal beats which may reset the phase of the alternans, is computed by integrating the power spectrum over frequencies adjacent to the alternans frequency.

The desired range of frequencies may be estimated by simulating phase-resetting caused by abnormal beats, e.g., by using the sequence $X(i) = (-1)^i$ with a length corresponding to the number of beats in the epoch. This sequence is modified by setting the values of X(i) equal to zero at values of i corresponding to abnormal beats and then for each abnormal beat multiplying the value of all subsequent points in the sequence by 1 or −1 (the value of 1 or −1 for each abnormal beat is chosen randomly). The power spectrum of the resulting sequence is computed and averaged for several realizations of the random phase resetting, and the width of the spectral peak at the alternans (Nyquist) frequency is measured. This width is used to determined the range of frequencies used to integrate the power spectrum obtained from the physiologic data to estimate the level of alternans. It is understood in this preferred embodiment that one may perform operations equivalent to integrating the power spectrum over a wider range of frequencies. In this preferred embodiment, it is preferable to choose a data epoch where the abnormal beats are not located near the center of the epoch.

In another aspect of this preferred embodiment, instead of replacing the abnormal beats with the mean normal beat, the abnormal beats are eliminated from the beat sequence and from the simulated sequence used to estimate the width of the alternans peak in the power spectrum.

Example: Combining Analyses of Normal Beat Sequences

In another preferred embodiment, one separately analyzes each sequence of normal beats between abnormal beats and combines the analyses in such a way that the fact that the phases of the different sequences may be different does not affect the alternans measurement. One expects no phase resetting within each sequence of normal beats, but different sequences may have different phases (e.g., one sequence may have a 1, −1, 1, −1 . . . pattern and another sequence may have a −1, 1, −1, . . . pattern). In this preferred embodiment, one uses any of the techniques in the art to estimate the level of alternans in each sequence of beats lying between abnormal beats, and then combines theses measurements. For example, one may compute the power spectrum of each sequence and then average the power spectra appropriately weighing the spectra for the number of beats contained therein. Alternatively, one may measure in each sequence a mean even beat waveform and a mean odd beat waveform, and compute an unsigned measure of the difference in these two waveforms as a measure of the level of alternans. This unsigned measure of the difference could be, e.g., the integrated absolute difference or the integrated squared difference.

Example: Stitching Together Beat Sequences

Another preferred embodiment involves combining the different sequences of beats between abnormal beats. We have realized that abnormal beats tend to reset the phase in a consistent way and this can be used to reduce the effects of interfering noise on the measurement of alternans. According to this scheme, sequences of normal beats are connected to maintain an alternating phase.

In one presently preferred embodiment, an abnormal beat is removed from a beat sequence to preserve an alternating phase between the beats, or an abnormal beat is replaced by a mean beat, depending on the position of the abnormal beat in the sequence. Abnormal beats are replaced or removed by the process shown in FIG. 9. At an initialization step, the number of beats (N) since the previous abnormal beat is set to zero (100). The value of N is increased by one (102). The next beat in the sequence is characterized (104). If the beat is not abnormal (106), the process returns to the initialization step (100), otherwise the position of the abnormal beat is recorded (108). At this stage, if N is even (110), the abnormal beat is removed from the sequence (112) and the process returns to the initialization step (100). If value of N is odd, the abnoraml beat is replaced with a mean beat (114) and the process returns to the initialization step (100).

Figure 9:
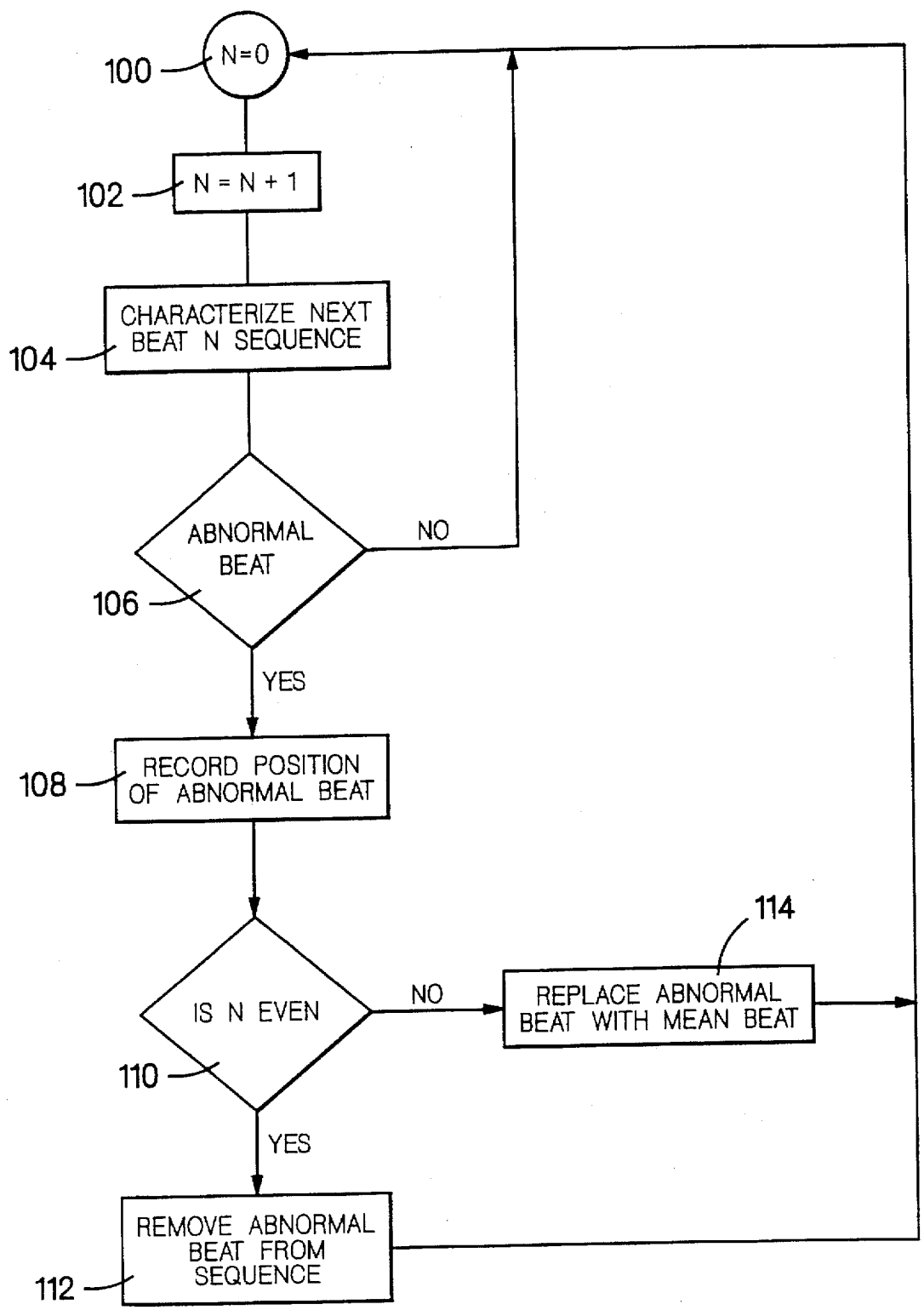
FIG. 9 is a flow diagram of a process for reducing the effect of abnormal beats on an alternans measurement.

For example, using the process shown in FIG. 9, the sequence of beats $A_1B_2A_3B_4P_5A_6B_7A_8P_9A_{10}B_{11}$ . . . is replaced with the sequence $A_1B_2A_3B_4\text{-}A_6B_7A_8\text{-}M\text{-}_{10}B_{11}$ (where A represents normal beats of phase A, B represents normal beats of phase B, P represents an abnormal premature beat, and M represents the mean beat). In this preferred embodiment, the resulting sequence of beats may be analyzed to determine the level of alternans using any of the methods in the art.

In another example, a normal beat adjacent an abnormal beat may be removed to preserve an alternating phase. For example, the sequence of beats $A_1B_2A_3B_4P_5A_6B_7A_8P_9A_{10}B_{11}$ . . . is replaced with the sequence $A_1B_2A_3B_4\text{-}A_6B_7\text{-}A_{10}B_{11}$.

B. Compensation for Interfering Variability in Measured Signals

The morphology of the physiologic waveforms may be altered by processes which interfere with the measurement of alternans ('interfering noise sources') such as the beat-to-beat variability in interbeat interval, respiratory activity, and exercise activity. In a preferred embodiment signal (which we will term 'interfering signals') are measured which contain contributions from the interfering noise sources, the interrelationship between the interfering signals and the physiologic waveforms is analyzed, and the measures of variability in the physiologic waveforms are compensated for the interfering variability.

Example: Intercycle Interval Variability

Intercycle interval variability may disrupt the temporal pattern of cycle-to-cycle variability (for example alternans) or make changes in the morphology of the physiologic waveform. Changes in the preceding R-wave to R-wave (RR) interval or intervals of the electrocardiogram cause changes in the changes in the shape and timing of the T-wave. These changes in the T-wave can mask the alternans pattern of shape changes and make the measurement of alternans more difficult. Since alternans is clinically most significant when measured during the T-wave, and measuring alternans without electrical pacing of the heart means that there will be variation in the RR interval, the sensitivity of the alternans measurement can be improved if the noise caused by this variation in interval is reduced.

Therefore, in a preferred embodiment the effect of intercycle variability on variation on waveform morphology is reduced by determining a relationship between the variation in intercycle intervals and changes in the waveform morphology. This relationship is then used to adjust the waveforms to compensate for the effect of intercycle interval variation. In one preferred embodiment, the relationship is determined by a multidimensional linear finite impulse moving average filter. Such a filter linearly relates the amplitude of the waveform at each offset from a fiducial point in the waveform to the sequence of preceding intercycle intervals:

$$V_a(i,j) = V(i,j) + \sum_k a(k,j) \cdot \Delta RR(i-k)$$

here $V_a(i,j)$ is the amplitude of the i'th waveform in a particular lead at an offset of j sample points from the fiducial point adjusted to compensate for the effect of intercycle interval variation, $V(i,j)$ is the corresponding unadjusted amplitude, and $\Delta RR(i-k)$ is the deviation of the intercycle interval k beats prior to the i'th beat from the mean. The sum over k ranges from 0 (for the immediately intercycle interval) to a maximum integer value of p. The coefficients $a(k,j)$ relate the variation in the preceding intercycle intervals to the variation in the waveform amplitude. The coefficients a(k,j) can be determined by least squares estimation techniques which are well known in the art. In a preferred embodiment the maximum value of the index k is between 1 and 5 the sampling interval is 40 milliseconds.

Figure 10:
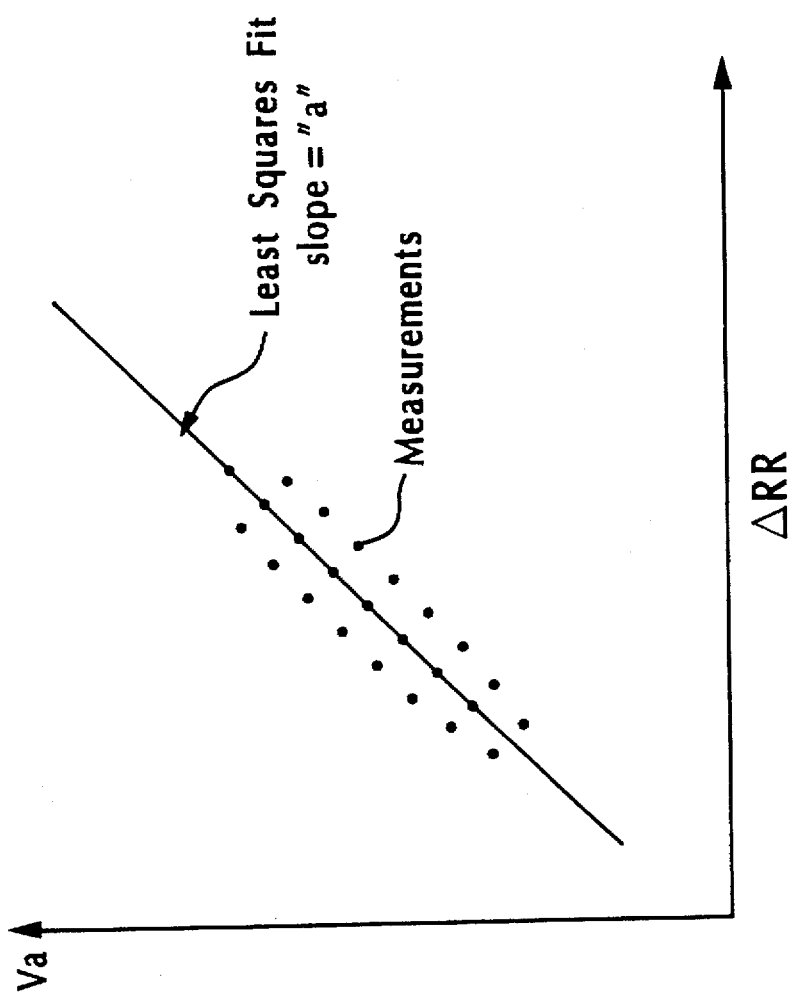
FIG. 10 is a plot typical of the relationship between the amplitude, $V_a$, on one point on a waveform at a specified offset from a fiducial point and the $\Delta RR$ interval, the deviation from the preceding interbeat interval and the mean beat interval.

FIG. 10 demonstrates how this works for correcting a single point on the T-wave. Measurements are made of the voltage ($V_a$) of a series of T-waves at this point and these are related to the deviation ($\Delta RR$) of the previous RR interval from the mean RR interval. A least squares fit to these data provides the coefficient "a" (corresponding to the slope), which can be used to correct this point on the T-wave for the variation in the previous RR interval.

Figure 11:
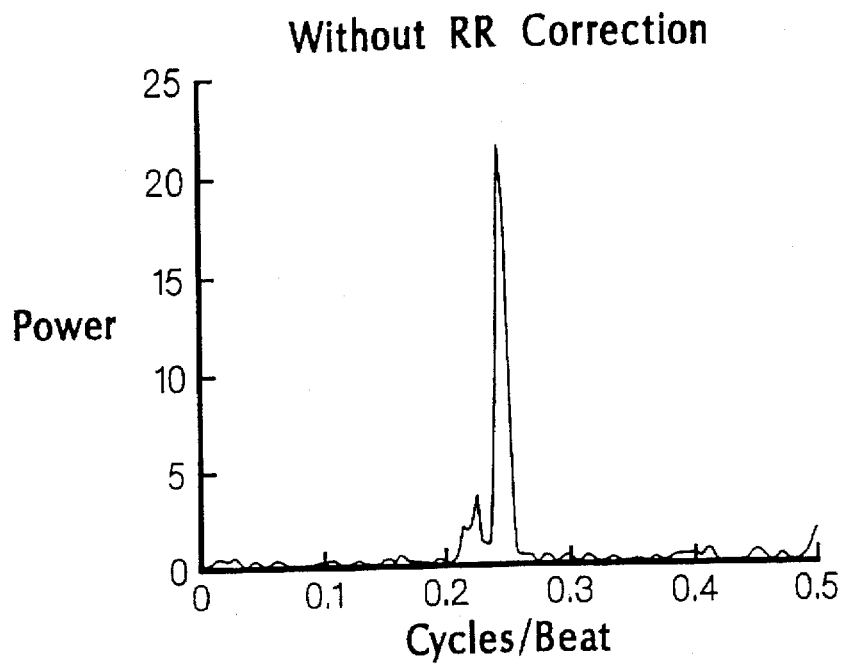
FIG. 11 is a plot of a power spectrum of data in which there is RR interval variation.
Figure 12:
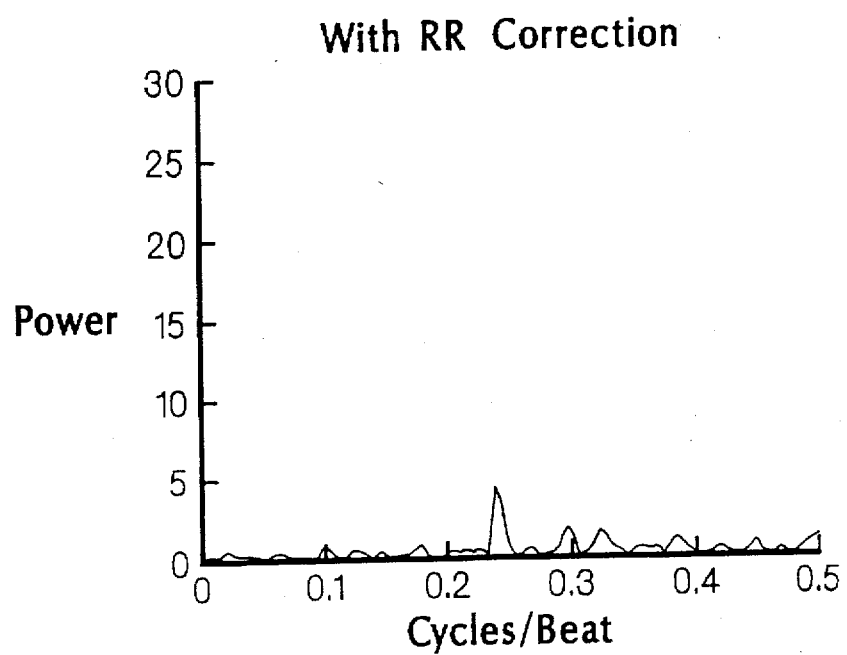
FIG. 12 is a plot of a power spectrum of the same data as FIG. 11 using the method of the invention to compensate for RR interval variation.

FIG. 11 shows the alternans spectrum calculated by the means described in Smith et al., 1988 (cited above), where RR interval variation has caused an elevation of the noise levels. FIG. 12 shows a spectrum of the same data where the moving average filter described above has been applied. Note that the noise level in the spectrum has been reduced.

Other means are available to perform the same task. For example, each T-wave can be represented as a weighted sum of basis functions. These basis functions can be obtained by performing a principal components analysis of all of the T-waves in the data epoch using methods well known in the art. Then each T-wave is represented as follows:

$$V(i,j) = \sum_k c(i,k) \cdot b(i,j-k)$$

where V(i,j) is the amplitude of the i'th waveform at an offset of j sample points from the fiducial point, c(i,k) is the weighting coefficient for the kth basis function for the i'th waveform, and b(k,j) is the value of the $k^{th}$ basis function at the $j^{th}$ sample point offset.

The coefficients c(l,k) may in turn be adjusted to compensate for the effect of interbeat interval variability:

$$c_a(l,k) = c(l,k) + \sum_n d(m,k) \cdot \Delta RR(l-m)$$

where $c_a$(l,k) is the adjusted value of the coefficient, d(m,k) is a set of coefficients relating coefficients for the $k^{th}$ basis function to $\Delta RR$(l-m), which is the deviation of the preceding RR intervals from the mean. The value m is summed over a range starting with m=0 (the immediately preceding $\Delta RR$). The coefficient d(m,k) may be computed using a least squares minimization procedures well known in the art. The adjusted values of the waveform, $V_a$(i,j) is then computed:

$$V_a(i,j) = \sum_k c_a(i,k) \cdot b(j,k).$$

In another preferred embodiment, the effect of RR interval variability is represented as a change in the amplitude and offset of the T-wave:

$$V_a(i,j) = \alpha(i) \cdot V(i, j-\beta(i)).$$

Here, $\alpha(i)$ and $\beta(i)$ represented the modified amplitude and offset of the $i^{th}$ waveform. The values of $\alpha(i)$ and $\beta(i)$ may be related to the preceding $\Delta RR$ (l-m) using a filter such as linear moving average filter, as described above.

In a preferred embodiment, these methods for compensating for the effects of intercycle variability are applied during physiologic stress.

Example: Variability in Other Signals

The measurement of the alternans pattern of waveform variability without direct electrical pacing of the heart often involves the detection of generally smaller signal levels, the detection at a broader range of heart rates, and the detection in the presence of other physiological variability which may be caused by exercise or other physiological stress. Therefore, one preferred embodiment is a method for assessing the alternans pattern of cycle-to-cycle variability in physiologic waveforms of a physiologic signal in which the effect of variability in one or more other signals on the variability in the physiological signal being measured is reduced by determining a mathematical relationship which relates measures of the variability in the other signal or signals to measures of the variability in the physiologic signal being measured and using this mathematical relationship to adjust the measures of the variability of the physiologic signal being measured to compensate for the effect of variability in the other signal or signals.

Figure 13:
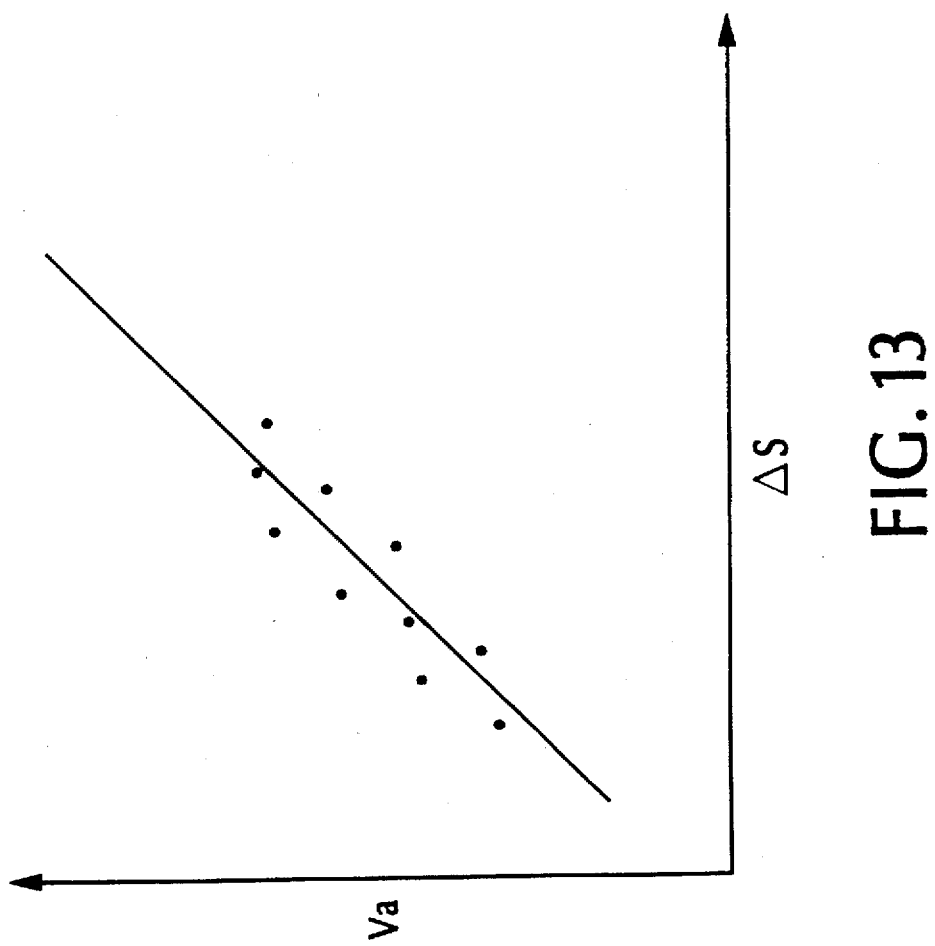
FIG. 13 is a plot typical of the relationship between $V_a(i,j)$ and S, the contemporaneous value of the respiration signal.

For example, respiration can affect the shape of electrocardiographic complexes thus making it more difficult to measure the alternans pattern of variation. The level of respiration is increased during exercise and physiological stress and therefore the problem becomes more acute when physiological stress is used for the measurement of alternans. By measuring a signal closely related to respiration (such as an impedance plethysmography signal which can be measured from the same electrocardiographic electrodes using techniques well known in the art) as well as the electrocardiogram signals, one can determine a mathematical relationship between the respiration related signal and the morphology of the electrocardiographic waveforms. For example, the mathematical relationship may be characterized as a multidimensional linear finite impulse moving average filter relating the amplitude of the electrocardiographic waveform at each offset from a fiducial point in the waveform to the amplitude of the respiratory signal. One example of such a filter is similar to that described above for the compensation of the effects of variation in intercycle interval $$V_a(i,j) = V(i,j) + \sum_k a(k,j) \cdot \Delta S(i,j-k)$$

where $\Delta S(i,j-k)$ is the deviation of the respiration related signal from its mean value at k sample points preceding the time associated with $V_a(i,j)$. Here the coefficients a(k,j) related the variation in the amplitude of the respiration related signal S with the variation in the electrocardiographic amplitude given by V(i, j) (see FIG. 13). In one preferred embodiment, significant benefit is obtained when the maximum value of the index k is unity. In this preferred embodiment the electrocardiographic amplitude is corrected by the contemporaneous value of the respiratory signal. It may also be necessary to create filters to compensate for signals equal to $\Delta S$ raised to integer powers to adjust for the effects of harmonics of respiration related signals on the morphology of electrocardiographic signals.

Figure 14:
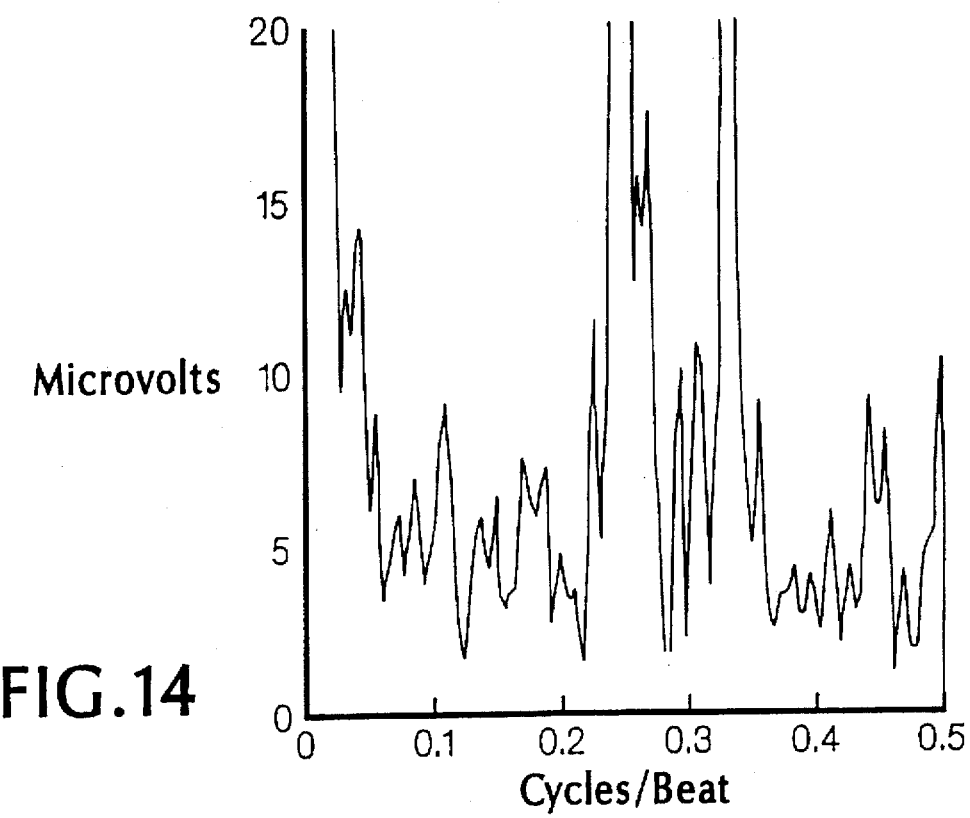
FIGS. 14 and 14A are plots of power spectra in which a harmonic of respiration overlaps with the alternans frequency, before and after correction for respiration artifact, respectively.
Figure 14A:
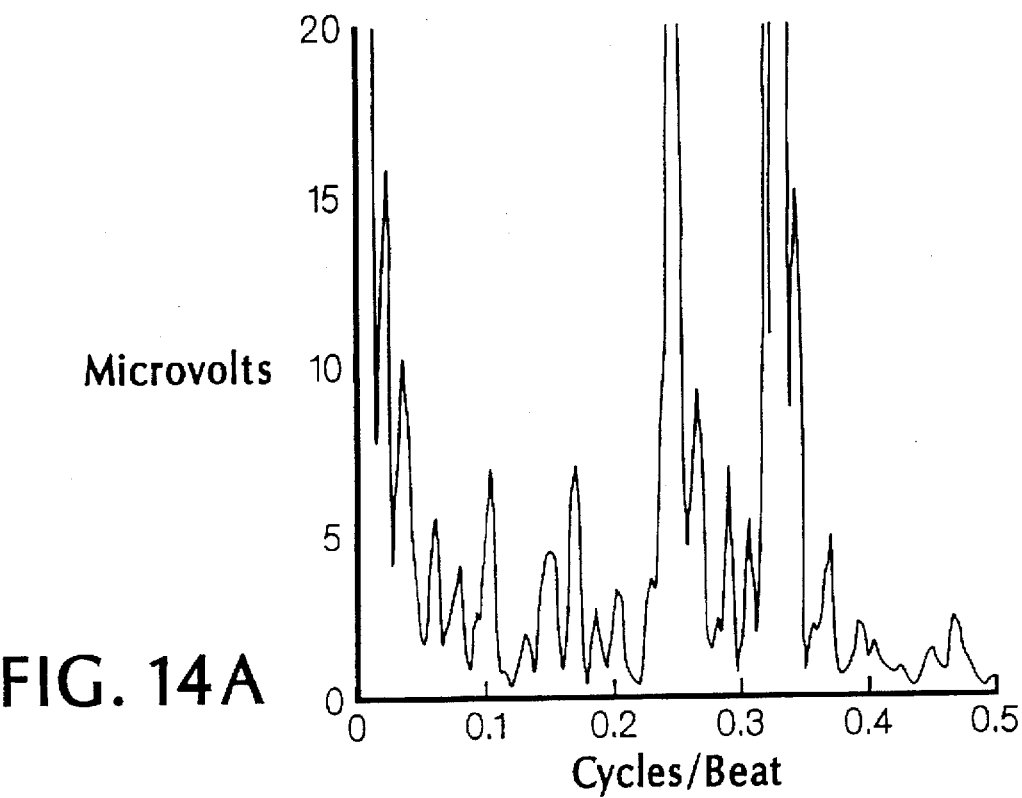

The importance of correcting for the effect of respiration is illustrated by a study conducted by us of the level of alternans in thirty healthy young adults during bicycle exercise. In the absence of compensation for the effects of respiration, eight subjects were found to have a significant level of alternans. This quite surprising result occurred because they were breathing at a sub-multiple of their heart rate. As a result, one of the harmonics of their respiration created a variation in their ECG waveform morphology at the alternans frequency (see FIG. 14, which shows respiration from one of these subjects at one quarter of the heart rate producing a false positive peak at the alternans frequency of one half the heart rate). However, as shown in FIG. 14A, when the electrocardiographic waveforms were adjusted using an independently measured impedance plethysmographic respiration related signal, alternans fell to insignificant levels.

C. Use of Multiple Electrodes or Multi-segment Electrodes

Signals recorded from multiple electrodes may be used to reduce the effect of noise which interferes with the measurement of a temporal pattern of cycle-to-cycle interval variation in physiologic waveforms. In one preferred embodiment one simply obtains the measure of the alternans pattern of cycle-to-cycle variation in physiologic waveform morphology in electrocardiographic signals which is the level of alternans in those leads in which the level of alternans exceeds the noise by approximately 2 or 3 standard deviations. This preferred embodiment ignores the leads in which the noise may be so high as to make it impossible to detect alternans.

A description of a systematic method for mathematically analyzing multiple signals to reduce the effect of noise on the measurement of a temporal pattern of cycle-to-cycle variation in physiologic waveforms is described in U.S. patent application Ser. 08/339,032, filed Nov. 14, 1994, entitled "Measuring a Physiologic Signal," which is hereby incorporated by reference. In a preferred embodiment, an assessment of the temporal pattern of cycle-to-cycle variation in electrocardiographic waveforms is accomplished by applying to a subject a multiplicity of electrodes, recording signals from the electrodes, determining the mathematical relationship between the signals from the different electrodes, defining an error metric, and finding a mathematical combination of electrode signals to approximate a desired set of electrocardiographic lead signals which also reduces the error metric, and analyzing the temporal pattern of cycle-to-cycle variability in the electrocardiographic waveforms of the mathematical combination of electrode signals. This method may be applied where the temporal pattern being assessed is alternans. In one preferred embodiment, the desired set of electrode lead signals are the X, Y and Z leads of the vectorcardiogram. In another preferred embodiment, the desired set of electrocardiographic lead signals are approximated over one or more segments of the electrocardiographic waveforms. In another preferred embodiment, the mathematical relationship involves the co-variance.

In one preferred embodiment, the error metric involves a measurement of noise over one or more segments of the electrocardiographic waveforms, such as the PQ segment or the T-wave. In another preferred embodiment, the error metric involves measurement of noise over one or more frequency bands. In another preferred embodiment, the computation of the error metric involves one or more of the following: obtaining a measure of the noise, obtaining a measure of the magnitude of the temporal pattern of cycle-to-cycle variability being assessed, obtaining a measure of the relative magnitudes of the temporal pattern and the noise, and obtaining a measure of the statistical significance of the magnitude of the temporal pattern.

In one preferred embodiment, a multiplicity of individual electrodes, or a compound electrode with multiple independent electrical contacts, are applied at a localized anatomic site. The electrocardiographic signals from these multiple electrodes are then used to estimate a reduced noise signal corresponding to the electrocardiographic signal emanating from that localized anatomic site.

Figure 15:
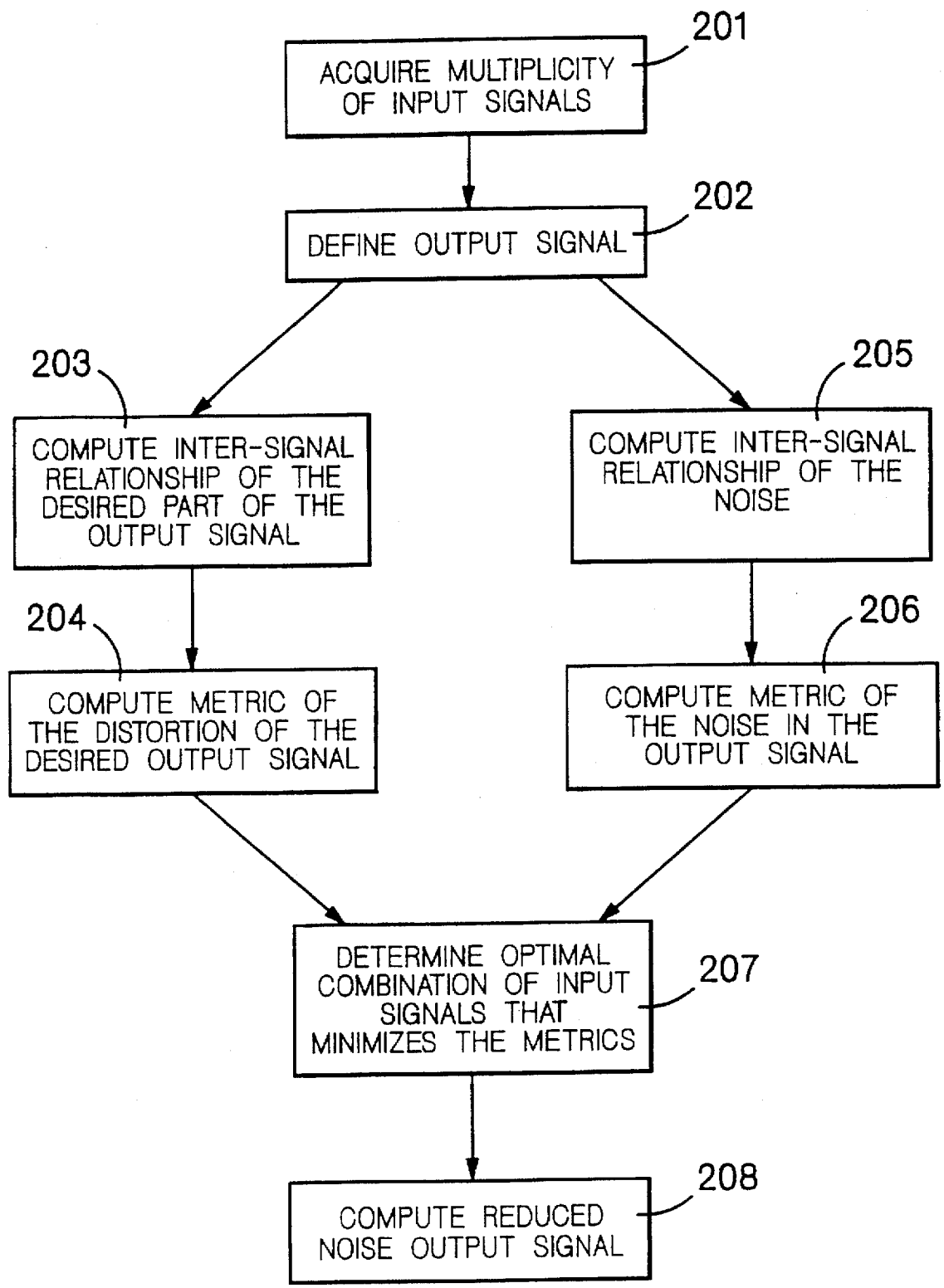
FIG. 15 is a flow diagram of a measurement method.

With reference to FIG. 15, a general method of the invention is summarized beginning with step 201 in which the input signals are acquired. Each signal is assumed to contain some amount of the desired signal or some amount of the noise signal, or both. In step 202 the decision is made as to what kind of output signal is to be generated. Often, the desired output signal is simply one of the input signals but, more generally, it can involve transformations of the input signals.

Steps 203 and 204 define the relationship of the desired signal among the input signals. Step 203 first transforms the input signals by means of a mathematical process that has a filtering effect which preserves the desired features and then computes the inter-signal relationship of the features is by computing the correlation between the processed signals. Then, in 204, a distortion metric is created which uses the correlation function to establish a measure of how any specific combination of input signals will distort the desired features of the output signal.

Steps 205 and 206 are similar to steps 203 and 204 except that the mathematical transformation preserves the noise features of the signal, and the metric measures of how much noise any given combination of input signals contributes to the output signal.

In step 207 the two metrics from steps 203 through 206 are considered simultaneously, and the combination of input signals which minimizes the aggregate metric is computed. The signals are combined in step 208 to produce a low noise output signal. The low noise signal is referred to as the optimized signal.

The method and apparatus of the invention are discussed with respect to the problem of measuring the electrical alternans in the ECG. The measurement of the electrical alternans presents a challenge because its amplitude is often as low as a microvolt. By contrast, it is not uncommon for the obscuring noise to reach peak levels of a millivolt. The noise is usually comprised of multiple sources such as beat-to-beat variability in the shape of the ECG waveforms caused by respiration, voltage fluctuations generated by displacements at the electrode-skin interface due to motion, and skeletal muscle activity.

Figure 16:
FIGS. 16–16D are plots of physiologic signals over time.
Figure 16A:
Figure 16B:
Figure 16C:
Figure 16D:
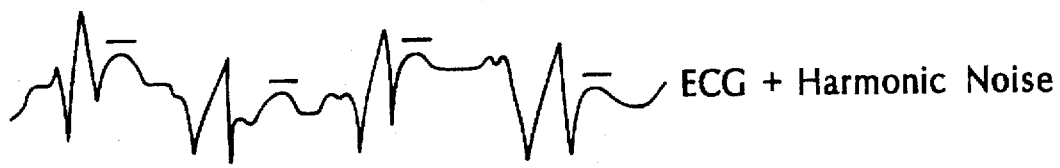

Of the three sources, the first two pose a special problem since they can act to mimic alternans. For example, as shown in FIGS. 16–16D, if the patient is breathing at one-fourth or one-sixth of the heart rate, a harmonic multiple of respiration will occur at the alternans frequency. The harmonic can impart alternans to the ECG by means of its influence on the beat-to-beat variability and by means of electrode noise generated by the respiratory motion of the chest.

An even more complicated situation can occur, when noise due to the patient motion occurring with one periodicity interacts with the respiratory effects at a second periodicity, combining in a non-linear fashion to produce noise at a third periodicity which can mimic or mask the presence of alternans. For all these reasons, the reduction of interfering noise is of paramount importance for the measurement of alternans.

The preferred embodiment demonstrates the use of the method to reduce the noise of the ECG in a manner that makes it more suitable for the analysis of electrical alternans. The apparatus measures the ECG, respiration, and ECG electrode impedance. The respiration provides a signal related to noise of the beat-to-beat variability in the ECG, while the impedance provides a signal that is related to noise cause by displacement of the electrode-skin interface.

Figure 17:
FIGS. 17–17C are plots of physiologic signals over time.
Figure 17A:
Figure 17B:
Figure 17C:

Referring to FIGS. 17–17C, respiration and impedance signals are combined to reduce the noise of the measured ECG signal.

Figure 18:
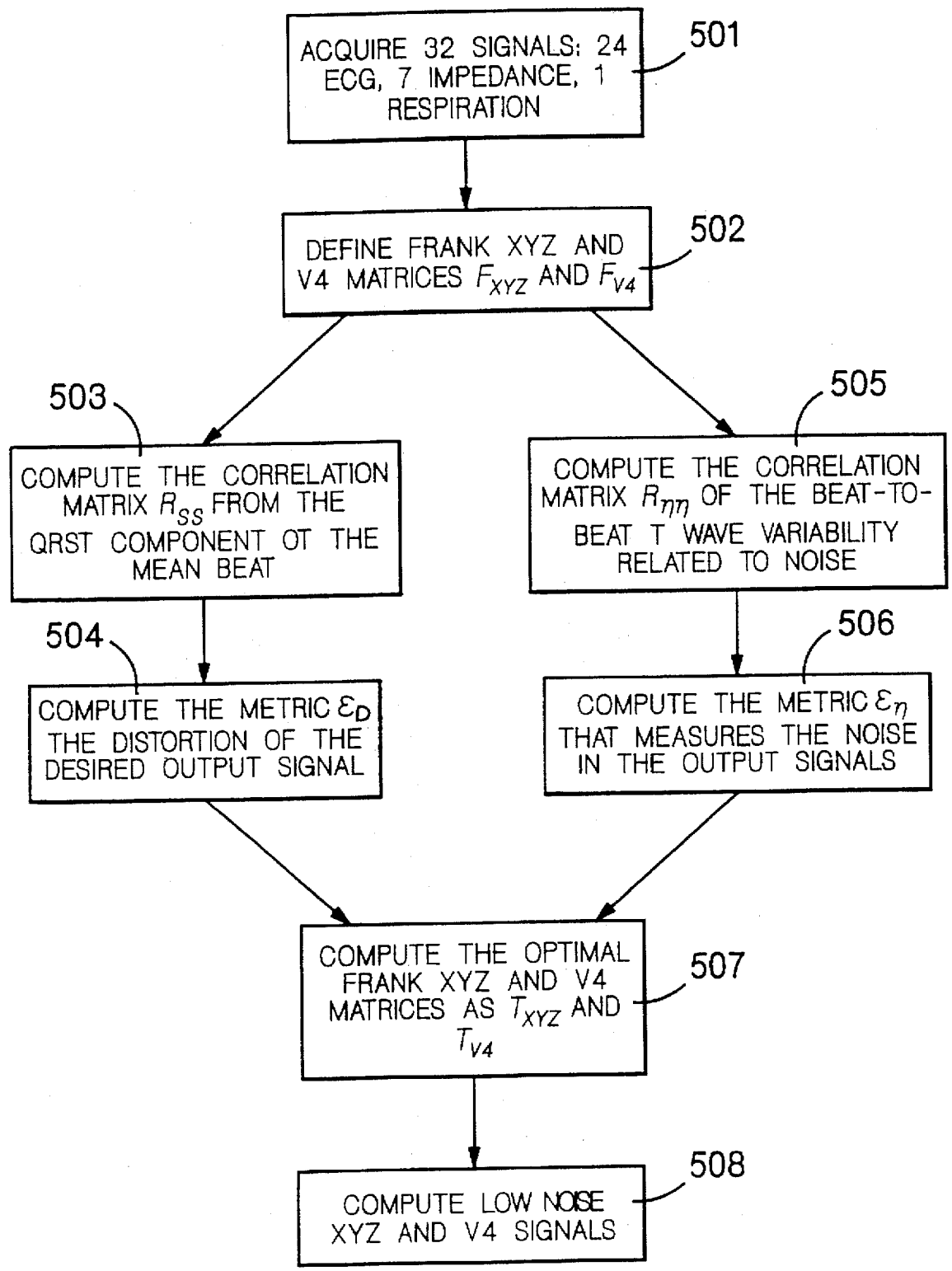
FIG. 18 is a flow diagram of the steps of a measurement method.

The steps of the preferred embodiment follow the flowchart of FIG. 18, which parallels the general method put forth in FIG. 15. The preferred embodiment uses a matrix formulation to express the method of the invention. Other embodiments may use other implementations such as tensor formulations or polynomial function formulations. The detailed mathematical justification is omitted from the description and can be found in Appendices A, B and C.

Electrode Structure

Figure 19A:
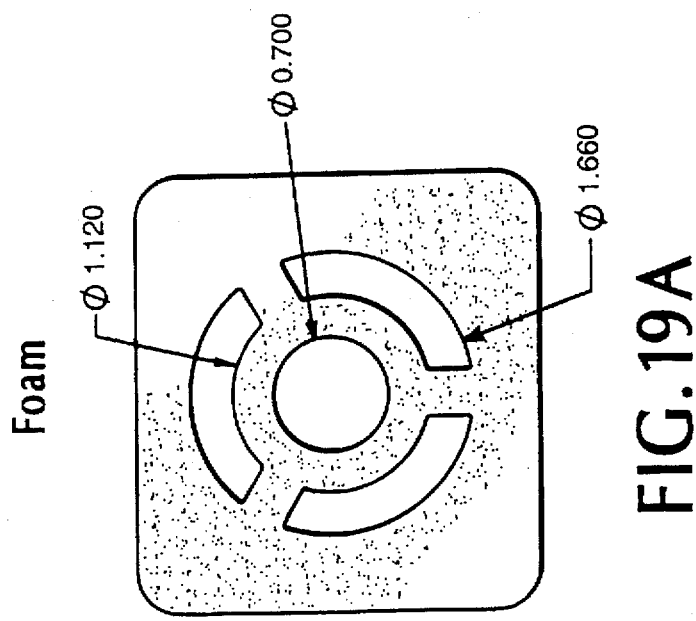
FIGS. 19 and 19A are diagrammatic views of components of a multi-segment electrode.
Figure 19:
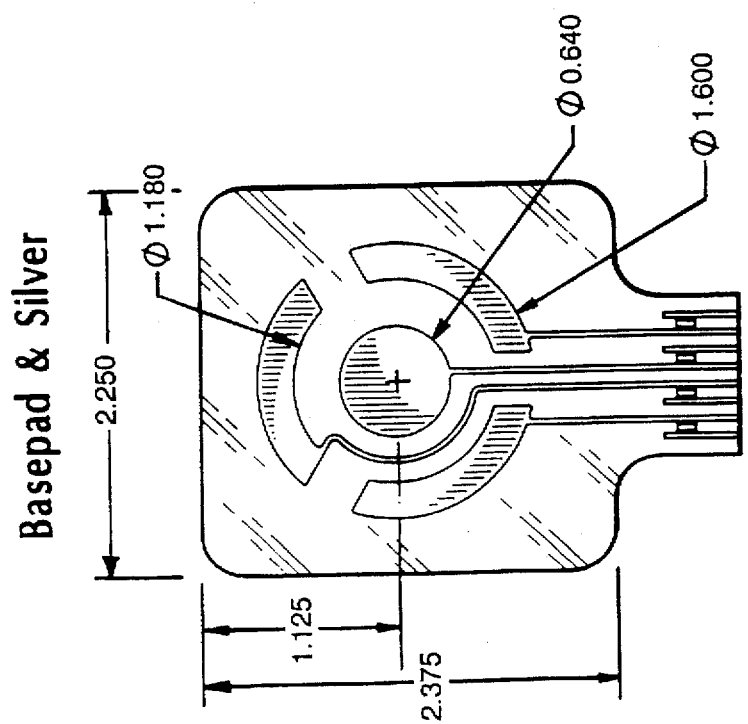

As shown in FIGS. 19 and 19A, the multi-segment electrode is constructed of a basepad made of a film printed with silver-chloride ink. The ink creates segments that provide the electrical connection to the electrode gel while providing adequate defibrillation recovery characteristics. The ink is also used to create traces which continue to the bottom edge of the basepad, where they are brought into a parallel formation suitable for an edge connector.

A plastic flexible foam is attached to the base pad. The foam covers much of the exposed areas of the traces and insulates them. It leaves the areas corresponding to the electrode segments exposed, thereby creating wells that provide convenient method of holding the gel that make the electrical connection from the ink to the skin. The foam has an adhesive on the surface that holds the electrode to the skin of the patient.

Figure 20:
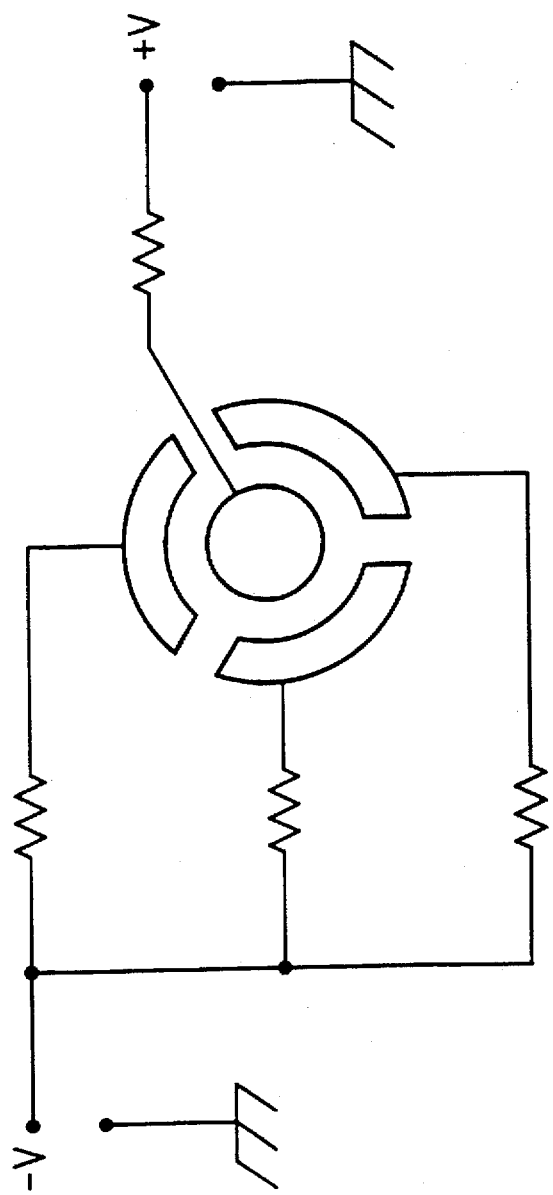
FIG. 20 is a schematic diagram of a circuit for measuring noise created by electrode movement.

The use of a multi-segment electrode has several advantages. First, the ECG recorded by the segments usually varies differently between the segments than does the noise. This is largely attributable to the differing physical locations of the source of the ECG and the source of the noise. Second, the variation in the noise caused by separation of the segments can be adjusted in a controlled fashion by introducing a small DC bias current on each segment of the electrode. FIG. 20 shows a diagram for application of the DC bias to the multi-segment electrode. The variation can also be adjusted by manufacturing the different segments using different electrolyte mixtures.

Respiration and Impedance Measurement

Figure 21:
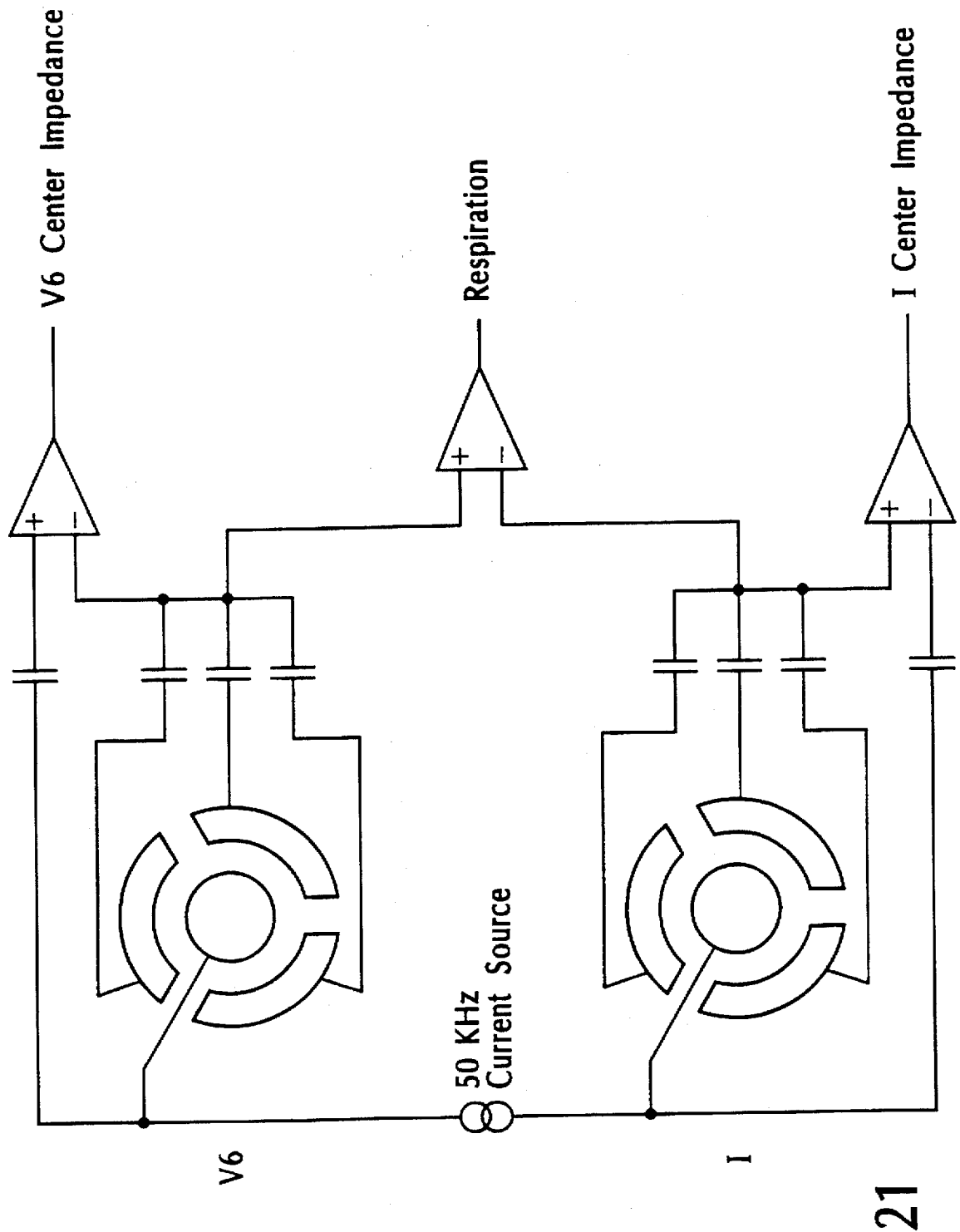
FIG. 21 is a schematic diagram of a circuit for recording ECG, respiration, and electrode impedance.

The multi-segment electrode facilitates the measurement of respiration and electrode impedance as described in FIG. 21. Impedance of the skin-electrode interface is measured because it provides a signal representative of noise, which can be used with other measured signals to help cancel noise from an alternans measurement. We belive that this procedure is particularly advantageous because we have found that changes in impedance are correlated with noise artifact in the alternans measurement, which permits noise cancellation.

The measurements are enabled by injection of a small 50 Khz current between the centers of two of the multi-segment electrodes. The outer ring segments are capacitively coupled so that, at 50 kHz, the ring acts as a single segment.

Referring to FIG. 21, respiration is measured as a 4-terminal measurement using the rings as measurement electrodes. As the impedance across the chest changes due to inflation and deflation of the lungs, the measured voltage increases and decreases. The voltage is demodulated and high-pass filtered to provide the respiratory signal.

Impedance of the center segment of each electrode is measured by measuring the voltage drop between the center and ring. Since the measurement draws essentially no current, the ring impedance has little effect on the measured voltage. The voltage is demodulated and high-pass filtered to provide the impedance signal. The multi-segment electrodes are placed at the locations whose signals are most important to the measurement of electrical alternans.

Referring to FIGS. 22 and 22A, a total of 32 signals as are acquired using the 14 ECG electrodes. Of the 32 channels, there are 24 ECG signals, 7 impedance signals, and 1 respiratory signal. The ECG signals are named after the electrodes, with the suffix "a", "b", or "c" referring to signals from the ring segments. For most of the multi-segment electrodes, two or three of the outer ring segments are joined together to form a larger segment (in order to reduce the number of ECG channels that need to be recorded). All the ECG signals are recorded referenced to Wilson's central terminal, which represents the average of the voltage at the RA, LA, and LL electrodes.

The 7 impedance signals measure the center segment impedance of the 7 multi-segment electrodes. They are given name of the electrode with the suffix "i".

The respiratory signal is a measure of the chest impedance from the right to the left side. As the lungs inflate and deflate, the impedance across the chest changes since air conducts less well than the body tissues. Respiration changes the impedance between the heart and the body surface and thereby changes in the measured ECG. Therefore, measuring respiration by impedance increases its usefulness for canceling changes in the ECG that are cause by respiratory impedance changes.

Figures 23, 24:
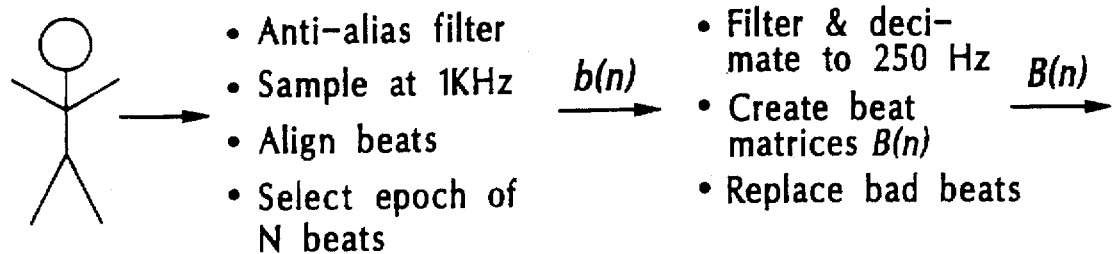
FIG. 23 is a diagrammatic view illustrating steps for preprocessing input signals.
FIG. 24 is a table defining signal elements of a b(n) matrix.

FIGS. 23–26 summarize the digitization and the preprocessing of the signals. The ECG, impedance, and respiratory signals are acquired from the patient electrodes as described in FIGS. 22 and 22A. The signals are amplified, anti-alias filtered and digitized at 1 Khz to create an M=32 dimensional time series b(k). The contents of the rows of b(k) are shown in FIG. 24.

The beats are detected, aligned and classified, and an epoch of N beats is chosen for analysis. The epoch is chosen on the basis of features such as heart rate, the availability of normal beats, and the general noise level. The heart rate is important because it has been found that alternans is more easily detected at heart rates over 100 beats per minute.

Figure 25:
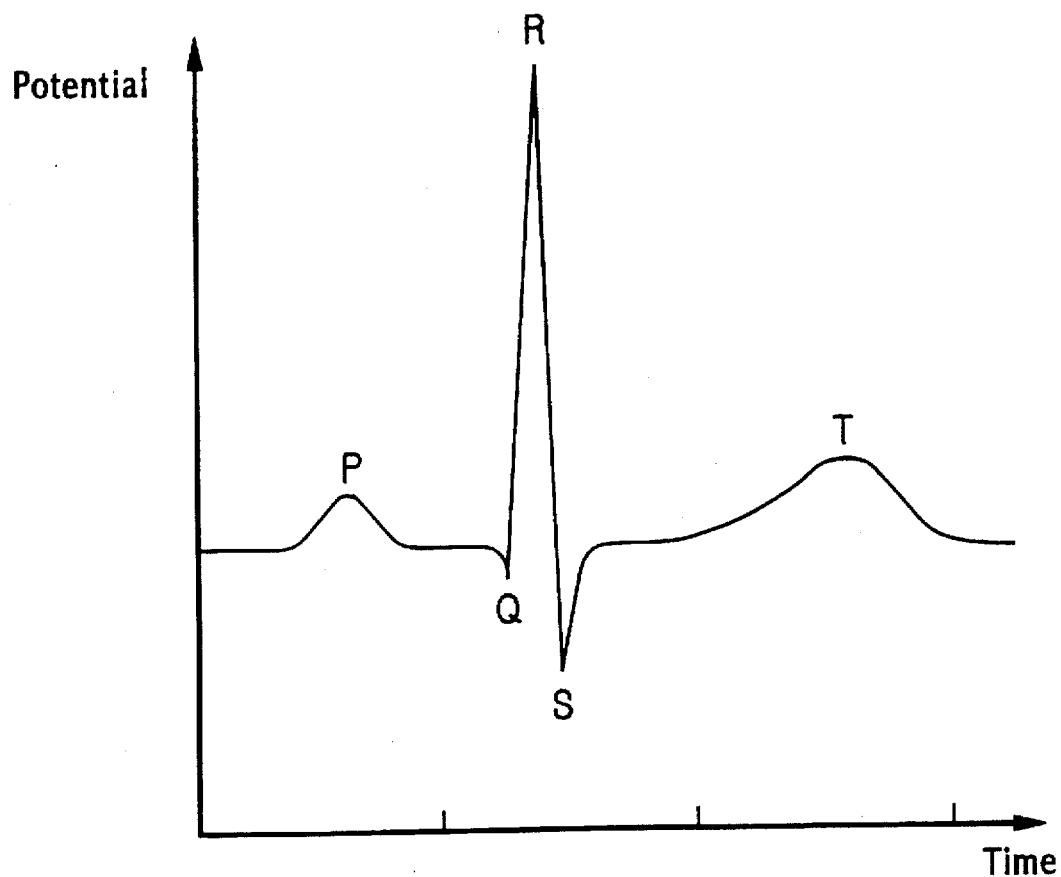
FIG. 25 is an ECG potential over a single beat.

FIG. 25 shows the features of a single ECG beat. Briefly, the P wave corresponds to activity in the atria, while the QRST complex corresponds to ventricular activity. The QRS complex represents the electrical activation of the ventricles, while the T wave represents the electrical recovery. The ST segment is a relatively quiescent period. In humans, it has been found that T wave is the best interval of the ECG complex for detecting alternans.

For each of the n=1,N beats in the epoch, the beat is aligned on the QRS complex, filtered, decimated to 250 Hz around the alignment point, and stored in matrix B(n) of dimension M×K. The decimation allows for some data reduction and lowers the data storage requirements.

Figure 26:
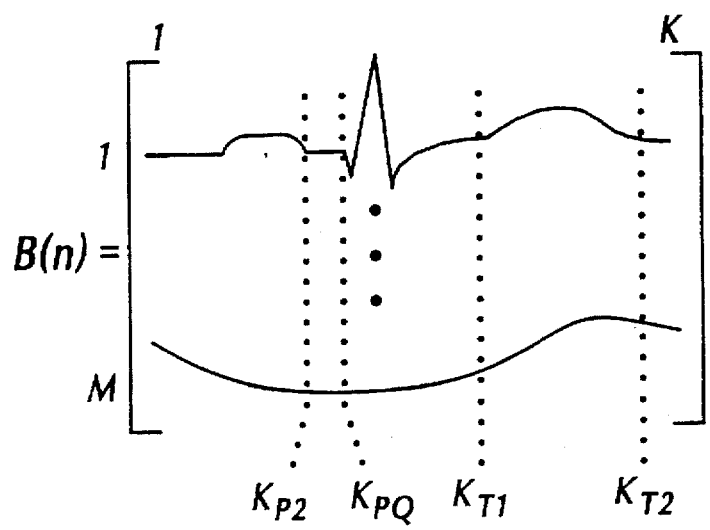
FIG. 26 is a matrix containing 32 input signals for an nth beat.

The structure of B(n) is shown in FIG. 26. Row m of B(n) corresponds to the row m of b(n). The number of columns K is determined by the duration of the longest beat. The k=1 ... K columns correspond to successive digital samples over the duration of the beat. The samples start before the beginning of the P wave and end after the T wave. The indices $K_{P2}$ and $K_{PQ}$ delineate the PR interval; $K_{T1}$ and $K_{T2}$ delineate the T wave.

Beats which are classified unusable for reasons of morphology, timing, or excessive noise are excluded from analysis. Abnormal morphology is usually the results of beats which originate from an abnormal conduction patterns in the heart. Such beats interfere with the stable manifestation of alternans. Beat which have occurred very early or very late relative to the average time interval between beats also destabilize the alternans. In the preferred embodiment, the beats B(n) which are excluded from the analysis are replaced with the mean value of B(n) computed over the remaining beats. For other preferred embodiments, replacement methods based on interpolation, filtering, or likelihood estimation may be preferable.

Output signals

Step 502 defines the output signals as the Frank XYZ vector signals and the V4 signals. The XYZ signals have the advantage that the computation of the vector magnitude from XYZ creates a signal which is immune to alternans artifact created by rotation of the heart. The V4 signal is representative of the V1–V6 signals, which are known contain information not entirely contained in the XYZ signals.

FIG. 27 shows the how the X, Y, Z, and V4 output signals are defined in terms of the input signals. Other embodiments may define output signals that include any or all of the other commonly used ECG signals such as V1–V6, or they may create signals from any generalized combination of input ECG signals.

The coefficients necessary to create the X, Y, Z, and V4 leads are represented in the row vectors $F_X$, $F_Y$, $F_Z$, and FV4 whose coefficients are shown in the table in FIG. 15. The output signals corresponding to B(n) are denoted by D(n); for example, $D_X(n)=F_X B(n)$. The 3×M matrix that consists of $F_X$, $F_Y$, $F_Z$ is defined as $F_{XYZ}$ and creates the 3×K matrix of the XYZ signals denoted by $D_{XYZ}(n)=F_{XYZ}B(n)$.

Figure 28:
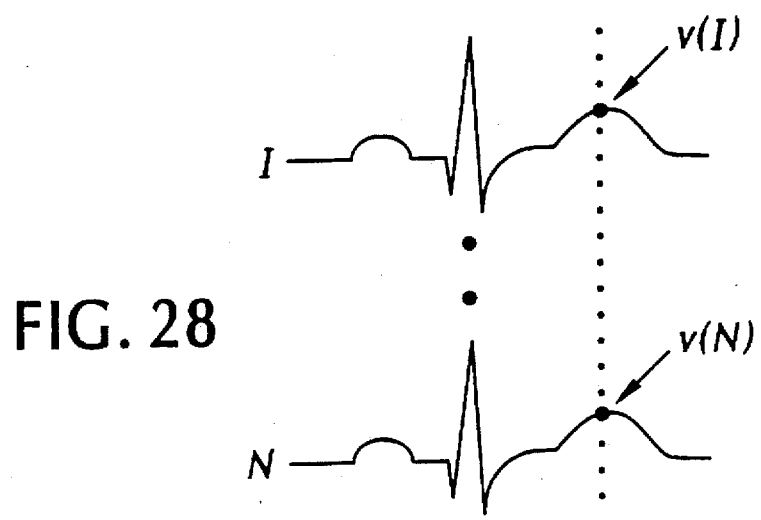
FIGS. 28–28B are plots of measured output signals.
Figure 28A:
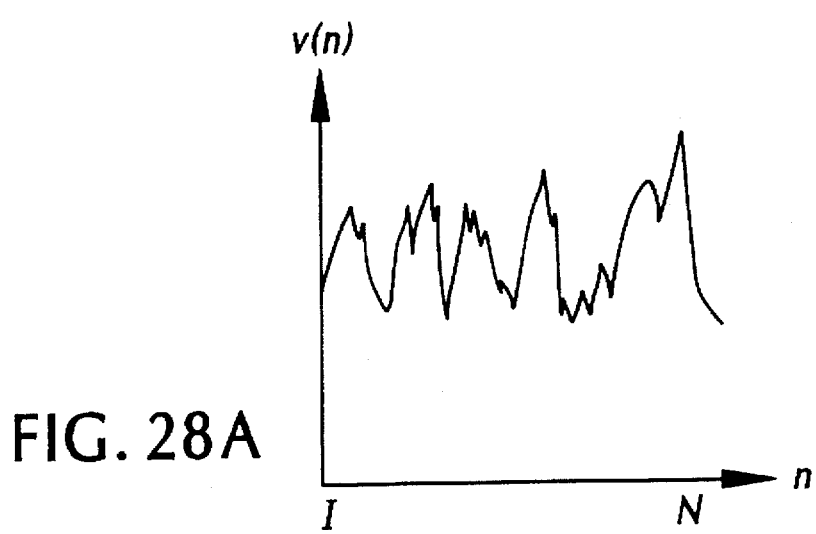
Figure 28B:
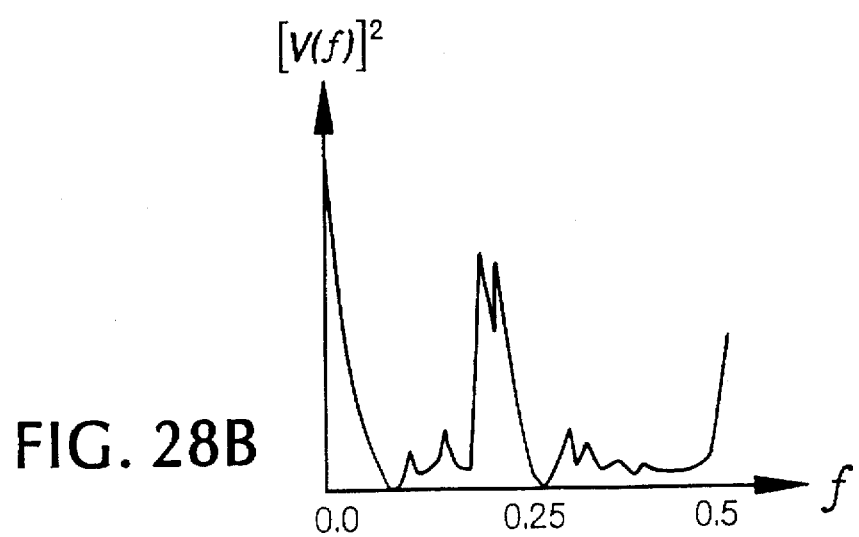

FIGS. 28–28B summarize a method of computing alternans from the unoptimized output signals $D_{XYZ}(n)$. The vector magnitude $D_{VM}(n)$ is created and the T-wave region of the vector magnitude beats is divided into columns of points as represented by v(n). The power spectrum of v(n) is computed as V(f). The frequency corresponding to 0.5 cycles per beat is the alternans frequency. The level of alternans is considered significant if it exceeds the level of noise reference band by an amount equal to three standard deviations of the level in the reference band. The alternans in the V4 lead is computed using the same procedure as the used form computing the alternans of the vector magnitude.

The matrices that create the output signals using an optimal combination of the input signals are denoted by $T_X$, $T_Y$, $T_Z$, and $T_{V4}$. The structure of the T matrices parallels that of their F matrix counterparts; however, their coefficients are not pre-defined and are computed based on the specific data obtained for a given individual or recording. Once computed, the $T_X$, $T_Y$, $T_Z$, and $T_{V4}$ replace their counterparts $F_X$, $F_Y$, $F_Z$, and $F_{V4}$ in the computation of alternans.

Computation of signal relationships and error metrics

Step 503 the uses the average value of the QRST complex of the ECG beats as the desired signal to be preserved. The mean of B(n) is computed across all the n and is scaled on a point by-point basis by the corresponding value of the square root of the average vector magnitude computed from $D_{VM}(n)$. This scaled average is denoted by BS. The inter-signal relationship, denoted by $R_{SS}$, is then computed as the M×M covariance matrix of the form $B_S B_S^*$, where only the columns of $B_S$ corresponding to the QRST are used in the computation. Step 504 uses the metric of distortion given by $$\epsilon_D = tr[(T_{XYZ} - F_{XYZ})R_{SS}(T_{XYZ} - F_{XYZ})^*] \quad [1]$$

where the "*" is a transpose operator, and tr[ ] is the trace of the square matrix. The metric measures the average power of the error in the representation of BS of the optimized output signals relative to the definition of those signals.

Other embodiments may use substantially different methods of creating $B_S$. The input signals B(n) may be transformed by much more complex filtering techniques that preserve the desired features in a series $B_S(n)$, which is then used to compute the covariance $R_{SS}$.

Other embodiments may choose to use an $R_{SS}$ that is an identity matrix. An identity matrix imposes a penalty if the coefficients of $T_{XYZ}$ differ from $T_{XYZ}$. The matrix $R_{SS}$ can also be crafted based on a priori knowledge about the input signal.

Step 505, uses B(n) processed by a filter that has a frequency response of Sin (2 πf), where f is the frequency as defined by the alternans power spectrum of FIGS. 28–28B. The filtering process creates one new $B_\eta(n)$ matrix corresponding to the each of the original B(n) matrices. The inter-signal relationship, denoted by $R_{\eta\eta}$, is then computed as the M×M covariance matrix taking in equal contribution the columns from each $\beta_\eta(n)$. Only the columns of B(n) corresponding to the T wave are used in computing the covariance. If the alternans is to be computed over intervals of the QRST other than the T wave, those intervals must also be included in the computation of the covariance. Step 506 uses the metric of noise given by $$\epsilon_\eta = tr[T_{XYZ}R_{\eta\eta}T_{XYZ}^*] \quad [2]$$

which measures the average noise power in the optimized output signals.

Preservation of the signal vector direction

Figure 29:
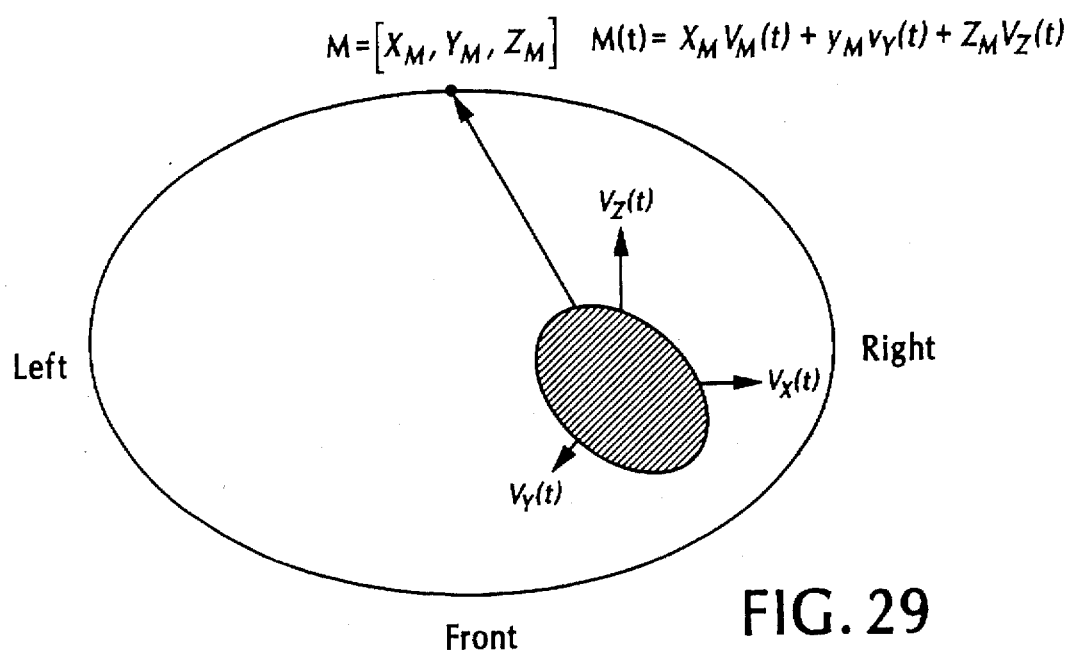
FIG. 29 is a schematic diagram of a heart represented as a dipole source.
Figure 29A:
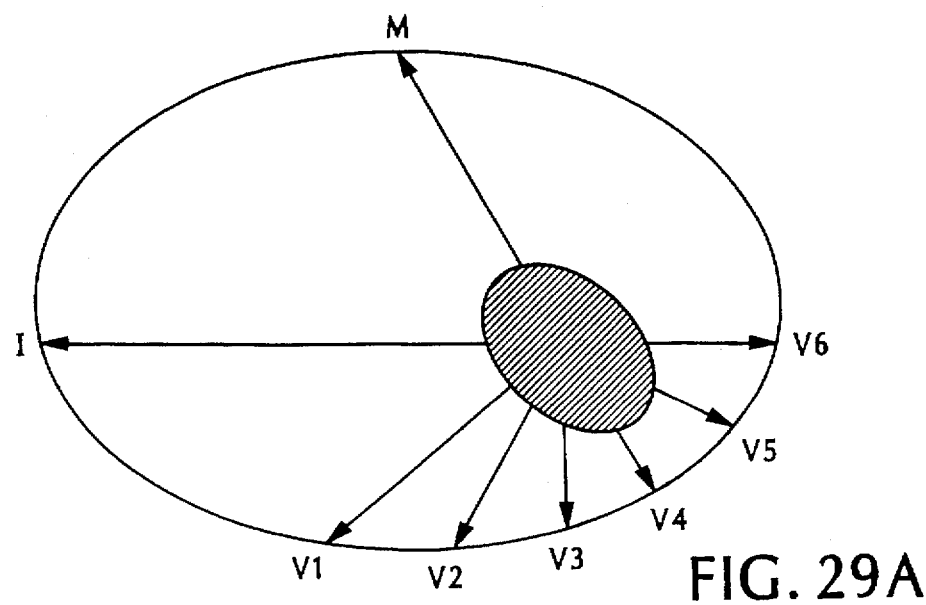
FIG. 29A is a schematic diagram of clinical ECG measurements represented as vector projections of a dipole source.

The preferred embodiment constrains the computation of $T_{XYZ}$ to maintain the mathematical orthogonality of the XYZ dipole generator defined in FIGS. 29–29A. Examining the TX component of $T_{XYZ}$ we see that it creates a combination of the 24 ECG signals, each of which consists of a specific combination of $[v_x(t), v_y(t), v_z(t)]$. When the vector contribution of all 24 ECG signals is summed together scaled by the coefficients of $T_X$, the net sum must be the vector [1 0 0]. That is to say, $T_X$ must be one unit of X contribution from the dipole source and zero units of Y or Z. The analogous computations for $T_Y$ and $T_Z$ must yield [0 1 0] and [0 0 1], respectively.

The matrix $P_{XYZ}$ is defined to contain the X, Y, and Z vector coordinates of each input signals in its three columns. Each row corresponds to a signal, with the order being same order as the columns of $T_{XYZ}$. Rows corresponding to non-ECG signals are assigned a coordinate of [0 0 0].

Using this definition of $P_{XYZ}$, the orthogonal geometry constraint can be stated as $$T_{XYZ}P_{XYZ}=I \quad [3]$$

where I is a 3×3 identity matrix. The value of PXYZ used to satisfy equation [3] is given by $$P_{XYZ}=R_{SS}F^*_{XYZ}(F_{XYZ}R_{SS}F^*_{XYZ})^{-1} \quad [4]$$

Equation [4] is derived by taking the output signals defined by $F_{XYZ}$ as the $[v_x(t), v_y(t), v_z(t)]$ of the dipole source, and then using the $R_{SS}$ inter-signal correlation matrix to compute how much X, Y, and Z is present in each of the input signals.

The solution for $P_{XYZ}$ which enforces the orthogonality constraint for the preferred embodiment, has a more general interpretation. The $P_{XYZ}$ provides the least squares means of reproducing the input signals using the subset of the information in the output signals. Therefore, the constraint defined by equations [3] and [4] may be used the for the computation of $T_{V4}$, though the interpretation becomes different.

When T is not $T_{XYZ}$, the constraint is referred to as the "round trip" constraint. It assures that if the output signal is used to estimate the input signals, and those input signals are in turn used to recompute the output signal, then recomputed output will be the same as the original output. Other embodiments may choose to use the "round trip" constraint.

Computing the optimal combination

The two metrics are combined into a single metric given by $$\epsilon = \epsilon_\eta + \alpha \epsilon_D \quad [5]$$

and the value of $T_{XYZ}$ is computed to minimize subject to the orthogonality constraint of equation [1]. The value of $T_{XYZ}$ that minimizes equation [3] is given by $$T_{XYZ} = T_0 + \alpha F_{XYZ} R_{SS} R^{-1}{}_0 (I - P_{XYZ} T_0) \quad [6]$$

where $$T_0 = (P^*{}_{XYZ} R^{-1}{}_0 P_{XYZ})^{-1} (P^*{}_{XYZ} R^{-1}{}_0) \quad [7]$$

and $$R_0 = R_{\eta\eta} + \alpha R_{SS} \quad [8]$$

In the preferred embodiment, the value of $\alpha$ is usually between 10 to 100. For other embodiments, it may not be appropriate to minimize the desired signal distortion. In that case, X is 0 and $T_{XYZ}$ is given by $$T_{XYZ} = (P^*{}_{XYZ} R^{-1}{}_{\eta\eta} P_{XYZ})^{-1} (P^*{}_{XYZ} R^{-1}{}_{\eta\eta}) \quad [9]$$

Other embodiments may choose to minimize the distortion error by reconstructing the original signals from the optimal output signals and comparing them to the original input signals. This is accomplished by replacing the distortion metric in equation [1] with $$\epsilon_D = tr[(PT - I) R_{SS} (PT - I)^*] \quad [10]$$

Computing the optimal V4

By analogy to the argument leading to the derivation of equation [3], $T_{V4}$ creates linear combination of the 24 ECG signals, each of which consists of some combination of $[v_X(t), v_Y(t), v_Z(t)]$ as defined in FIGS. 29–29A. When all the vector contribution of each of the 24 ECG signals is summed together using the coefficients of $T_X$, the net sum must be the $P_{XYZ}$ row that corresponds to V4. Denoting that row as $Q_{V4}$, the analogy to equation [3] becomes $$T_{V4} P_{XYZ} = Q_{V4} \quad [11]$$

The value of $T_{V4}$ is computed to minimize with of equation [5] $F_{V4}$ and $T_{V4}$ in place of FXYZ and TXYZ, subject to the constraint of equation [11] is given by $$T_{V4} = Q_{V4} T_0 + \alpha F_{V4} R_{SS} R_0^{-1} (I - P_{XYZ} T_0) \quad [12]$$

Figure 30:
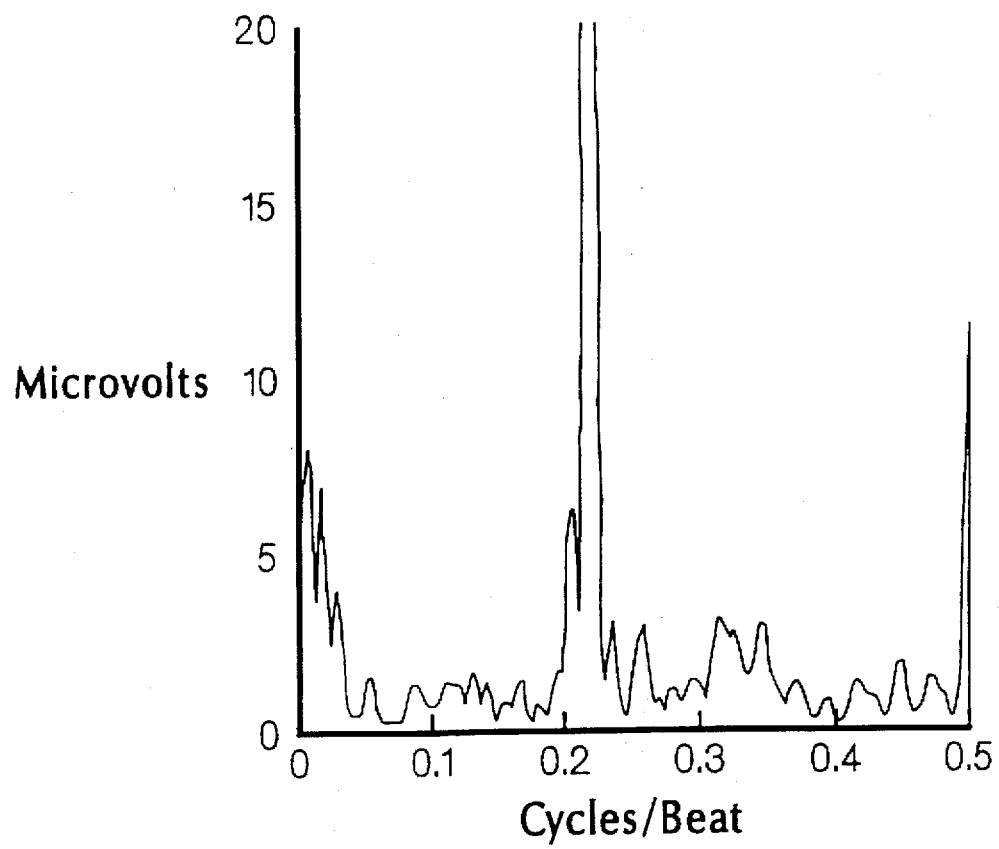
FIG. 30 is a plot of a power spectrum corresponding to the same data as in FIG. 7, in which signals from at least two electrodes were used to reduce noise in the data according to the invention.

FIG. 30 demonstrates the effectiveness of the use of multiple electrodes according to the method of the invention. This figure corresponds to the same patient data as FIG. 7. The patient had electrodes placed for the measurement of the standard vectorcardiographic X,Y and Z leads and in addition had electrodes placed for measurement of the standard 12 lead electrocardiogram. All the leads were used to compute according to the method of the invention a noise reduced estimate for each of the X,Y and Z leads. The estimates were then combined to compute the magnitude of the electrocardiographic vector (square root of the sum of the squared voltages in leads X, Y, and Z). This vector magnitude signal was then used to compute the power spectrum shown in FIG. 30. In FIG. 7, the vector magnitude signal was computed directly from X, Y and Z leads. Comparing the power spectra in FIGS. 7 and 30 one sees the tremendous noise reduction which has been achieved by the use of the multiple electrodes; in particular, the pedaling artifact is essentially eliminated.

IV. Real-Time Analysis

Figure 31:
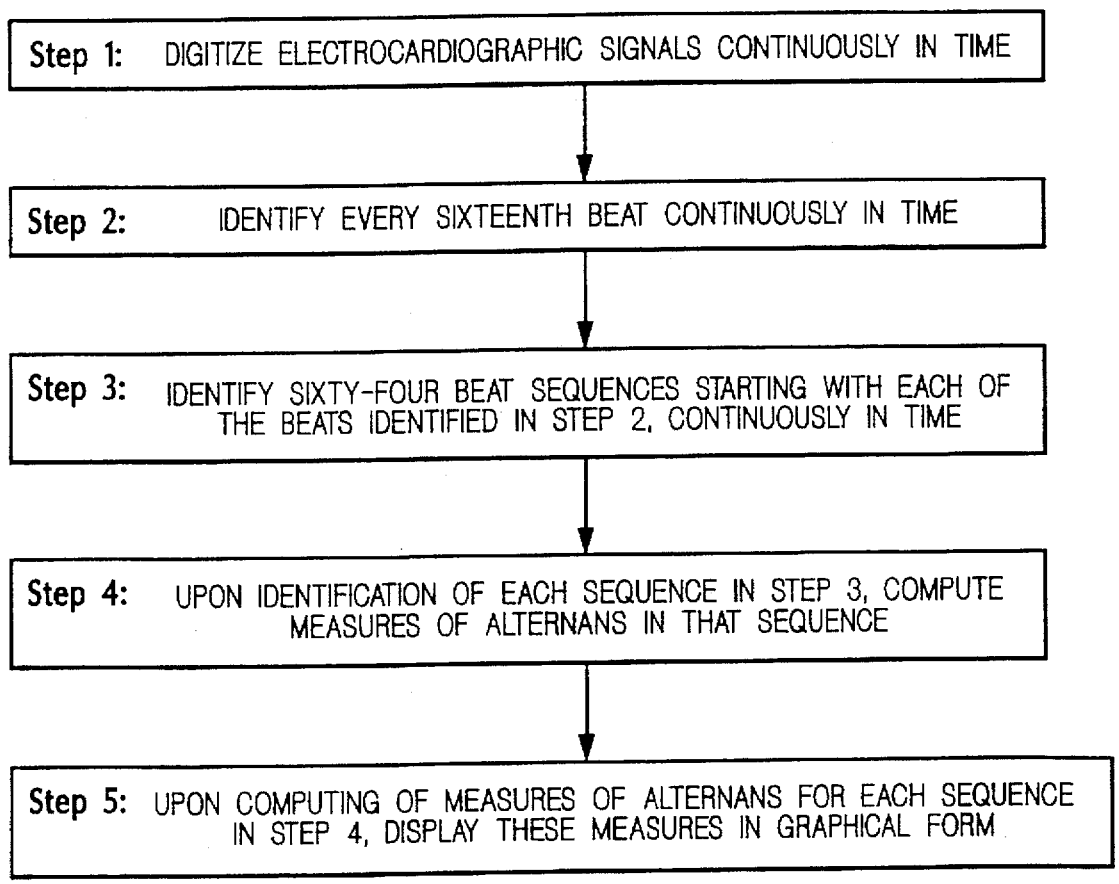
FIG. 31 is a flow diagram of steps for the real-time computation of alternans.

In one preferred embodiment of this invention, measures of alternans or other measures of the temporal pattern of waveform variability are computed and displayed in real-time as the data is accumulated. In a presently preferred embodiment, the analysis of the temporal pattern of cycle-to-cycle variability is performed on successive overlapping segments of data as the data is accumulated and the results of the analysis are displayed on each data segment as it is obtained (see FIG. 31).

Computing and displaying the results of the analysis in this way allows the operator to determine, while the data is being accumulated, whether sufficient data has been accumulated to determine whether a certain feature of waveform variability, such as alternans, is present, and to determine the magnitude of such variability as well as the level of statistical confidence of the measured variability. This enables the operator to determine in real-time whether sufficient data has been accumulated and the measurement can be stopped, or whether data collection needs to be continued, or whether the data is of deficient quality and the collection technique needs to be modified (e.g., one of the electrocardiogram electrodes is too noisy and needs to be replaced).

In order for a successful test for the presence of alternans be made in a patient, it is important that the operator have real-time or near real-time information available to be able to modify the parameters of the data recording while the data is being collected. Otherwise, a noisy electrode or prominent rhythmic artifact will often make the results of the test not interpretable. Such real-time or near real-time feedback enables the operator to modify the parameters of the data recording in order to make measurement of alternans a practical clinical test, particularly in the presence of physiologic stress.

In one preferred embodiment involving the use of bicycle, treadmill or stair stepping exercise as the means of physiologic stress, one may measure variations in the patient's actual heart rate in real-time, compute the desired target pedal or step rate range, and control the step or pedal rate to stay in this range (e.g., by use of a metronome).

V. Assessment of Statistical Significance of an Alternans Measurement

Cohen et al. (U.S. Pat. No. 4,802,491, which is herein incorporated by reference) report a method for analyzing the temporal pattern of variability in physiologic waveforms. In this method, a physiological signal is digitized and waveforms are identified using methods well known in the field. The waveforms are aligned using cross-correlation methods and a reference fiducial point is identified for each waveform. Each waveform may be labeled by an index i and sample points within a waveform are labeled by an index j representing the offset, j·Δ, from the fiducial point. Here Δ is the sampling interval. When multiple electrocardiographic signals are recorded simultaneously in the same subject, each lead may be similarly sampled, and sample points may be referenced. The sampled waveforms are analyzed to determine the level of alternans within a segment of the physiologic waveform. A power spectrum method is used to obtain three parameters: the energy (E) alternes at frequencies of 0.5 cycles/beat, the noise energy (E), and the standard deviation of the noise energy (S). These measures were combined to obtain an index of the level of alternans (e.g., the energy of the alternating component A=E-N and a measure $V_{ALT}$=the square root of A) or an index of the statistical significance of the alternans (K=A/S).

Figure 32:
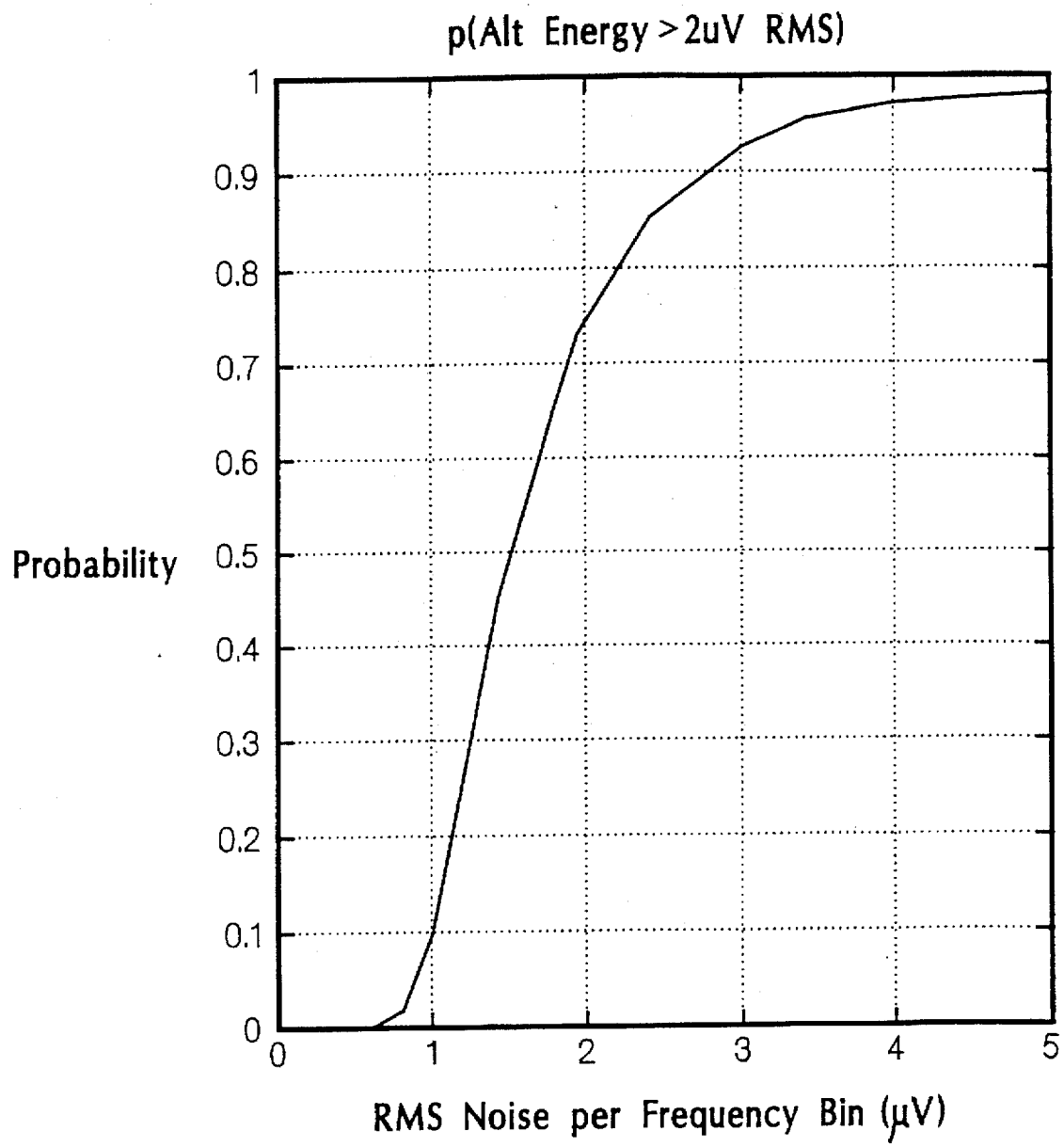
FIG. 32 is a plot of the probability that the alternans energy is greater than a reference revise level by $2_\mu V$ and that K is greater than 3 as a function of RMS noise per frequency bias.

FIG. 32 shows a simulation of the probability that the RMS alternans energy will, purely because of random white noise, exceed a clinically significant threshold of $2_\mu$RMS as a function of the noise level in the spectrum. (For this simulation, the alternans energy was measured using the method described in U.S. Pat. No. 4,802,491, with four independent samples in the T-wave; however, measurement by the method of complex demodulation, 3.g., as described in U.S. Pat. No. 5,148,812, which is herein incorporated by reference, would produce the same result. Note that the probability of a false positive detection of alternans greater than $2_\mu$V increases dramatically in the range of the $1_\mu$V to $3_\mu$V noise typically seen in this measurements.

Figure 33:
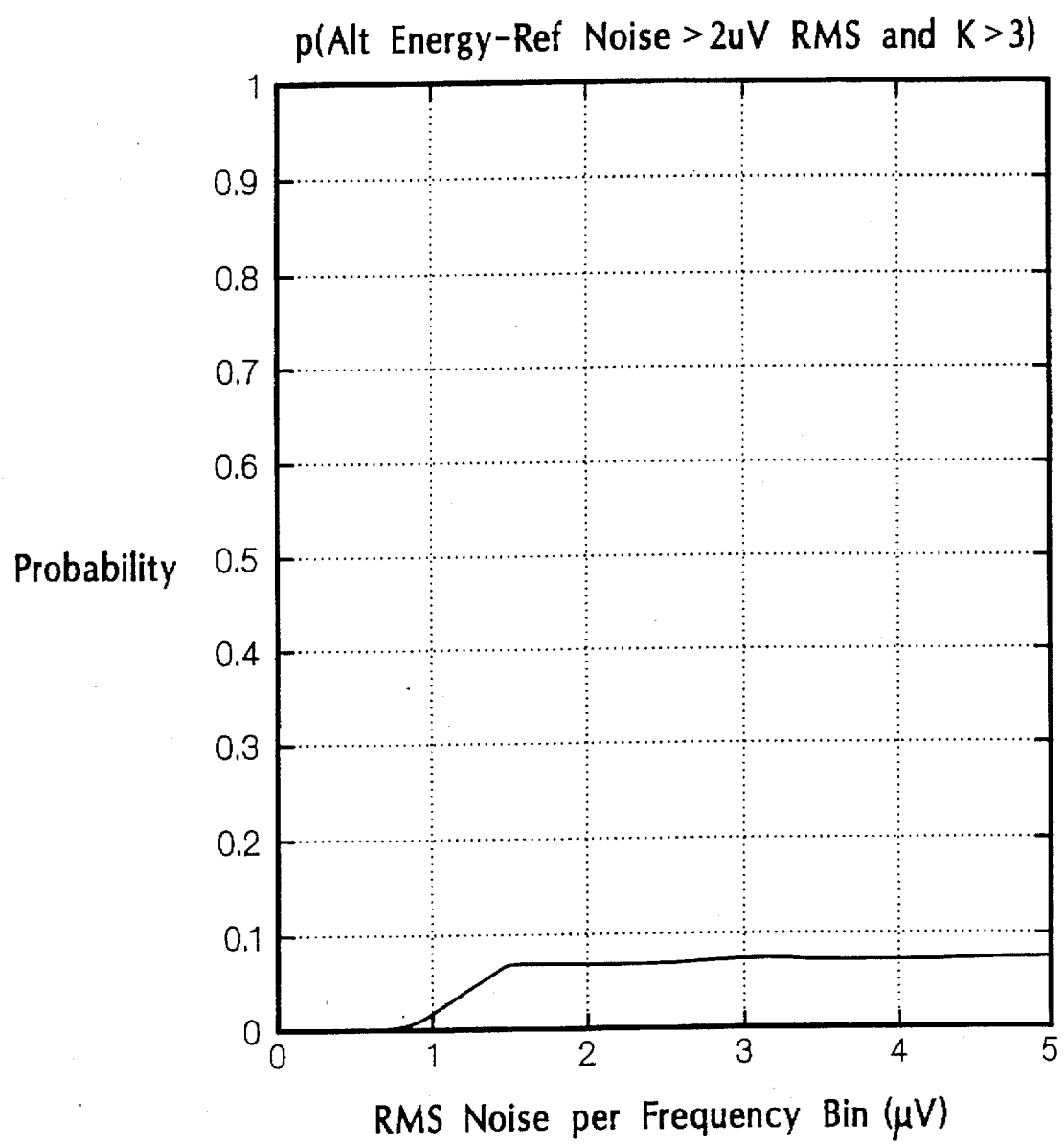
FIG. 33 is a plot of the probability that the alternans energy is greater than $2_\mu V$ RMS as a function of RMS noise per frequency bias.

FIG. 33 shows how using a test that combines (1) the difference between the alternans energy and the reference noise band must be $>2_\mu$V and requires that (2) the ratio of this difference to the standard deviation of the noise (called the K score) must be greater than 3 reduces this false positive error rate at all noise levels.

Thus, we have realized that it is desirable to enable one to determine with statistical confidence whether the level of alternans exceeds some upper threshold or conversely whether the level of alternans is less than some lower threshold. This may be of importance if, e.g., it is demonstrated that a subject whose level of alternans exceeds an upper threshold has a high risk of ventricular arrhythmias and a patient whose level of alternans is less than some lower threshold has a low risk of alternans. In this embodiment of the invention, indices are created which enable one to determine with a specified level of statistical certainty whether the alternans level exceeds an upper threshold or is less than some lower threshold (the upper and lower thresholds need not necessarily be different). The outcome of the alternans determination is thus positive (alternans level with statistical confidence exceeds upper threshold), negative (alternans level with statistical confidence is less than lower threshold), or indeterminate (neither positive or negative).

For example, a test that alternans with statistical confidence exceeds an upper threshold level is whether A exceeds the upper threshold by a multiple of S. An example of a test that alternans with statistical confidence is less than a lower threshold is whether A is less than the lower threshold by a multiple of S. In each case, the multiple of S used determines the level of statistical confidence. Values of the multiple between 1 and 5 are conveniently used. A negative test indicating that alternans is not present may also require the heart rate exceeds a minimum level.

In one preferred embodiment, assessment of the alternans pattern of cycle-to-cycle variation in physiologic waveform morphology is performed by comparing the level of the alternans in one portion of the electrocardiographic cycle to a noise level measured over a different portion of the electrocardiographic cycle. For example, the noise level may be computed over the PQ segment of the ECG. The PQ segment is a useful segment to analyze because normally there is little or no physiologic cardiac electrical activity during the PQ segment.

In another preferred embodiment, the significance of a measure of alternans (such as the energy of the alternating component minus the energy of the noise) is determined by determining whether the measure both exceeds an upper threshold and also, with a specified level of statistical certainty, the measure exceeds zero (for example by being larger than a multiple of the standard deviation of the energy of the noise). Conversely, the significance of the alternans measurement is determined based on whether the measure is less than a lower threshold. The significance of the measure of alternans being less than a lower level may depend on a minimum heart rate being achieved.

In another embodiment of this invention, the level of alternans (e.g., A) and the uncertainty of the alternans level (e.g., S) are computed for a measurement made in a certain subject. Then an empirical previously determined relationship between the level of alternans and probability of disease (e.g., risk of arrhythmias) is used (the relationship may incorporate the presence of known risk factors in the subject such as history of myocardial infarction and low ejection fraction). Probability of disease in this subject is then determined by integrating the probability distribution of the alternans level (defined in terms of the alternans level and uncertainty) over the empirical relationship between alternans level and risk of disease.

In one preferred embodiment, the alternans test is rejected as indeterminate if the noise exceeds a threshold value. In another preferred embodiment, a positive test requires that an index of the alternans level (such as $V_{ALT}$) exceeds a threshold value and that an index of statistical significance (such as K) exceeds a threshold value.

In one preferred embodiment, a test for susceptibility to ventricular arrhythmias is deemed positive if a significant level of alternans is measured during rest, during exercise which does not achieve the target heart rate, and/or during exercise where the target heart rate is reached. In this preferred embodiment for the test to be deemed negative the target heart rate must be achieved and the criteria for a negative test must be met at this heart rate, and significant alternans must not be present at rest or at levels of exercise where the target heart rate was not achieved.

One advantage of these improved methods for determining the statistical significance of the level of alternans, is that if they are determined during, or shortly following, the data collection process one may determine whether the amount of data collected is sufficient to make a statistically confident prediction of disease risk in an individual or whether additional or less noisy data need to be collected. If sufficient data has been collected to make a determination, the data collection process may be stopped.

Example: Statistical Significance in Multiple Physiologic Signals

Utilization of the vector magnitude ECG signal allows one to detect an alternating component of the ECG parallel to the direction of the instantaneous cardiac electrical vector. The vector magnitude is the square root of the sum of the squares of the voltage signals in three orthogonal vector leads as is obtained in the Frank electrocardiographic lead system. Alternating components of the ECG perpendicular to the instantaneous cardiac vector will not be reflected in the vector magnitude signal. Similarly, alternating components of the ECG perpendicular to the vectorial direction of any single ECG lead will not be reflected in that single ECG lead. Therefore, it is advantageous to measure alternans in multiple leads. However, the levels of noise may be different in different ECG leads, and therefore a high level of alternans in one lead may be insignificant in a lead with a high noise level and a lower level of alternans in another lead may be statistically significant in another lead with a lower noise level. In one preferred embodiment, the level of alternans (such as $V_{ALT}$) and a measure of the statistical significance of the alternans (such as K) is measured in multiple physiologic signals, for example in multiple ECG leads, and this information is combined to assess the level and presence of alternans in the subject.

For example, to assess alternans during exercise one could measure $V_{ALT}$ in the three orthogonal leads of the vectorcardiogram ($V_X$, $V_Y$, $V_Z$) also measure K in each lead. A positive alternans test would require that in one or more leads $V_{ALT}$ be greater than 1.9 microvolts and that K exceed 3 in the corresponding lead.

VI. Data Epoch Selection

As discussed above, a number of factors can interfere with the ability to reliably assess the level and significance of a pattern of cycle to cycle variation in physiologic waveforms, such as alternans, particularly during the application of a physiologic stress. Any measurement of alternans can be corrupted by noise which just happens to have significant energy at half the heart rate and thereby causes a false positive alternans result. Therefore, if one were to look for alternans continuously in a long data record one would be likely to eventually have a positive result irrespective of the patient's susceptibility to ventricular arrhythmias. Similarly, if one were to analyze only a single segment of data and that segment were to contain significant noise or premature beats or to be at too low a heart rate, then the alternans result may be falsely negative. Therefore a means needs to be developed to decide which segments are most suitable for analysis in order to provide the most accurate result. In one preferred embodiment, an epoch or epochs of data are chosen for analysis of the variation by considering measurements made in each epoch including one or more of the following: number or rate of premature or ectopic beats, the number of ectopic beats occurring in central portion of the epoch, a noise metric, a noise metric measured over a particular frequency band, a measure of the amplitude of the temporal pattern being assessed, a measure of the relative amplitudes of the temporal pattern being assessed and the noise metric, a measure of the statistical significance of a temporal pattern of cycle-to-cycle variation, the variability of some portion of the electrocardiographic signal, respiratory rate, heart rate, the patient's pedal or step rate, and/or interbeat interval variability.

As seen in FIG. 33, even when a combined test for level of alternans and for statistical significance is used as described herein, there is a significant probability of a false positive result each time an alternans measurement is made and this probability is a function of the noise level. As a result of this, the more times one looks for alternans, the more probable is a false positive result. If one were to continuously measure for the presence of alternans and to declare the test positive if a specific level of alternans is ever found, then the probability of a false positive result would approach 1.

To prevent this, it is important to minimize the number of independent times that one looks for alternans and to look only in data segments where the level of alternans is expected to be high and the level of interfering noise is low.

Thus, by considering such factors in epoch selection one can reduce the influence the factors which cause interference with the measurement of a particular pattern of cycle-to cycle variability, select the segments where the amplitude of the temporal pattern being assessed is largest and most significant, and select the segments which are most likely to result in the temporal pattern of variability being assessed being detected. For example, epochs with few or no abnormal premature beats or none near the center of the epoch will suffer least from the effects of phase resetting. Epochs with a low level of noise are most likely to reveal the temporal pattern of variability being assessed. This noise can be measured, for example, by considering the variability in the PQ segment of the electrocardiogram; the PQ segment is a useful segment to analyze because normally there is little or no physiologic cardiac electrical activity during the PQ segment. The noise can also be measured in one or more reference frequency bands (see, e.g., Cohen et al., cited above).

Figure 34:
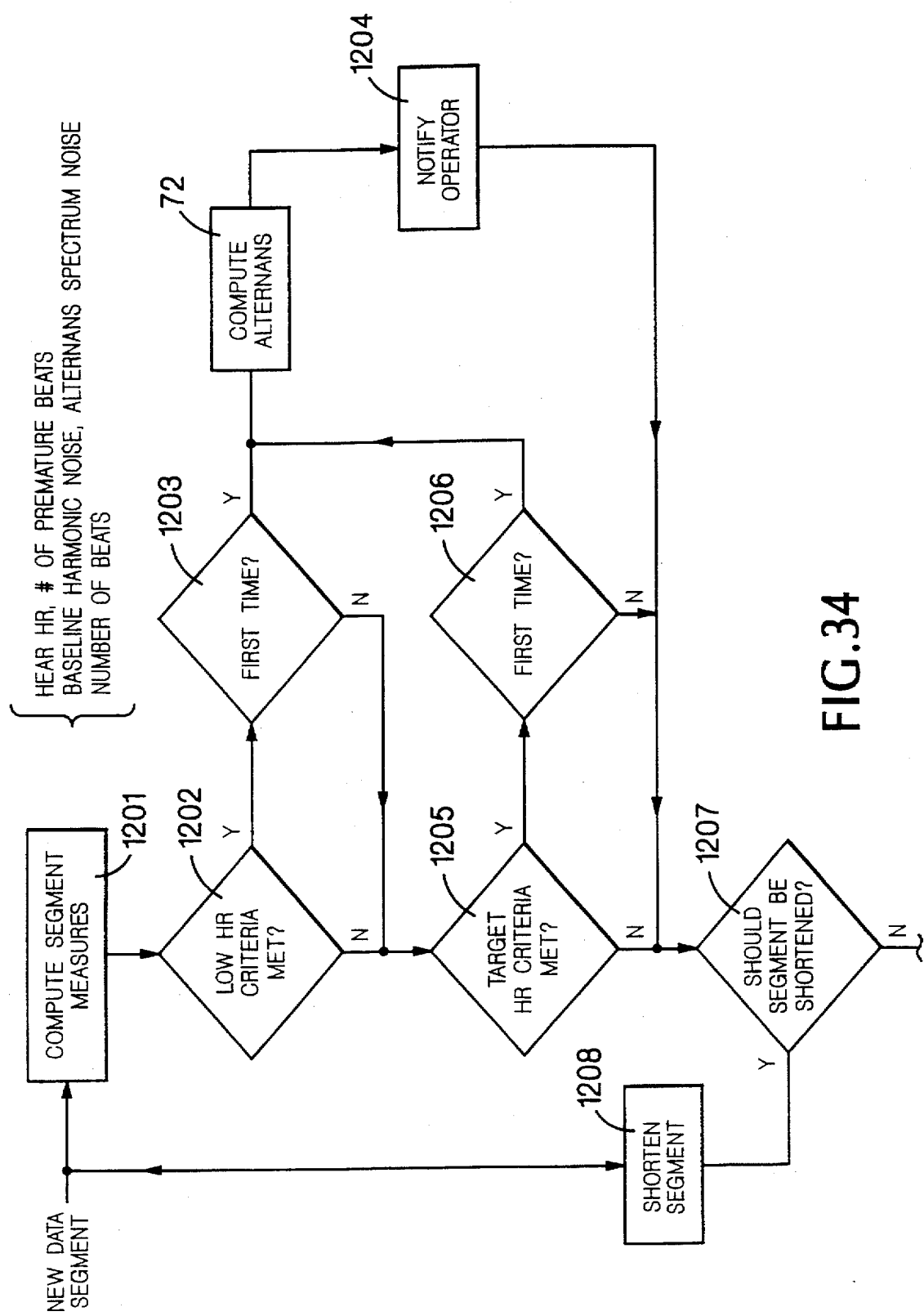
FIGS. 34 and 34A show a flow diagram of steps for selecting epochs from a measured data signal.
Figure 34A:
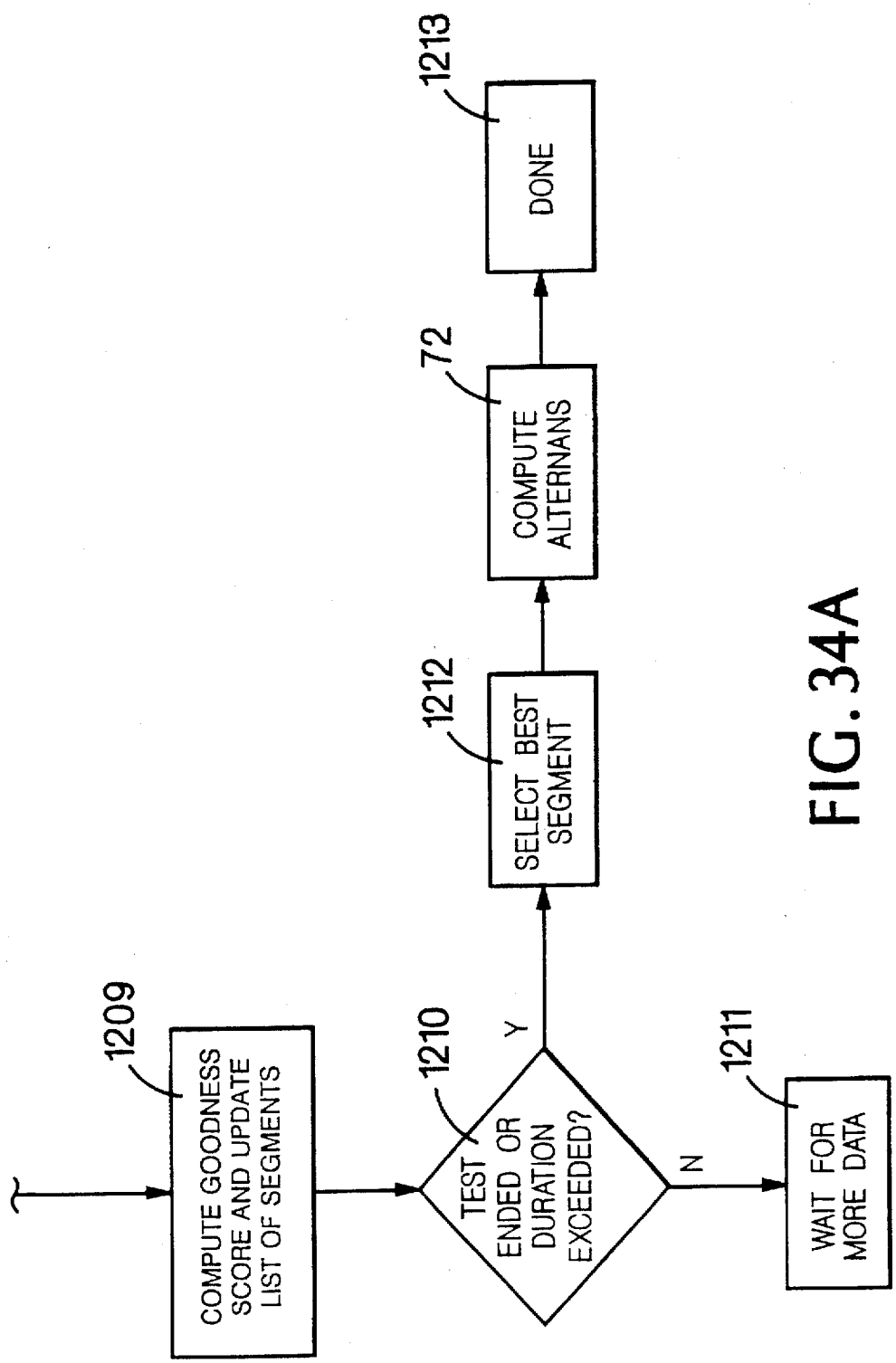

Referring to FIGS. 34 and 34A, in a presently preferred epoch selection scheme, the segment finder maintains a list of segments ranked by their "goodness" which ranges from 0 to 10. In step 1201 a candidate segment is taken from the beat matrix 70 as the next eligible segment from a list of beats. Segments are allowed to begin only on beats whose number is a multiple of an increment of 8 beats. The segment is expected to be 128 beats long; however, if fewer than 128 beats are available, the shorter segment is used if it meets the minimum segment length requirements described in step 1207 below. Since the segment increment of 8 is much smaller than the target number of beats, the segment under consideration overlaps with previous segments. The preferred embodiment limits the possible lengths and origins of the segments for computational simplicity. Other embodiments may implement methods that consider a broader range of segment origins and lengths.

Step 1201 computes the metrics used to create the "goodness" score for the segment under consideration. These metrics include the mean heart rate, the prematurity metrics, noise metrics, and the number of beats. The noise metrics include the baseline harmonic noise and alternans spectrum reference noise. The baseline harmonic noise is computed from the power of the spectrum of PQ levels at 0.167 and 0.25 cycles/beat. These noise frequencies are of interest because their 3rd and 2nd harmonics, respectively, fall at the alternans frequency of 0.5 cycles/beat. The alternans spectrum reference noise band is computed to approximate the measure N as defined in the introduction. The alternans spectrum reference noise power is also computed from noise-optimized ECG leads. The prematurity metrics include the total number of premature and postmature beats in the entire segment and in the middle half of the segment. Premature beats can reset the alternans, causing the measured alternans level to be lower. The closer that the premature beats fall to the center of the segment, the greater the potential cancellation of the alternans signal due to phase resetting.

Alternate embodiments may use a variety of other metrics derived from or related to the input signals. The metrics may include the total heart rate variability or heart rate variability in specific frequency bands, or other measures related to the alternans modulation. The metrics may derived from to respiration and motion measures, where the measures are estimated from the ECG or measured by some other means. The metrics may include a host of noise measures derived from single beats or beats taken in groups.

Step 1202 tests whether the segment meets the primary criteria for a low heart rate. The low HR primary criteria are: a heart rate of 90–100 beats per minute, no premature beats, baseline harmonic noise less than $2_\mu V$, reference band noise less than 1.2 µV, and at least 100 beats. The first time that the low heart rate criteria are met, the alternans result for that segment is computed as specified in step 72 and the operator is notified of the result in step 1204. Step 1205 tests whether the segment meets the primary criteria for the target heart rate. These criteria are the same as for a low heart rate segment, except that the heart rate range must be 100–120 beats per minute. The first time the target heart rate criteria are met in step 1206, the alternans result for that segment is computed as specified in step 72 and the operator is notified of the result in step 1204.

Step 1207 decides whether a shortened segment should be considered. A shorter segment is created for consideration if the target heart rate criteria have not been met and if the resulting segment is at least 64 beats long. The segment is shortened in step 1208 by removing from the end of the segment the number of beats specified by the increment value and the segment is then returned to step 1201. Other embodiments remove beats based on the significance of the change in one or more of the metrics occurring at the specific beats.

In step 1209 the goodness measure of the segment is computed using a piecewise linear function of the measures. Step 1210 checks to see if there is no more ECG data available, or if the test should be terminated because a pre-specified duration has been exceeded. If the test is to continue, the segment finder waits at step 1211. If the test is completed, the segment with the greatest "goodness" is selected from the segment list in step 1212 and supplied to step 72 to compute the alternans measures. The resulting segment and alternans information is returned in step 1213.

Other embodiments may choose to consider several segments simultaneously. The segments may be handled separately, with separate metrics and alternans results computed for each segment and combined by a weighted average, or the segments may be joined into one longer segment. One possible embodiment is to join segments of beats that fall between premature beats. The segments must be joined with proper consideration to whether the first beat in each segment is a even or odd number of beats after the premature beat.

Another embodiment further reduces the false positive rate by analyzing multiple independent epochs and analyzing the consistency of the result; i.e., requiring that the test be positive in more than one epoch. This resultant false positive rate will be significantly reduced.

Figure 35:
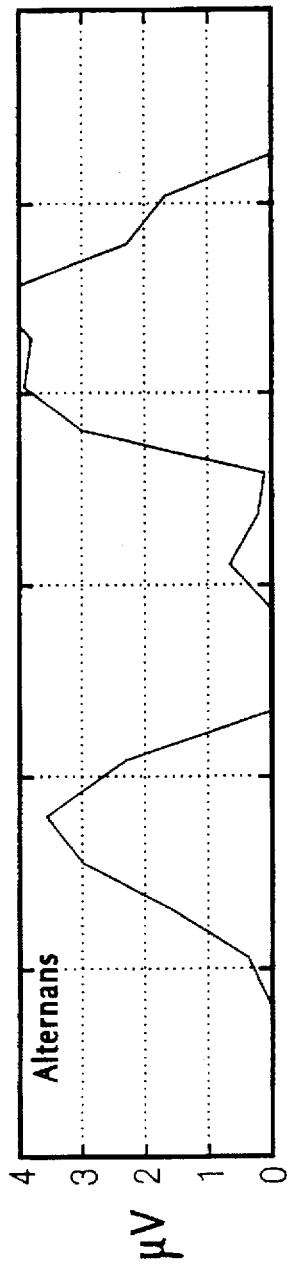
FIGS. 35–35D are respective plots over time of the level of alternans, a flag for ectopic beats, the heart rate the level of overall noise, and the level of noise and respiration occurring at ¼ and ⅙ of the heart rate.
Figure 35A:
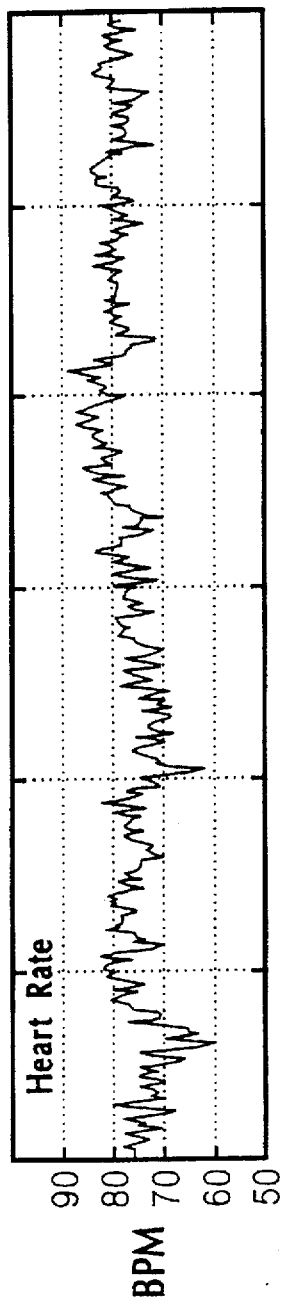
Figure 35B:
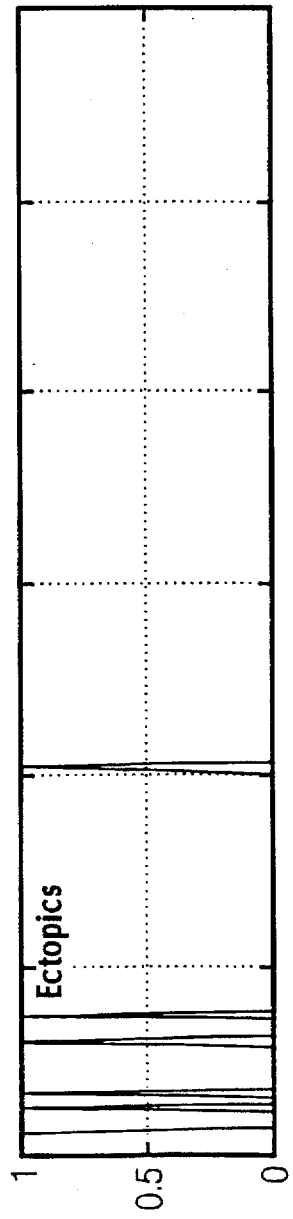
Figure 35C:
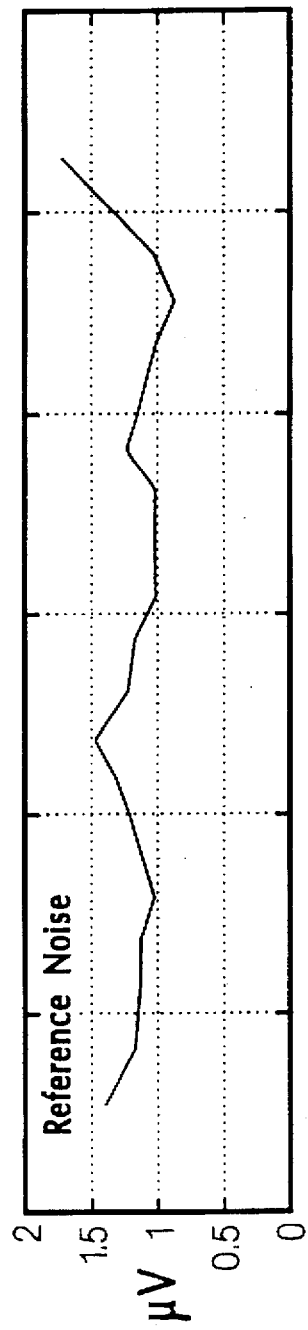
Figure 35D:
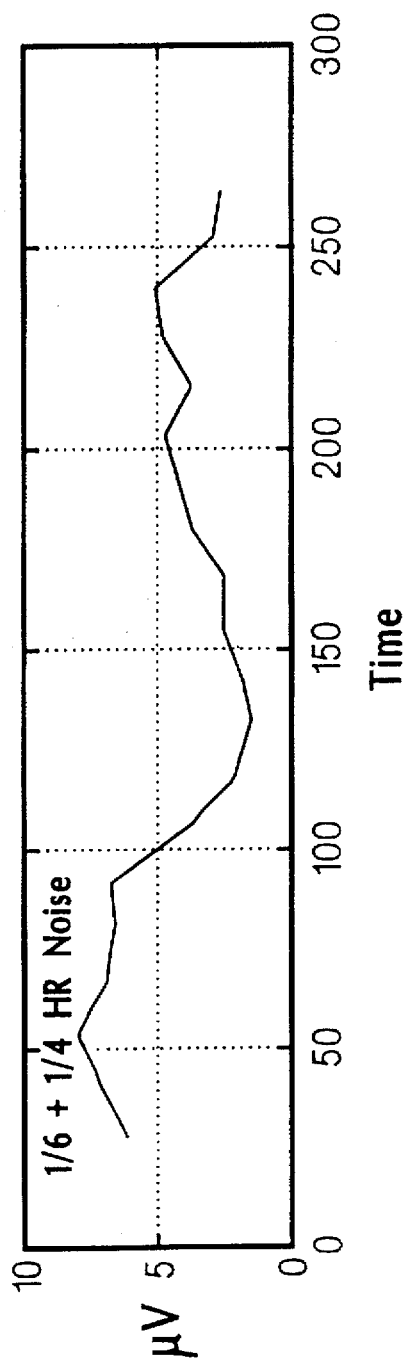

Another embodiment involves outputting the variables used in the epoch selection process and, in effect, allow the operator to select the appropriate epoch and analyze the consistency of the result. FIGS. 35–35D show a graph which indicates over time the level of alternans, a flag for ectopic beats, the heart rate the level of overall noise, and the level of noise and respiration occurring at ¼ and ⅙ of the heart rate. From such an output, the operator can look for appropriate epochs, selectively ignore epochs where there is a high level of interfering noise and determine the consistency of result.

An alternative approach to reducing the effects of respiratory activity on the assessment of an alternans pattern of cycle-to-cycle variability in physiologic waveforms involves monitoring respiration and causing the patient to alter his respiratory rate when this rate is at a sub-multiple of the heart rate. A further approach to reducing the effects of respiratory activity on the assessment of an alternans pattern of cycle-to-cycle variability in physiologic waveforms involves measuring and excluding from the analysis those sections of data which correspond to periods during which respiration is at an even sub-multiple (such as one quarter or one sixth) of the heart rate or where the energy of all potentially interfering signals such as respiration is high at such sub-multiple frequencies.

It should be understood that the concept of epoch selection includes any of a variety of possible means of selecting or emphasizing portions of the recorded data. For example, rather than selecting one or more specific epochs for analysis, the alternans analysis might be performed over the entire data record and a weighing function used to emphasize certain portions of the data based on variables such as mean heart rate, frequency of premature or other abnormal beats, noise, etc. Or, for example, one might display in graphical form variables such as alternans level, noise level, measures of statistical significance of alternans, mean heart rate etc., over a long data epoch so that the operator may choose the portion of the data which is most significant for the interpretation of the alternans measurement.

VII. Applications

It may be advantageous to combine alternans measurement with other diagnostic tests particularly those used for cardiovascular diagnostics. The combinations of alternans measurement with these other tests provides unexpected advantages in terms of diagnostic capability and in terms of dual use and cost effectiveness of diagnostic equipment.

A. Combination of An Alternans Test System with a Standard Exercise Stress Test System The techniques described above allow an alternans test system to be combined with an exercise stress test system. This combination is particularly advantageous because exercise stress tests, which are given to measure cardiac ischemia caused by the presence of coronary artery disease, are often given to the same patients in whom one would like to measure alternans to determine the risk of ventricular arrhythmia's. Furthermore, in some patients where one would like to make both tests, such as in patients who have recently suffered a heart attack, there is some risk associated with exercise and it is advantageous not to have to exercise the patient twice.

In another preferred embodiment, one analyzes the temporal pattern of cycle-to-cycle variability in a physiologic waveform both at rest and during physiologic stress. The temporal pattern of cycle-to-cycle variability in waveform morphology may or may not be present in any patient at rest but there may also may be less physiologic noise as compared with the data collected during physiologic stress. By combining analyses of data at rest and during physiologic stress a more reliable assessment of the presence and magnitude of the temporal pattern of cycle-to-cycle variability in physiologic waveforms may be obtained. Furthermore, some patients cannot exercise sufficiently to achieve the minimum target heart rate of approximately 100 beats per minute. A measurement made at rest and during reduced levels of exercise which results in a significant level of alternans, would indicate that the patient may be at risk of ventricular arrhythmias. In the absence of such measurements no alternans based information on the patient's risk would be available. Of course, under circumstances where the patient cannot achieve the minimum target heart rate one could not definitively determine that the patient does not have inducible alternans.

Data may be collected during a standard bicycle exercise stress test used for other purposes such as the detection of coronary artery disease, and the analysis process analyzes the data which falls within the specified limits of heart rate and pedal rate if the apparatus has means to measure pedal rate as well as heart rate. Data may be collected during a standard bicycle, treadmill, stair stepping or other exercise stress test conducted for purposes other than assessment of alternans, for example for the purpose of detecting coronary artery disease, and the data segments analyzed for alternans are those in which the step and target heart rates fall within the target ranges.

Standard exercise stress tests generally involve multiple stages described as the Rest Stage, Exercise Stages 1 through N, and the Recovery Stage. Each of the stages has particular advantages for the measurement of alternans. The Rest Stage has the advantage of low noise but, because the heart rate is not elevated, the incidence of alternans during rest is low. Therefore a positive alternans measurement during rest can be considered a positive result, but the absence of alternans cannot be considered a negative result. However, since some percentage of patients will not be able to achieve a sufficiently high heart rate during exercise and in others the level of premature beats or artifact will make the measurement during exercise impossible, it is worthwhile to measure during rest.

The Recovery Stage which occurs after the cessation of exercise has some advantages as well. The heart rate will still be elevated but the artifact level due to exercise will be reduced. Unfortunately, the heart rate will be falling rapidly and the mean heart rate level for the segment of data may be too low to insure a negative test. The preferred embodiment uses measurements during all three periods (Rest, Exercise and Recovery) and may include pharmacological stress. The test is considered positive and can be terminated if there was a statistical level of alternans in any lead at rest, during exercise or during recovery. The test is considered negative only if there was an acceptable epoch selected with a mean heart rate over the target (generally 100 beats per minute) and the noise measures were low enough to have a statistically significant negative result. Tests which are neither positive or negative are indeterminate and call for further testing. This can mean the addition of a pharmacological stress agent to help reach the target heart rate or the addition of a final exercise stage using a different form of exercise which may cause lower levels of artifact (such as adding a bicycle stage after a treadmill test).

Figure 36:
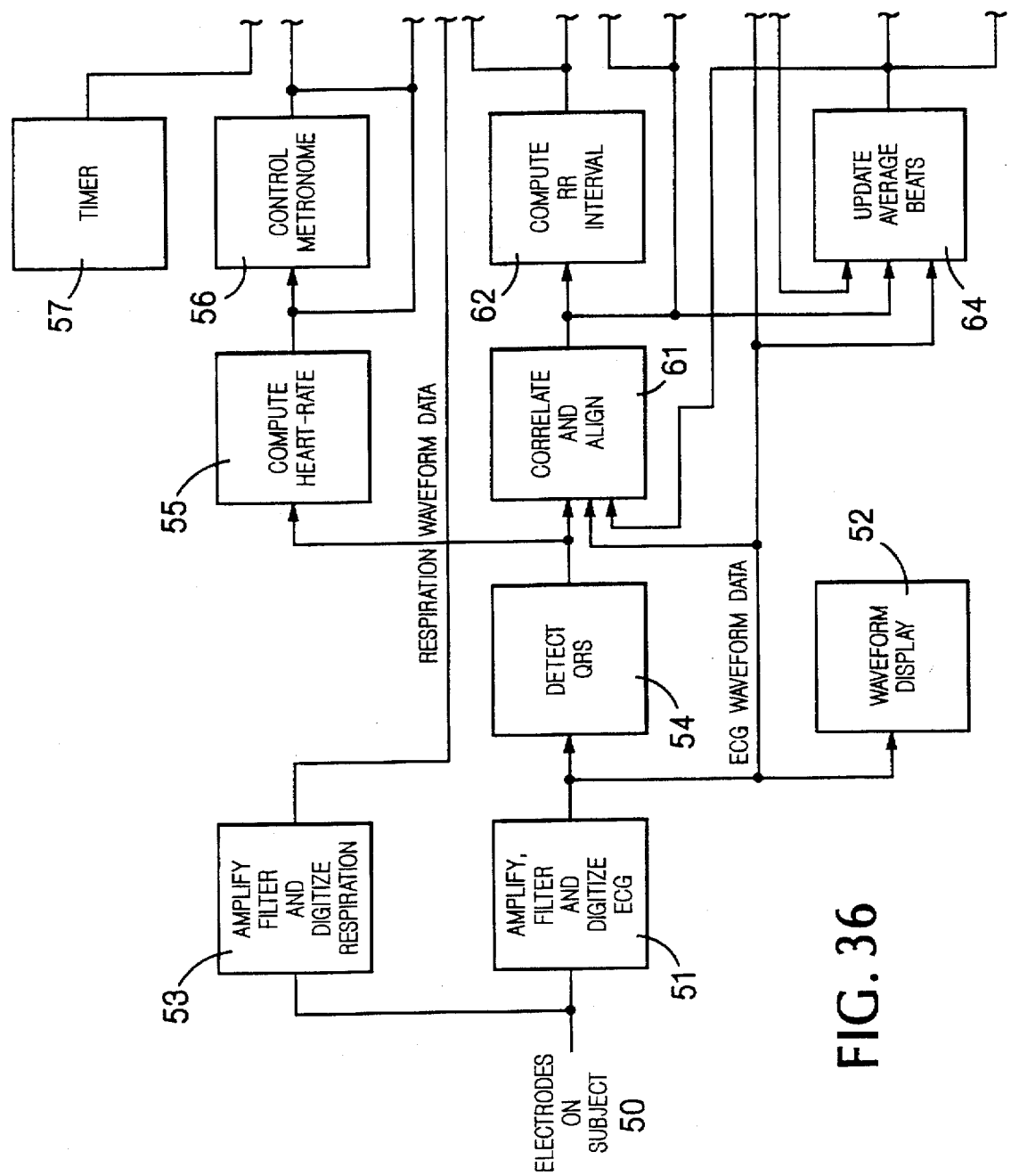
FIGS. 36 and 36A show a block diagram of a combined exercise stress test and alternans measurement system.
Figure 36A:
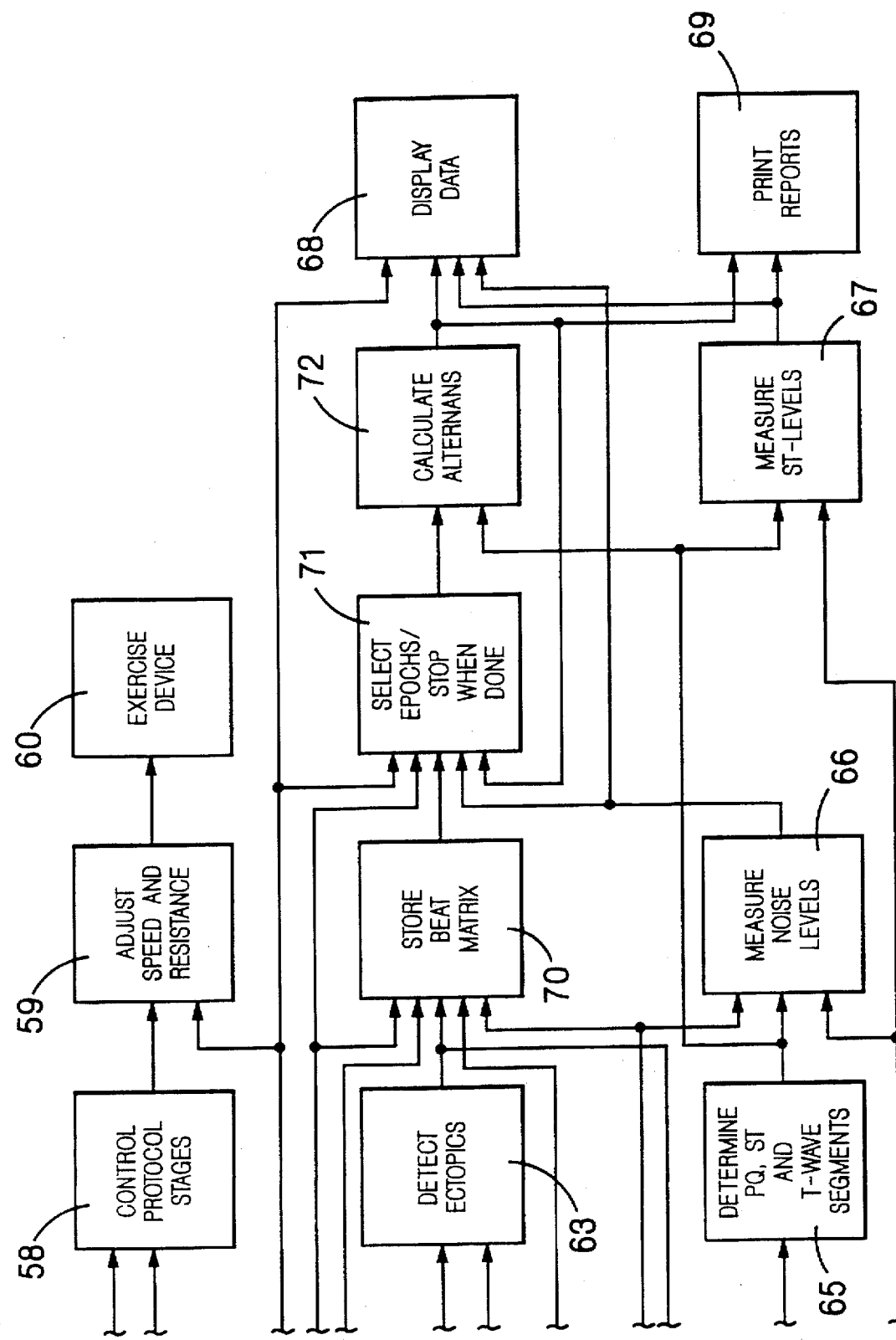

FIGS. 36 and 36A show a block diagram for a combined Exercise Stress Test and Alternans System. The subject has ECG electrodes 50 applied at the standard positions used for collecting standard 12 lead ECG data as well as at the positions used for Frank X, Y, Z lead ECG data. The ECG waveforms from the electrodes are amplified, filtered at 0.05 to 150 Hertz and digitized at 1000 Hertz using standard ECG amplifier, bandpass filter and 12 bit A to D converter techniques 51 and the ECG waveform data is displayed 52 for the operator. At the same time a respiration waveform is determined from two of the electrodes on the right and left side of the chest using impedance plethysmography techniques well known in the art and also amplified, filtered at 0.05 to 150 Hertz and digitized (53) at 1000 Hertz.

QRS complexes are detected (54) from the digitized ECG waveform data using standard techniques well known in the art. The time of the detected QRS complexes is used to compute heart rate 55 using standard techniques and this heart rate is used to control a metronome 56 which sounds at a rate of 1/3 or 2/3 (operator selected) of the computed heart rate in the manner described earlier. This metronome is used by the subject to maintain a step rate or pedal rate on the treadmill or bicycle exercise device 60 so that the rhythmic artifact from the exercise does not interfere with the alternans measurement.

At the same time a timer 57 is used to control (58) the various stages of standard exercise protocols. These protocols generally call for a Rest Stage followed by timed Exercise Stages, often three minutes each in length where the level of exercise is increased at each stage. This increase is effected by adjusting (59) the speed and incline of a treadmill or the resistance of the bicycle exercise device (60). In addition, the protocol control function (58) continually monitors the computed heart rate and prompts the operator to terminate the exercise when a target heart rate specific to the type of protocol is achieved. When exercise is terminated for this or other reason (such as fatigue of the patient, chest pain, or excessive ST segment level depression), the protocol control function (58) starts the Recovery Stage, where the patient is allowed to rest while continually being monitored by the system.

The above paragraph describes the protocol control function where it is desired to measure alternans during a standard exercise protocol designed for the detection of coronary artery disease. However, in some cases it may be desired only to measure alternans in which case a protocol optimized for alternans measurement is used. This protocol calls for a Rest Stage followed by a level of exercise which is adjusted (59) based upon the computed heart rate (from 55) to cause the subject's heart rate to achieve and maintain an optimal level for alternans measurement (generally 100 to 120 beats per minute). This level is maintained until sufficient data is collected for a statistically significant alternans computation to be completed in accordance with the teachings of this invention.

While the subject is progressing through the stages of the exercise protocol the system measures alternans and computes ST segment levels as described below.

The detected QRS complexes (from 54) are cross correlated (61) with average beat templates (produced by 56) and aligned with these templates at the time of the point of maximum correlation to produce an adjusted time of the QRS which is more stabile and resistant to noise. This adjusted time of the QRS is used to compute the R to R (i.e., RR) intervals (62). These RR intervals and the correlation coefficients (from 61) are used to detect ectopic beats (63). An ectopic beat is defined here as one which has a correlation coefficient with the average beat template of less than 0.9 or whose previous RR interval is less than 90% of an 8-beat running average RR interval.

The average beat templates (one template for each ECG lead) are updated (64) by taking the ECG waveform data surrounding the detected and aligned QRS complex and computing a point by point 8 beat running average of ECG waveform data with the stored average beat templates. This function (62) also uses ectopic detection (63) to reject and not average in to the average beat templates any beat determined to be ectopic.

The average beat templates are analyzed (65) to determine the PQ segment, the junction point, the ST-measurement point and the ST-T wave segment using techniques described below. The PQ segment is determined by computing the Absolute Value Vector Velocity (ASVV) from the sum of the absolute value of the derivative of the X lead, the Y lead and the Z lead and looking for a minimum in a 100 millisecond region preceding the QRS complex. The J point is determined as the point after the QRS where the ASW falls to 7.5% of its QRS peak. The ST measurement point is defined as 80 milliseconds past the J point. The ST-T wave segment is defined for the purposes here as extending from 60 milliseconds past the J point to 20 milliseconds past the point where the ASVV false to 7.5% of its peak in the ST-T wave segment.

The segments determined (by 65) are used to measure noise levels 66 during the PQ and ST-T wave segments by computing the point by point standard deviation of the ECG waveform data for each lead from the means obtained from the average beat templates over the points in these two segments. These measures are displayed for each lead (68) in a bar graph format so that the operator can see if the noise level is too high for the measurement of alternans and take appropriate action such as improving electrode contact.

The ST measurement point is used to measure the ST-Levels for each ECG lead (67). These levels constitute the primary output from a standard stress test and are displayed to the operator (68) and printed in reports 69.

At the same time the times of the aligned QRS complexes are used to trigger the storage of another beat in the beat matrix (70). This matrix contains multiple rows of one beat each aligned on the QRS complexes as described in U.S. Pat. No. 4,802,491 cited above. However, instead of just storing the vector magnitude waveform for each beat, all of the leads are stored along with simultaneous respiration data (from 53), the previous RR interval (from 62) and the results of the ectopic detection (from 63). In addition, in recognition that the alternans energy is generally low frequency in nature and to save storage, the ECG waveform data is digitally lowpass filtered at 25 Hertz and subsampled at 50 Hertz before storage in the beat matrix.

Figure 37:
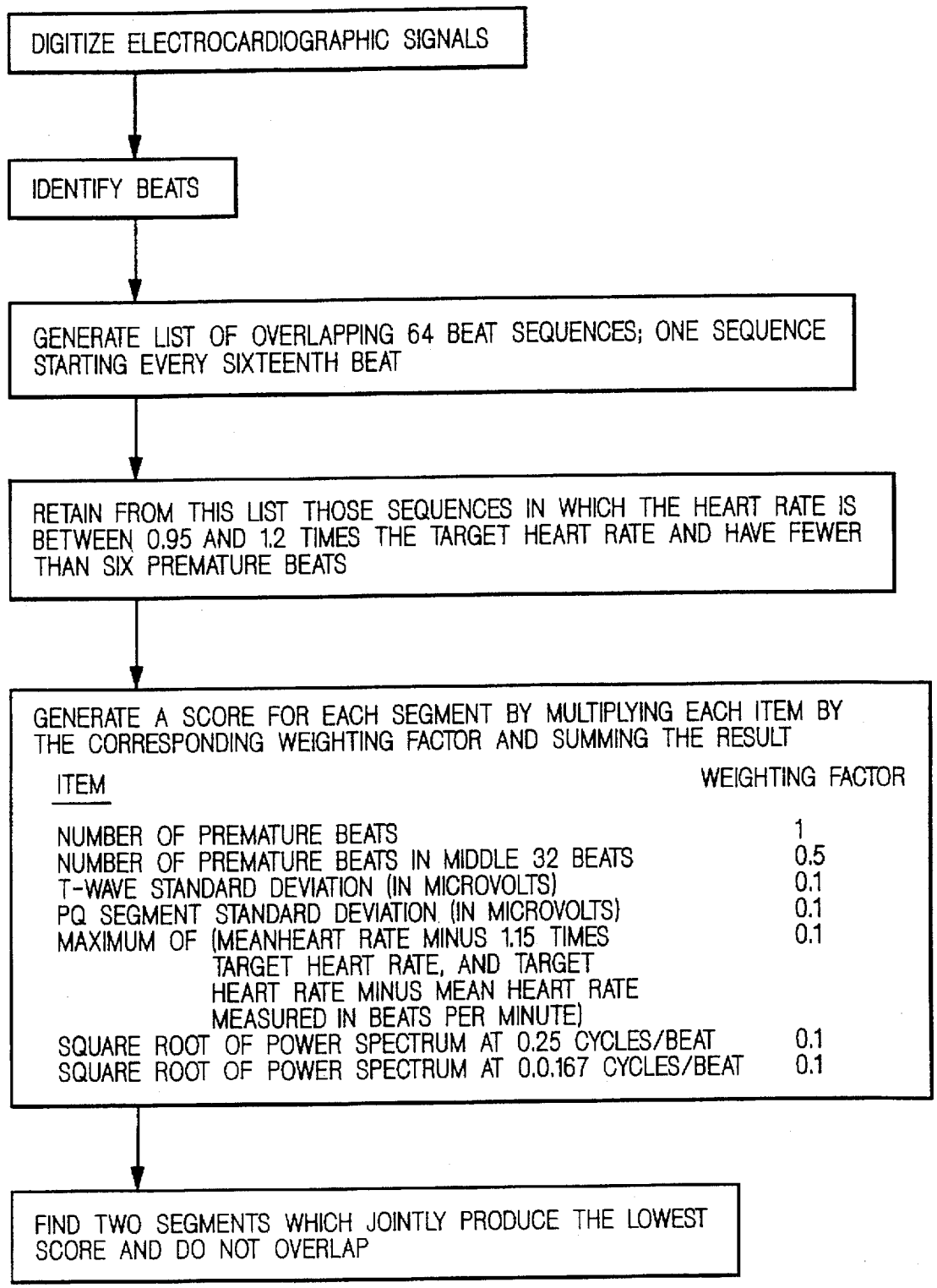
FIG. 37 is a flow diagram of a method for selecting one or more epochs from a measured signal.

The Select Epochs function (71) uses the heart rate (from 55), the number of ectopic (from 63), and the noise levels (from 66) to determine appropriate segments for analysis. This function is described in the flow chart in FIG. 37 and in detail in the earlier Signal Processing section. The Select Epochs function also uses the alternans measurements (from 72) to determine when there has been a statistically significant alternans result and alternans processing can stop.

The selected epochs are passed to the Calculate Alternans function (72) which calculates the alternans measurements in real time, determines their significance and displays them to the operator (68) and for print-out (69).

Figure 38:
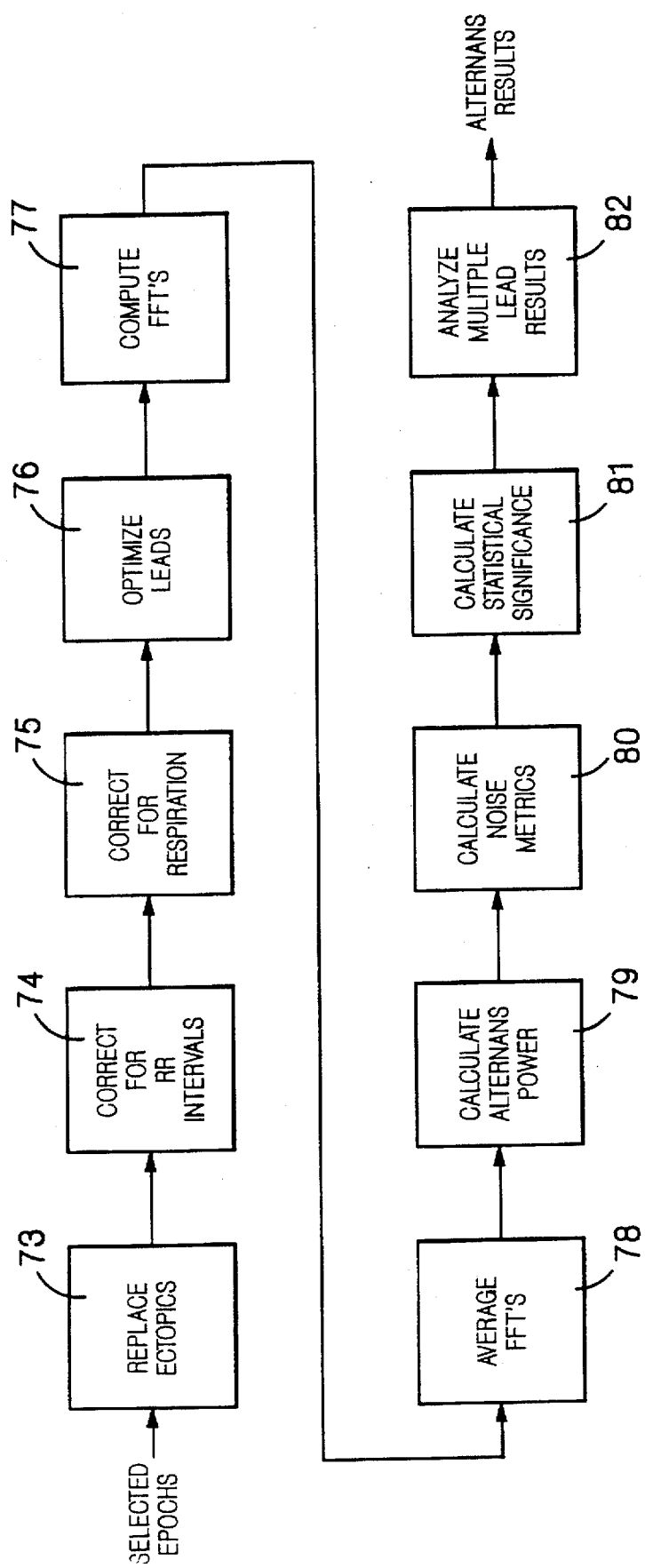
FIG. 38 is the block diagram for the Calculate Alternans process of the system in FIG. 19.

The Calculate Alternans function is described in more detail in FIG. 38. First the ectopic detection data is used to replace any ectopic beats with the mean computed over the selected epoch. Then (74) the data in each lead is corrected for RR interval variations over the ST-T wave segments using the techniques described earlier. Then the data is corrected for respiration effects (75). Typically, these two steps are performed simultaneously. Then the optimum (lowest noise) X, Y, and Z leads are computed (76) from the multi-lead ECG data using the methods described in U.S. application Ser. No. 08/339,032, filed Nov. 14, 1994, cited earlier. In addition, an optimized V lead, similar to V4 is computed using the same techniques. Then fast Fourier transform spectra (FFT's) are computed (77) for each epoch, for each of X, Y, Z, and V leads and for each point in the ST-T wave segments and these spectra are averaged (78) to form a composite spectra for each of X, Y, Z and V leads. Then the alternans power is computed (79) from the last point in the averaged spectra. The noise mean and standard deviations for the spectra are computed from an adjacent noise band covering as described in Smith et al, 1988, cited earlier. Then the statistical significance of the alternans voltage is calculated (81) as described earlier in the Signal Processing section. Finally, the results in the multiple leads are analyzed in (82) to find the highest level of alternans with a specified level of statistical significance and this result is then output for display and printing.

C. Combination of An Alternans Test System with a Standard ECG Cart

In a preferred embodiment of this invention, a system for measuring alternans is combined with a standard ECG cart. This is a particularly favored combination because it enables one to combine measurement of alternans which is an accurate predictor of the risk of ventricular arrhythmias, with other diagnostic tests that can be performed with an ECG cart. The standard ECG cart is usually used to record and analyze the standard 12 lead electrocardiogram. This test provides a wide range of diagnostic information on the electrical conduction pattern in the heart. The standard ECG, however, provides little information on the risk of future life-threatening ventricular arrhythmias. Some ECG carts have the capability to compute the Signal Average Electrocardiogram (SAECG). The SAECG is obtained by averaging many repetitive ECG waveforms. It has been shown that 'late potentials' which occur at the end of the QRS complex and may be detected in the SAECG may provide some information on the risk of ventricular arrhythmias. We have found that alternans is a much more accurate predictor of ventricular arrhythmias than the SAECG, however, combining SAECG and alternans measurements may provide even better accuracy than either test alone. Further, an ECG cart may be adapted to measure beat-to-beat variability in the QRS complex in a multiplicity of leads. Increased QRS variance (see U.S. Pat. No. 5,188,116) has been shown to be an accurate indicator of the presence of coronary artery disease even when the measurement is made without the use of physiologic stress. Further, an ECG cart may be adapted to measure other physiologic signals and perform Physiologic System Identification (see Cohen et al., U.S. Pat. No. 4,930,517) to accurately assess autonomic nervous system activity and cardiovascular reflexes. Physiologic System Identification involves the mathematic analysis of the coupling between fluctuations in different physiologic signals to create an individualized physiologic model of closed loop physiologic function. Thus, by combining an ECG cart with an alternans system, a multiplicity of very important and complementary diagnostic tests can be performed with a single system.

It is further advantageous to combine the ECG recording device with an alternans measurement system because much of the same hardware can be used for both systems. For example, the most recording electrodes can be used for both standard ECG analysis as well as alternans recording; the same ECG amplifier and computer system can be used both for the standard ECG analysis and for the alternans measurement. Furthermore, many of the signal processing features used for alternans analysis can also be applied to the other diagnostic functions of the ECG cart (standard 12 lead ECG measurement and analysis, SAECG and/or QRS variance analysis) for example, detection of abnormal beats, adjustment of ECG waveforms to compensate for the effects of interfering signals, epoch selection, noise reduction, etc.

Figure 39:
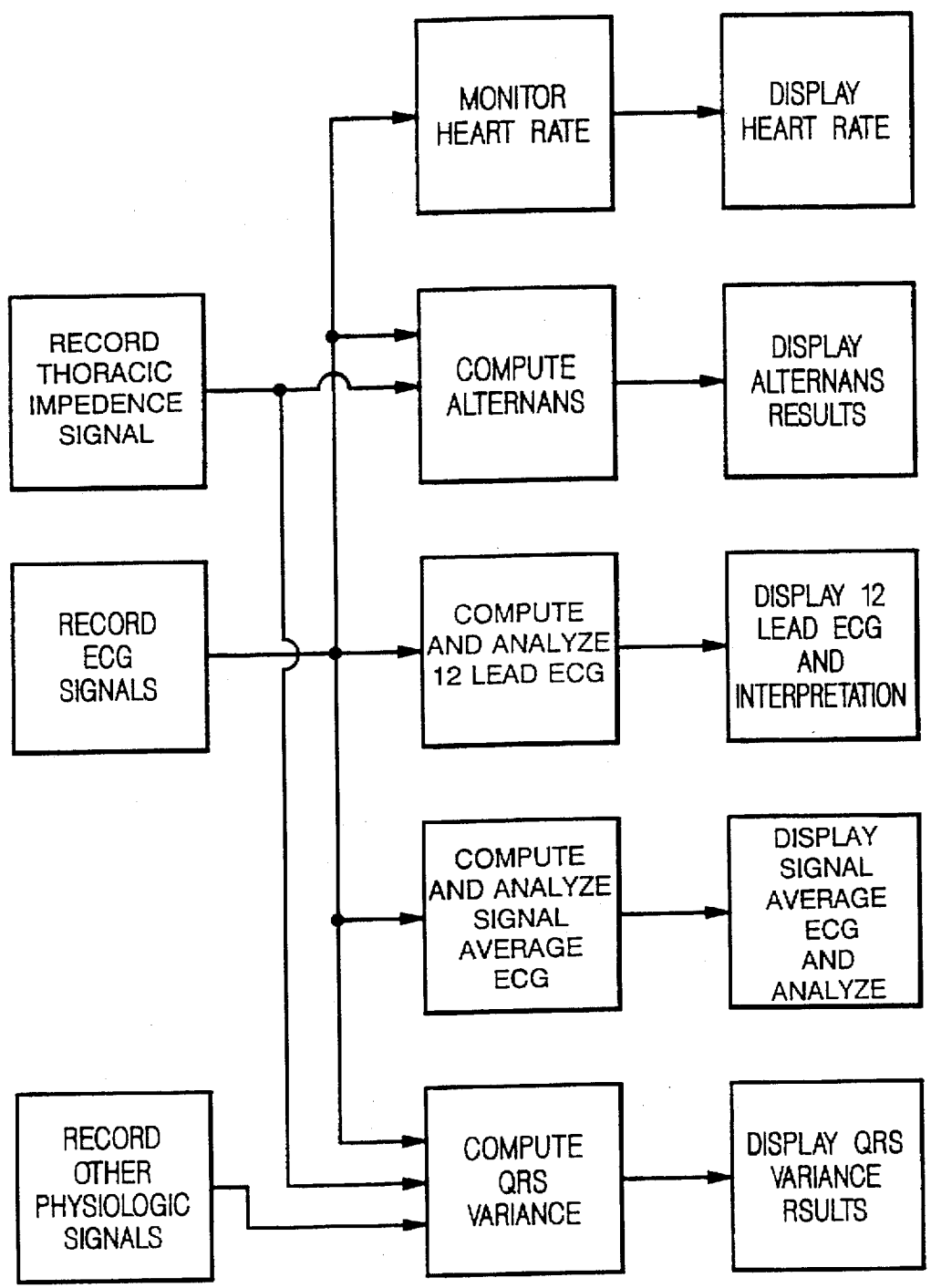
FIG. 39 is a block diagram of a combined ECG cart and an alternans system.

FIG. 39 is a block diagram figure of a combined ECG Cart and Alternans System. In this figure, ECG signals are recorded from body surface electrodes. From the ECG signals the heart rate is monitored. Also, an impedance signal may be measured from the ECG electrodes to monitor respiratory activity. The ECG signals are used to compute alternans in conjunction with the monitored heart rate and impedance signals according to the method of the invention taught above. The alternans measurements are computed and displayed. The ECG signals are used to compute and analyze the 12 lead ECG in any of the manners well known in the art and the 12 lead ECG and its interpretation is displayed. The ECG signals are used to compute and analyze the Signal Averaged ECG in any of the manners well known in the art and the Signal Averaged ECG and its analysis is displayed. The ECG signals are used to the QRS variance in any of the manners well known in the art and the QRS variance results are displayed. The ECG signals are used in conjunction with the impedance signal, the heart rate signal, and other physiologic signals such as non-invasively recorded arterial blood pressure to compute Physiologic System Identification results and the results are displayed.

D. Combination of An Alternans Test System with an Ambulatory ECG (Holter) System Another preferred embodiment, involves detection of alternans during naturally occurring physiologic stresses. This preferred embodiment involves recording physiologic signals and determining the presence of physiologic stress by means of a monitored physiologic variable such as heart rate. For example, electrodes may be applied and electrocardiographic signals may be recorded on a portable recorder known in the art as a Holter Monitor. The heart rate may be determined from analysis of the electrocardiographic signals. Periods of naturally occurring stress during the recording period, which may be 24 hours in duration, may be identified as the periods during which the heart rate exceeds some threshold value such as 90 beats per minute. Naturally occurring stresses may result from exercise, emotional stress, bowel movements, sexual activity and the like. The physiologic signals may be analyzed during the periods of naturally occurring stress for the presence of alternans.

One way of measuring cardiac ischemia is by measuring shifts in the ST segment of the electrocardiogram. The presence of myocardial ischemia may alter the interpretation of an alternans pattern of cycle-to-cycle variability in physiologic waveform morphology. For example, the presence of alternans in association with the development of myocardial ischemia may not necessarily indicate that the patient is at risk of ventricular arrhythmias when ischemia is not provoked by a similar stress. Therefore, combining the two systems has further advantages.

There are other advantages to combining an alternans measurement system with a Holter system. These systems are used to determine if a patient is experiencing ventricular or atrial arrhythmia's during a normal 24 hour period. They are often used for patients complaining of fainting spells where such fainting is suspected to be of cardiac origin. These same patients are candidates for alternans testing (the ventricular tachycardia predicted by alternans test being one possible cause of the fainting) and so a combined test is advantageous. Furthermore, the patient can be instructed to be active during the 24 hour period and thereby increase the chance that physiological stress will induce alternans.

One problem with such a combined system is that in a 24 hour period, there is a significant likelihood of finding some artifact occurring at 0.5 of the heart rate and therefore causing a false positive alternans result. As a result the noise measurement, epoch selection, noise reduction, statistical significance and other teachings of this patent become very important.

Figure 40:
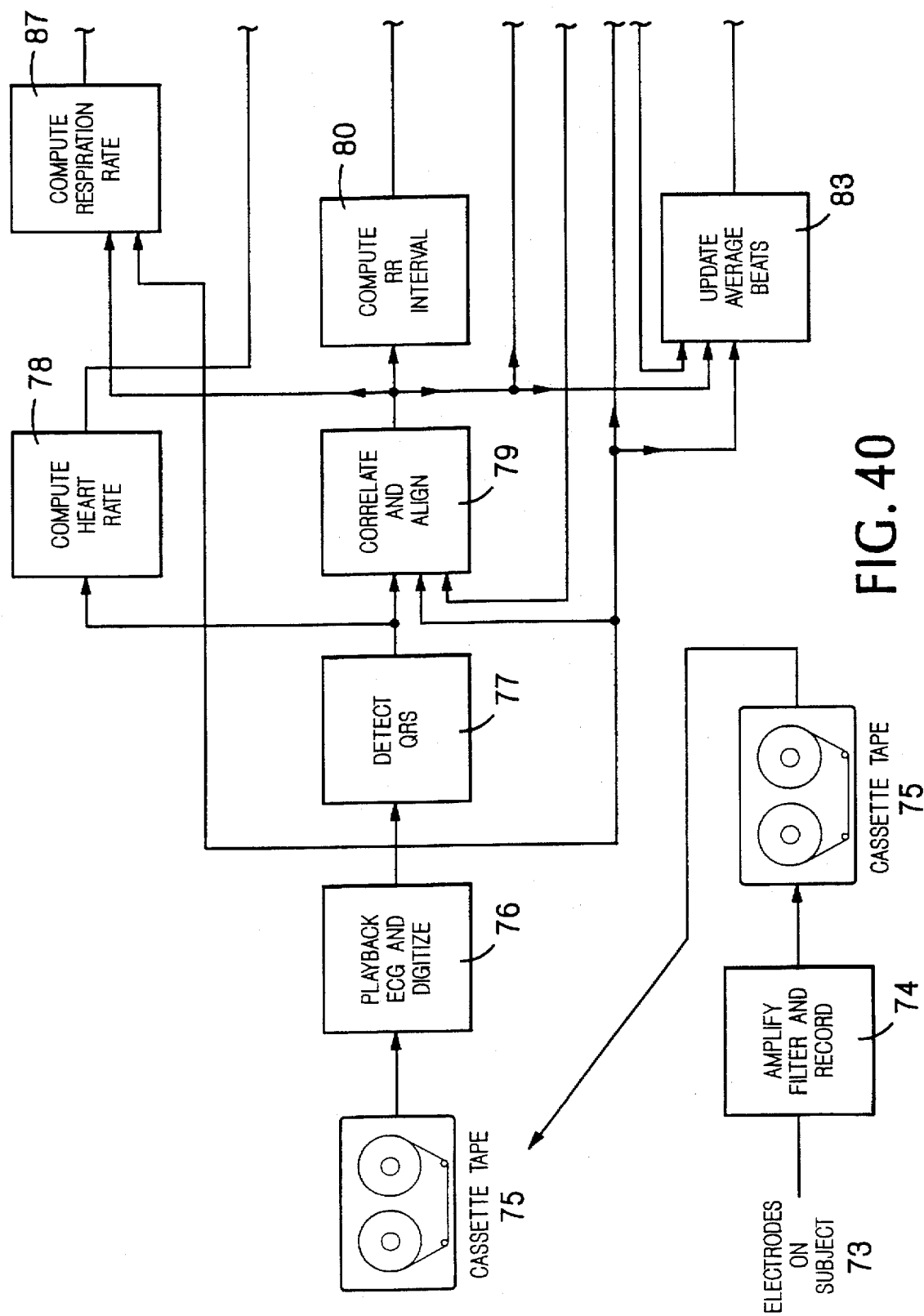
FIGS. 40 and 40A show a block diagram for a combined ambulatory (i.e., long term or Holter) ECG analysis and alternans system.
Figure 40A:
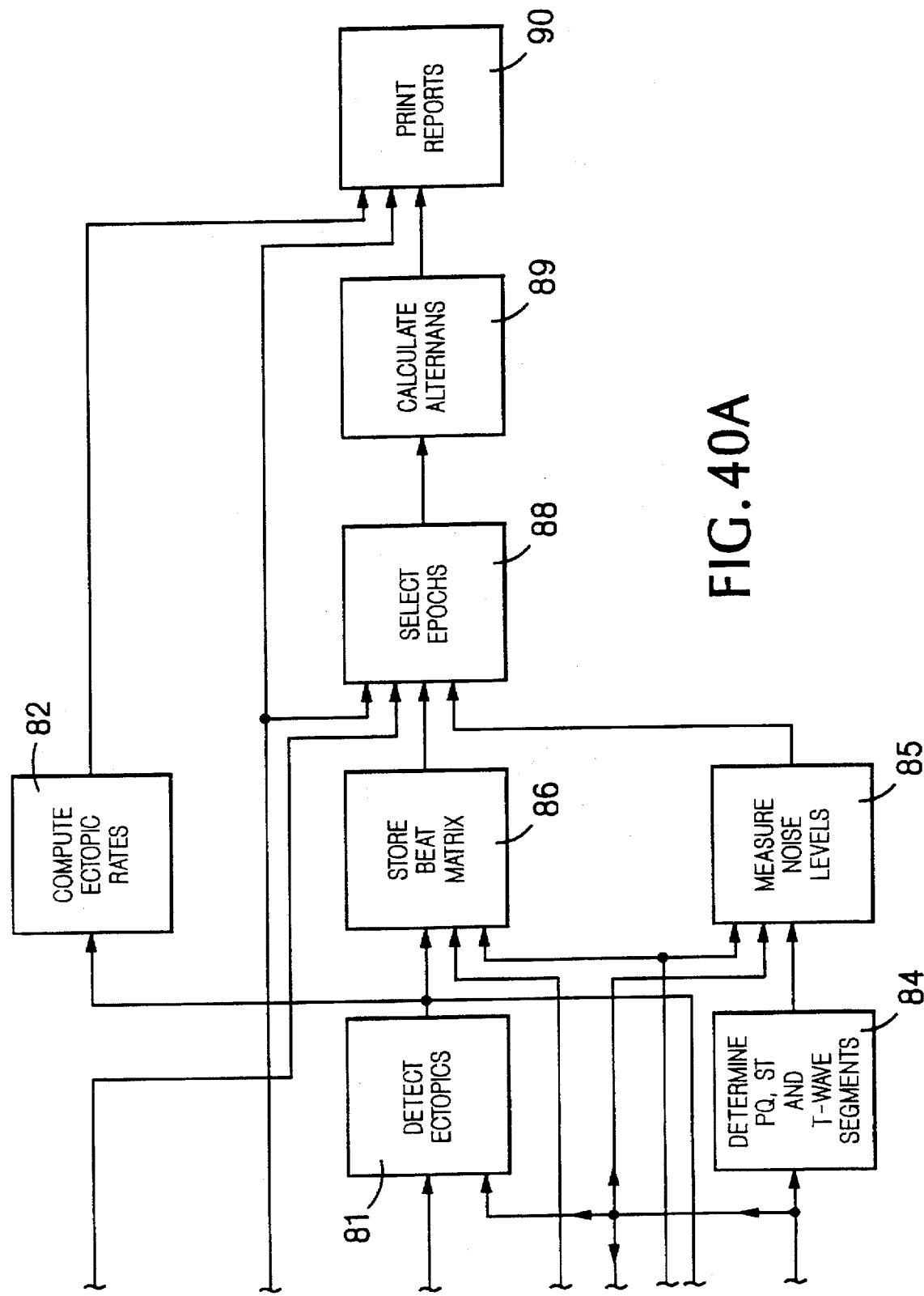

FIGS. 40 and 40A show the block diagram of a Combined Ambulatory ECG and Alternans system. The functional blocks are the same as those described for the combined stress test and alternans system described above unless otherwise stated. Electrodes 73 are placed on the subject, the ECG data is amplified and recorded 74 on a cassette tape 75 (alternate embodiments may use digital storage of the data and much of the processing described below may take place in the recording device instead of the playback system). The cassette tape is later played back and digitized 76 and QRS complexes are detected 77 and heart rate is computed 78. The QRS complexes are cross correlated with the average beat templates and aligned in 79, RR intervals are computed 80 and ectopic beats are detected 81. Rates of ectopics are computed 82 as well as the existence of specific rhythms such as runs of ectopics or ventricular tachycardia using techniques well known in the art and these data are included in printed reports 90.

Average beats are updated 83, the PQ, ST an T-wave segments are determined 84, noise levels are computed 85 and the beat matrix is stored 86 all as described above.

However, the strategy for respiration determination and correction is unlike that used in the combined alternans and the stress test system. Most ambulatory recorders do not include a channel for respiration and, although one embodiment would include a respiration channel and possibly epoch selection processing in the recording device, it is desirable to create an analysis system which will work with existing recorders and therefore not require a respiration channel. The preferred strategy therefore is to detect respiration rate from changes in the ECG and to eliminate from consideration epochs where the respiration rate is at an even submultiple of the heart rate. This is accomplished in 86 by measuring the amplitude changes of the QRS complex in one lead, or the orientation of the QRS vector in space with multiple leads, and determining the respiration frequency (for methods see "Clinical Validation of the ECG-Derived Respiration (EDR) Technique", by G. B. Moody et al, 1986, cited earlier). If the respiration rate is within a few percent of ¼ or ⅙ of the heart rate, then the epoch will not be selected for alternans analysis.

Another embodiment is to compute the FFT's for the alternans spectra as described previously, but then to reject any epochs or spectra which have peaks at ¼ or ⅙ of the heart rate. Another embodiment is to include the respiratory rate or other indication of respiratory peak in the output of the system in such a manner that the operator can reject any data from inappropriate epochs.

The system then selects epochs for analysis 88 in the manner described previously. However, since the rate of any rhythmic exercise is not controlled by the system, it is more important that any epochs with rhythmic artifact at even submultiples of the heart rate be rejected. The weight given to PQ segment or other noise at an even submultiple of the heart rate is therefore increased. Other embodiments which use recording devices designed for the alternans measurements can include multiple channels or specific measurements of artifact for such use. Finally, alternans is calculated 89 as described previously (without respiration correction), and the results printed in reports 90.

In another preferred embodiment, one records electrocardiographic signals over a long period of time, generally in excess of one hour and often 24 hours in duration. This recording generally may be obtained with a portable electrocardiographic recording device (often called a Holter monitor in the art). During the recording period the patient may experience a variety of physiologic stresses such as exercise, emotional stress, transient myocardial ischemia, sexual activity, and straining during bowel movements. In this preferred embodiment the alternans occurring during these episodes of spontaneous physiologic stress may be measured by analysis of the electrocardiographic waveforms. Such episodes may be identified for example by identifying periods during which the heart rate is elevated. It is also advantageous in this preferred embodiment to measure artifact, resulting for example from walking or running, which may interfere with the alternans measurement in the same manner as described above. This may be accomplished for example by measuring variability in a segment of the electrocardiographic waveform during which there is normally no cardiac electrical activity such as the PQ segment. Thus variability in the PQ segment may be attributed to noise not of cardiac origin. Alternatively, artifact can be measured from recordings made from electrodes located at positions on the body which are expected to result in little recorded cardiac activity. Alternatively a measure of rhythmic artifact may be obtained from an accelerometer worn by the patient. In all cases the data would be analyzed for the level of total artifact, and/or for the level of artifact occurring at or near the alternans frequency (i.e., half the heart rate), and/or for the level of artifact occurring at a submultiple of the alternans frequency (such as one quarter or one sixth the heart rate) where an harmonic of the artifact may interfere with the alternans measurement. Segments of data or measurements made during such data would be ignored or de-rated or the levels of potentially interfering artifact would be reported so that the clinician could consider such in interpreting the significance of the test result.

VIII. Other Embodiments

In one preferred embodiment, one applies a physiologic stress and then collects data for analysis of the temporal pattern of cycle-to-cycle variability in waveform morphology during and/or upon cessation of the stress. In this manner one avoids the problem of physiologic noise induced during the physiologic stress itself, but take advantage of the effect of the stress in augmenting a particular temporal pattern of cycle-to-cycle variability in physiologic waveforms. During physiologic stress tests used for the purpose of detecting coronary artery disease data are generally collected during the period following the cessation of the stress. Thus it is particularly convenient to collect such data in a stress test combined both for the purpose of detecting coronary artery disease and cycle-to-cycle variability in waveform morphology such as alternans.

In certain embodiments, the techniques described above may be used together with electrical pacing techniques (e.g., using electrodes placed in the patient's heart, using external body surface pacing, esophogeal pacing). For example, the patient's heart rate may be raised to a desired level (e.g., 90–150 beats per minute) and one or more of the signal processing techniques described above are used to measure the level of alternans. One or more of the assessment techniques described above are used to determine the patient's risk to cardiac electrical instability.

IX. Clinical Study

To test the methods of this invention including the use of physiological stress, noise reduction from multiple electrodes, epoch selection, noise measurement and rejection, and the use of multiple stages a clinical study was performed on 21 patients. Measurements of alternans using all of these techniques were made on 21 patients at rest, and during a bicycle exercise protocol designed to maintain the heart rate between 100–110 beats per minute. The results of this test were compared with the vulnerability to ventricular arrhythmias as define by a prior episode of sustained ventricular tachycardia or fibrillation or induction of sustained ventricular tachycardia or fibrillation during programmed electrophysiologic stimulation. The results (see FIG. 41) show that alternans measured at rest was not a statistically significant predictor of ventricular vulnerability, indicated by the fact that the p value was greater than 0.05. Measurements made during exercise were highly significant (p=0.005) with a sensitivity of 80% and specificity of 91%. Combined measurements made during rest and exercise were even a better predictor (p<0.005) with a sensitivity of 100% and specificity of 91%.

X. Conclusion

The various aspects of this invention make it possible for alternans to be used as a clinical predictor of ventricular arrhythmias under conditions of clinical practice. Each of the improvements discussed above may be applied individually and each substantially improves the ability to measure alternans in order to assess a patient's cardiac electrical stability. A novel and unexpected result of this invention is that alternans can be used as a non-invasive clinical tool to identify individuals at risk of ventricular arrhythmias.

Still other embodiments are within the scope of the claims.

What is claimed is:

1. A method for measuring alternans in at least one physiologic signal representative of activity of the heart of a patient, the physiologic signal including a sequence of substantially repeating physiologic waveforms, the method comprising the steps of:

altering a physiologic condition of a patient to stress the heart of the patient without applying pacing stimuli directly to the heart;

receiving a physiologic signal representative of activity of the stressed heart; and digitally processing the physiologic signal to determine a level of alternans in the signal.

2. The method of claim 1 wherein:

the physiologic condition of the patient is altered by naturally occurring stress during an extended period, and the step of receiving the physiologic signal comprises receiving the physiologic signal from a portable recording device.

3. The method of claim 1 wherein the physiologic condition of the patient is altered so that the patient's heart rate is above a predetermined rate.

4. The method of claim 3 wherein the physiologic condition of the patient is altered so that the patient's heart rate is between about 90 and about 150 beats per minute.

5. The method of claim 1 wherein said step of altering the physiologic condition of the patient comprises exercising the patient.

6. The method of claim 1 wherein the patient's heart is stressed by exercise.

7. The method of claim 6 wherein the patient exercises by pedalling a bicycle.

8. The method of claim 6 further comprising the step of producing a signal for controlling the patient's exercise intensity.

9. The method of claim 8 wherein the step of producing a signal for controlling the patient's exercise intensity includes adjusting the signal to control the patient's exercise intensity to achieve a desired heart rate in the patient.

10. The method of claim 6 further comprising the steps of receiving signals representative of the patient's rate of exercise and using the signals representative of the patient's rate of exercise in analyzing the physiologic signal.

11. The method of claim 6 further comprising the steps of producing a signal for controlling the patient's exercise and using the signal to control the patient's exercise.

12. The method of claim 11 wherein the signal for controlling the patient's exercise controls the patient's rate of exercise so as to reduce interference of noise related to the rate of exercise with determining the level of alternans.

13. The method of claim 11 wherein the controlling signal is adjusted to reduce noise that interferes with determining the level of alternans.

14. The method of claim 13 wherein the controlling signal is adjusted to reduce noise having a substantially repeating component that repeats at a frequency of about one half the patient's heart rate and noise having a substantially repeating component that repeats at a frequency of a submultiple of one half of the patient's heart rate.

15. The method of claim 11 wherein the controlling signal is produced to reduce noise generated by at least one source other than the patient's heart.

16. The method of claim 15 wherein the controlling signal is produced to reduce noise artifacts generated as a result of respiration of the patient.

17. The method of claim 11 wherein said controlling signal is produced based on a predetermined exercise protocol specifying target exercise rates.

18. The method of claim 6 wherein the patient exercises by walking on a treadmill.

19. The method of claim 6 wherein the patient exercises by stair stepping.

20. The method of claim 1 further comprising the steps of determining the patient's heart rate and using the determined heart rate in analzye the level of alternans in the physiologic signal.

21. The method of claim 20 further comprising the step of producing an output signal representative of the patient's heart rate.

22. The method of claim 1 further comprising the steps of assessing the patient's respiratory activity, producing an output signal representative of the patient's respiratory activity, and displaying the output signal to permit visual assessment of the level of alternans in the physiologic signal.

23. The method of claim 1 further comprising determining a frequency of a rhythmic artifact in the received physiologic signal and wherein the determination of the level of alternans is based on portions of the received physiologic signal corresponding to periods when the rhythmic artifact is at frequencies that do not interfere with the determination of the level of alternans.

24. The method of claim 23 wherein the patient's heart is stressed by exercise and the rhythmic artifact corresponds to the patient's rate of exercise.

25. The method of claim 1, further comprising the steps of determining the patient's respiratory rate and determining the patient's heart rate, wherein the determination of a level of alternans is based on portions of the received physiologic signal corresponding to periods when the patient's respiratory rate is not an even sub-multiple of the patient's heart rate.

26. The method of claim 1, further comprising the step of detecting abnormal beats in portions of the physiologic signal, wherein the level of alternans is determined by selecting portions of the received physiologic signal based on the presence of abnormal beats.

27. The method of claim 26 further comprising displaying a signal indicative of the presence of abnormal beats.

28. The method of claim 1 further comprising the steps of determining the patient's heart rate and simultaneously a signal representative of the determined level of alternans and producing a signal representative of the determined heart rate.

29. The method of claim 1 wherein the step of digitally processing the physiologic signal to determine a level of alternans comprises reducing the effect of noise by compensating for interfering variability in the morphology of the substantially repeating waveforms in the received signal.

30. The method of claim 29 wherein the step of compensating for interfering variability comprises compensating for intercycle interval variability.

31. The method of claim 29 wherein the step of compensating for interfering variability comprises compensating for variability generated by the patient's respiratory activity.

32. The method of claim 1 wherein said step of altering the physiologic condition of the patient comprises administering to the patient a pharmacological agent that stresses the heart of the patient.

33. The method of claim 32 wherein the pharmacological agent that is administered is a beta-sympathetic agent.

34. The method of claim 32 wherein the pharmacological agent that is administered is a parasympathetic blocking agent.

35. The method of claim 32 wherein the pharmacological agent that is administered is a vasodilator.

36. The method of claim 1 wherein said step of altering the physiologic condition of the patient comprises applying negative body pressure to the lower body of the patient.

37. The method of claim 1 wherein said step of altering the physiologic condition of the patient comprises altering the position of the patient's body to be different from a supine position.

38. The method of claim 37 further comprising the step of producing a signal representative of heart rate.

39. The method of claim 1 wherein the physiologic condition of the patient is altered spontaneously.

40. The method of claim 39, wherein the spontaneous alteration of the physiologic condition is a result of daily activity.

41. The method of claim 40, further comprising recording physiologic signals using a portable recording device, wherein the step of receiving a physiologic signal comprises receiving a physiologic signal recorded using the portable recording device.

42. The method of claim 41, further comprising determining the presence of spontaneous alteration of the physiologic condition by reference to a recorded physiologic signal.

43. The method of claim 42, further comprising determining a heart rate and determining the presence of spontaneous alteration of the physiologic condition by reference to the heart rate.

44. The method of claim 1 further comprising the step of processing the physiologic signal to determine whether the patient has coronary artery disease.

45. The method of claim 44 wherein coronary artery disease is determined by determining physiologic indices of ischemia in the patient.

46. The method of claim 22, wherein the signal related to the patient's respiratory rate indicates whether the respiratory rate is an even sub-multiple of the patient's heart rate.

47. The method of claim 1 further comprising the steps of:
obtaining a second signal from the patient;
determining a relationship between variability in the first and second received signals; and
using the relationship in the determination of a level of alternans.

48. The method of claim 47 wherein the step of determining a relationship comprises relating desired features of the first and second signals.

49. The method of claim 47 wherein the step of determining a relationship comprises relating noise components of the first and second signals.

50. The method of claim 47 wherein the step of using comprises combining the first and second signals to noise.

51. The method of claim 47 wherein the second obtained signal represents interbeat interval variability.

52. The method of claim 47 wherein said first and second signals are ECG signals measured from respective ECG leads.

53. The method of claim 47 further comprising the step of processing the first and second signals to determine a distortion metric, and wherein the first and second received signals are combined in a manner so that the distortion metric is minimized.

54. The method of claim 47 wherein the second signal is representative of noise.

55. The method of claim 54 wherein the second signal is representative of impedance.

56. The method of claim 54 wherein the second signal represents a measure of respiration.

57. The method of claim 1 further comprising the steps of:
receiving a second physiologic signal representative of activity of the patient's heart;
determining a relationship between desired features of the first and second received physiologic signals;
determining a relationship between noise components of the first and second received physiologic signals; and
combining the first and second received physiologic signals to reduce noise in the determination of a level of alternans.

58. The method of claim 57 wherein said first and second received signals are ECG signals measured from respective ECG leads, said first and second signals being combined in a manner preserving the orientation of the ECG leads in space.

59. The method of claim 58 further comprising the step of processing the first and second signals to determine a distortion metric, and wherein the first and second received signals are combined in a manner so that the distortion metric is below a prescribed level.

60. The method of claim 1 wherein the processing step further comprises basing the determination of the level of alternans on portions of the received physiologic signal that are less affected by interfering processes than other portions of the received physiologic signal.

61. The method of claim 60 wherein the processing step comprises basing the determination of the level of alternans on portions of the received physiologic signal that are less affected by abnormal beats than other portions of the received physiologic signal.

62. The method of claim 60 wherein the processing step further comprises basing the determination of level of alternans on portions of the received physiologic signal that are less affected by noise due to respiration than other portions of the received signal.

63. The method of claim 1 further comprising the steps of detecting abnormal waveforms in the physiologic signal; independently estimating the level of alternans based on sequences of data between abnormal waveforms; and combining the independent estimations to determine the measure of the level of alternans.

64. The method of claim 1 wherein the step of digitally processing the physiologic signal to determine a level of alternans comprises relying on a predetermined assumption that a particular abnormal waveform is followed by a normal waveform of a given phase.

65. The method of claim 64 further comprising using the predetermined assumption to adjust a phase relationship between normal waveforms that precede the abnormal waveform and normal waveforms that follow the normal waveform.

66. The method or claim 65 further comprising using the predetermined assumption to determine whether to delete the abnormal waveform or replace the abnormal waveform with a computed waveform in the determination of the level of alternans.

67. The method of claim 1 further comprising measuring ECG signals from one or more transducers placed on the patient, determining a respiratory rate of the patient by analysis of the measured ECG signals, and displaying the respiratory rate to permit visual assessment of the level of alternans in the signal.

68. The method of claim 67 wherein analysis of said ECG signals comprises analyzing the amplitude or vectorcardiographic angle of the features of the measured ECG signals.

69. The method of claim 1, further comprising:
displaying the determined level of alternans as an alternans measure;
generating a reference signal that corresponds to reliability of the alternans measure; and
displaying the reference signal with the alternans measure in a way that permits visual evaluation of the alternans measure in view of characteristics of the reference signal.

70. The method of claim 69, wherein the step of displaying the reference signal further comprises graphically displaying the reference signal with the alternans measure.

71. The method of claim 70, wherein the step of displaying the reference signal comprises displaying the reference signal and the alternans measure using a common time axis.

72. The method of claim 69, wherein the reference signal is indicative of a parameter that affects reliability of the alternans measure, the method further comprising:
generating a second reference signal that corresponds to reliability of the alternans measure and is indicative of a second parameter that affects reliability of the alternans measure; and
displaying the alternans measure and the first and second reference signals in a way that permits visual evaluation of the alternans measure in view of characteristics of the reference signals.

73. The method of claim 69, wherein the reference signal comprises a measure of the patient's heart rate.

74. The method of claim 69, wherein the reference signal comprises a measure of defects in the physiologic signal.

75. The method of claim 74, wherein the physiologic signal comprises a sequence of ECG beats and wherein the reference signal comprises a measure of a number of ectopic beats in the sequence.

76. The method of claim 74, wherein the physiologic signal comprises a sequence of ECG beats and wherein the reference signal comprises a measure of a rate of ectopic beats in the sequence.

77. The method of claim 69, wherein the reference signal comprises a measure of noise in the physiologic signal.

78. The method of claim 77, wherein the reference signal comprises a measure of noise in a frequency band of the physiologic signal.

79. The method of claim 78, wherein the frequency band is related to the patient's heart rate at different times.

80. The method of claim 77, wherein the reference signal comprises a measure of relative amplitudes of a level of noise in the physiologic signal and of the physiologic signal.

81. The method of claim 69, wherein the reference signal comprises a measure of the patient's respiratory activity.

82. The method of claim 69, wherein the reference signal comprises a measure of exercise by the patient.

83. The method of claim 69, wherein the step of displaying the alternans measure comprises displaying the alternans measure on a video monitor.

84. The method of claim 69, wherein the step of displaying the alternans measure comprises printing the alternans measure.

85. The method of claim 84, wherein the step of displaying the alternans measure comprises printing the alternans measure using a chart recorder.

86. The method of claim 1 further comprising producing an output signal representative of a rhythmic artifact in the received physiologic signal.

87. The method of claim 86 wherein the determination of the level of alternans is based on portions of the received physiologic signal corresponding to portions of the output signal that meet predetermined criteria.

88. The method of claim 1 further comprising displaying a signal indicative of the presence of abnormal beats.

89. The method of claim 1, wherein the step of receiving a physiologic signal representative of activity of the heart of the patient comprises receiving the physiologic signal using a multi-segment electrode having multiple electrode segments defined on a common basepad.

90. A method for measuring alternans in at least one physiologic signal representative of activity of the heart of a patient, the physiologic signal including a sequence of substantially repeating physiologic waveforms, the method comprising the steps of:
receiving a physiologic signal representative of activity of the heart of the patient;
digitally processing the physiologic signal to determine a level of alternans in the physiologic signal; and
producing a control signal for controlling a physiologic condition of the patient in a manner such that the effects on the physiologic signal of interfering noise sources is reduced.

91. The method of claim 90 wherein the control signal is produced to control the respiratory rate of the patient.

92. The method of claim 90, wherein the step of receiving a physiologic signal representative of activity of the heart of the patient comprises receiving the physiologic signal using a multi-segment electrode having multiple electrode segments defined on a common basepad.

93. A method for measuring alternans in at least one physiologic signal representative of activity of the heart of a patient, the physiologic signal including a sequence of substantially repeating physiologic waveforms, the method comprising the steps of:
altering a physiologic condition of the patient to stress the heart of the patient without applying pacing stimuli directly to the heart to achieve a heart rate above a predetermined rate;
receiving a physiologic signal representative of activity of the stressed heart of the patient; and
digitally processing the physiologic signal to determine a level of alternans in the signal.

94. The method of claim 93 wherein the physiologic condition of the patient is altered so that the patient's heart rate is between about 90 and about 150 beats per minute.

95. The method of claim 93 further comprising the steps of determining the patient's heart rate, and simultaneously producing a signal representative of the determined level of alternans and producing a signal representative of the determined heart rate.

96. The method of claim 93, wherein the step of receiving a physiologic signal representative of activity of the heart of the patient comprises receiving the physiologic signal using a multi-segment electrode having multiple electrode segments defined on a common basepad.

97. A method for measuring alternans in at least one physiologic signal representative of activity of the heart of a patient, the physiologic signal including a sequence of substantially repeating physiologic waveforms, the method comprising the steps of:
receiving a physiologic signal representative of activity of the heart of the patient; and
digitally processing the physiologic signal to determine a level of alternans in the signal, wherein the processing step comprises processing the signal to reduce the effect of noise signals having a frequency at about half of the patient's heart rate and noise signals having a frequency at about a submultiple of half of the patient's heart rate.

98. The method of claim 97 wherein the processing step comprises adaptively removing noise signals before a level of alternans is determined.

99. The method of claim 97 wherein the step of processing the signal to reduce the effect of noise signals comprises basing the determination of a level of alternans on portions of the received signal corresponding to periods when the patient's heart rate is above a predetermined level.

100. The method of claim 97 wherein the step of processing the signal to reduce the effect of noise signals comprises basing the determination of a level of alternans on portions of the received signal corresponding to periods when the patient's respiratory rate is different from the patient's heart rate and is different from sub-multiples of the patient's heart rate.

101. The method of claim 97 wherein the processing step further comprises basing the determination of a level of alternans on portions of the received physiologic signal that are less affected by interfering processes than other portions of the received physiologic signal.

102. The method of claim 97 wherein the processing step comprises compensating for interfering variability in the morphology of the substantially repeating waveforms in the received signal.

103. The method of claim 102 wherein the interfering variability is generated by the patient's respiratory activity.

104. The method of claim 102 wherein the interfering variability that is compensated is intercycle interval variability.

105. The method of claim 104 wherein the step of reducing the effect of intercycle interval variability comprises determining a relationship between the variation in intercycle intervals and changes in waveform morphology.

106. The method of claim 105 wherein the step of determining a relationship is performed by a filter relating measurements of a given waveform to the sequence of preceding intercycle intervals.

107. The method of claim 97 wherein the processing step comprises relating the variability in a noise signal to the variability in the morphology of the substantially repeating waveforms.

108. The method of claim 107 wherein the noise signal represents a measure of the respiratory activity of the patient.

109. The method of claim 97, wherein the step of receiving a physiologic signal representative of activity of the heart of the patient comprises receiving the physiologic signal using a multi-segment electrode having multiple electrode segments defined on a common basepad.

110. A method for measuring alternans in at least one physiologic signal representative of activity of the heart of a patient, the physiologic signal including a sequence of substantially repeating physiologic waveforms, the method comprising the steps of:
receiving a physiologic signal representative of activity of the heart of the patient;
digitally processing the physiologic signal to determine a level of alternans in the signal, wherein the processing step comprises characterizing at least one portion of the received signal based on at least one preselected criterion selected from a group consisting of the patient's heart rate, the patient's respiration rate, or the presence of abnormal beats in the received signal, and using the characterization of the at least one portion of the received signal to determine a level of alternans in the signal.

111. The method of claim 110 wherein the characterizing step comprises selecting portions of the received signal to include in the determination of alternans step.

112. The method of claim 111, further comprising the step of determining the patient's heart rate, wherein the selecting step comprises selecting portions of the received signal corresponding to periods when the patient's heart rate satisfies a predetermined criterion.

113. The method of claim 111, further comprising determining the patient's respiratory activity, wherein the selecting step comprises selecting portions of the received signal corresponding to periods when the patient's respiratory activity meets a predetermined criterion.

114. The method of claim 111 wherein the selecting step comprises selecting portions of the received signal corresponding to periods when the presence of abnormal beats meet a predetermined criterion.

115. The method of claim 110 wherein the at least one preselected criterion comprises the patient's heart rate.

116. The method of claim 115 wherein measured signals are removed from consideration when corresponding to periods when an interfering noise signal varies at a multiple or submultiple of the patient's heart rate.

117. The method of claim 110 wherein said at least one preselected criterion comprises the patient's respiration rate.

118. The method of claim 110 wherein said at least one preselected criterion comprises the presence of abnormal beats in the received signal.

119. The method of claim 110, wherein the step of receiving a physiologic signal representative of activity of the heart of the patient comprises receiving the physiologic signal using a multi-segment electrode having multiple electrode segments defined on a common basepad.

120. The method of claim 110 wherein the characterizing step comprises selecting portions of the received signal that are less affected by interfering processes than other portions of the received physiologic signal.

121. A real-time method for measuring alternans in at least one physiologic signal representative of activity of the heart of a patient, the physiologic signal including a sequence of substantially repeating physiologic waveforms, the method comprising the steps of:
   receiving a physiologic signal representative of activity of the heart of the patient;
   digitally processing the physiologic signal to determine a level of alternans in the signal; and
   concurrently with the processing step, providing an output representative of the level of alternans as the level of alternans is determined.

122. The method of claim 121 wherein, after a predetermined number of the substantially repeating waveforms are received to form a segment of data, the data segment is processed to determine a level of alternans, the determined level of alternans is provided, and the steps of receiving, processing, and providing are repeated.

123. The method of claim 122 further comprising the steps of:
   using a preselected criterion for assessment of the condition of the patient's heart to determine when the receiving, processing and providing steps have been performed a sufficient number of times to permit accurate assessment of the condition of the patient's heart; and
   terminating the steps of receiving, processing, providing, and repeating when the receiving, processing and providing steps have been determined to have been performed for the sufficient number of times.

124. The method of claim 121, wherein the step of receiving a physiologic signal representative of activity of the heart of the patient comprises receiving the physiologic signal using a multi-segment electrode having multiple electrode segments defined on a common basepad.

125. A method for measuring alternans in at least one physiologic signal representative of activity of the heart of a patient, the physiologic signal including a sequence of substantially repeating physiologic waveforms, the method comprising the steps of:
   receiving a physiologic signal representative of activity of the heart of the patient;
   digitally processing the received physiologic signal to determine a level of alternans and to determine a level of noise; and
   using the determined level of noise to determine with a predetermined level of statistical certainty whether the alternans level is above a threshold.

126. The method of claim 125 wherein the using step comprises comparing the level of alternans against a first predetermined threshold and comparing the ratio of the alternans level to the noise level against a second predetermined threshold.

127. The method of claim 126 wherein the level of alternans is determined from a first portion of a measured substantially repeating waveform and the level of noise is determined from a different portion of the same waveform.

128. The method of claim 127 wherein the received signal is an ECG signal and the level of noise is determined from the PQ segment.

129. The method of claim 125 wherein said step of comparing comprises comparing the level of alternans in one portion of a measured substantially repeating waveform to a measure of noise in a different frequency band of the same waveform.

130. The method of claim 125 further comprising the steps of:
   determining the level in an alternating component in the received signal and determining the standard deviation of the energy of noise in the signal; and
   determining that the patient is at risk for cardiac instability if the level in the alternating component is greater than a predetermined threshold by one or more standard deviations of the noise level.

131. The method of claim 125 further comprising the steps of comparing the determined noise level against a predetermined threshold, and determining that the assessment of the patient's risk for cardiac instability is indeterminate if said noise level is greater than predetermined threshold.

132. The method of claim 125, wherein the step of receiving a physiologic signal representative of activity of the heart of the patient comprises receiving the physiologic signal using a multi-segment electrode having multiple electrode segments defined on a common basepad.

133. An apparatus for measuring an alternans pattern of cycle-to-cycle morphology variations in a sequence of substantially repeating physiologic waveforms in at least one signal measured from a patient, said apparatus comprising:
   one or more transducers for respectively measuring one or more signals from a patient, at least one of said one or more transducers being configured to measure a signal from the heart of the patient;
   a processor configured to obtain, from said one or more measured signals, a measure of the level of alternans in said signal from the heart of the patient for assessing the condition of the patient's heart; and
   a controller for producing signals to control a stressing device configured to alter a physiologic condition of the patient to stress the heart of the patient and thereby affect the signal from the heart of the patient, the controller producing the signals in response to a signal from the processor.

134. The apparatus of claim 133 wherein said processor determines indices of ischemia from said one or measured signals.

135. The apparatus of claim 133, further comprising an exerciser for controllably exercising the patient under control of the signals produced by said controller.

136. The apparatus of claim 133 wherein said stressing device comprises a device configured to administer a pharmacological agent that controllably alters the heart rate of the patient.

137. The apparatus of claim 133 wherein at least one of said one or more transducers comprises a multi-segment electrode having multiple separate surfaces for achieving electrical contact with a region on the surface of the patient.

138. The apparatus of claim 137 further comprising circuitry coupled to said one or more transducers to measure a signal representative of the respiratory pattern of the patient.

139. The apparatus of claim 137 further comprising circuitry coupled to said multi-segment electrode to measure a signal representative of the electrical impedance between said multi-segment electrode and the patient.

140. The apparatus of claim 133, wherein at least one of said one or more transducers comprises a multi-segment electrode having multiple electrode segments defined on a common basepad.

141. An apparatus for measuring an alternans pattern of cycle-to-cycle morphology variations in a sequence of substantially repeating physiologic waveforms in at least one signal measured from a patient, said apparatus comprising:

one or more transducers for respectively measuring one or more signals from a patient, at least one of said one or more transducers being configured to be coupled to the patient to measure a cardiac signal comprising a sequence of substantially repeating waveforms representative of one or more signals from the heart of the patient, said one or more transducers being configured to remain coupled to the patient for a period in excess of about one hour;

a recorder coupled to said one or more transducers and configured to store signals, including the cardiac signal, measured by said one or more transducers for a period in excess of one hour, the recorder comprising a portable recorder sized and configured to be carried by the patient as the patient engages in normal activities; and a processor configured to characterize portions of said stored signals corresponding to one or more periods according to one or more preselected criteria, and further configured to obtain from said characterized portions of said stored signals a measure of the level of alternans in the cardiac signal for assessing the condition of the patient's heart.

142. The apparatus of claim 141, wherein the processor is configured to generate output signals comprising a signal representative of noise and a signal representative of the determined level of alternans.

143. The apparatus of claim 142 wherein the processor is configured to generate an output signal representative of the patient's heart rate.

144. The apparatus of claim 141, wherein at least one of said one or more transducers comprises a multi-segment electrode having multiple electrode segments defined on a common basepad.

145. An apparatus for measuring an alternans pattern of cycle-to-cycle morphology variations in a sequence of substantially repeating physiologic waveforms in at least one signal measured from a patient, said apparatus comprising:

one or more transducers for respectively measuring one or more signals from a patient, at least one of said one or more transducers being configured to be coupled to the patient to measure a cardiac signal comprising a sequence of substantially repeating waveforms representative of one or more signals from the heart of the patient;

a heart rate monitor coupled to at least one of said one or more transducers to measure the heart rate of the patient from signals measured by said at least one transducer; and a processor configured to obtain, from said one or more measured signals and from said measured heart rate, a measure of the level of alternans in said cardiac signal for assessing the condition of the patient's heart.

146. The apparatus of claim 145, wherein at least one of said one or more transducers comprises a multi-segment electrode having multiple electrode segments defined on a common basepad.

147. A method for measuring a pattern of cycle-to-cycle morphology variations in a sequence of substantially repeating physiologic waveforms in at least one signal measured from a patient, said method comprising the steps of:

measuring one or more signals from a patient, at least one of said one or more signals comprising a cardiac signal including a sequence of substantially repeating waveforms representative of one or more signals from the heart of the patient;

processing said one or more measured signals to obtain a measure of the level of alternans in said one or more measured signals for assessing the condition of a patient's heart; and enhancing the measurement of the pattern of cycle-to-cycle morphology variations by reducing the effect of variability in the interval between adjacent waveforms in said cardiac signal.

148. The method of claim 147, wherein the step of measuring one or more signals comprises measuring at least one signal using a multi-segment electrode having multiple electrode segments defined on a common basepad.

149. A method for measuring an alternans pattern of cycle-to-cycle morphology variations in a sequence of substantially repeating waveforms in at least one signal measured from a patient, comprising the steps of:

measuring one or more signals from a patient, at least one of said one or more signals comprising a sequence of substantially repeating waveforms representative of one or more signals from the heart of the patient;

processing the one or more signals to compute a measure of alternans in the repeating waveforms;

additionally processing the one or more signals to produce an additional diagnostic from the group consisting of a signal averaged electrocardiogram and an analysis of QRS complex variability.

150. The method of claim 149, wherein the step of measuring one or more signals comprises measuring at least one signal using a multi-segment electrode having multiple electrode segments defined on a common basepad.

151. An apparatus for measuring an alternans pattern of cycle-to-cycle morphology variations in a sequence of substantially repeating waveforms in at least one signal measured from a patient, said apparatus comprising:

one or more transducers for respectively measuring one or more signals from a patient, at least one of said one or more transducers being coupled to the patient to measure at least one signal comprising a sequence of substantially repeating waveforms representative of one or more signals form the heart of the patient;

a processor configured to process the signals to produce a diagnostic corresponding to alternans and an additional diagnostic from the group consisting of a signal averaged electrocardiogram and an analysis of QRS complex variability.

152. The apparatus of claim 151, wherein at least one of said one or more transducers comprises a multi-segment electrode having multiple electrode segments defined on a common basepad.

* * * * *

UNITED STATES PATENT AND TRADEMARK OFFICE
CERTIFICATE OF CORRECTION

PATENT NO. : 5,713,367
DATED : February 3, 1998
INVENTOR(S) : Jeffrey M. Arnold, Paul Albrecht, Kevin S. Librett, and Richard J. Cohen It is certified that error appears in the above-identified patent and that said Letters Patent is hereby corrected as shown below:

Title page,
Item [56] References Cited, U.S. PATENT DOCUMENTS, "DeFault" reference should be -- DuFault --.
FIG. 39, Sheet 38 of 41, "IMPEDENCE" should be -- IMPEDANCE --.

Column 3,
Line 2, "re" should be -- are --.
Line 46, after "The", delete "the --.

Column 4,
Line 12, "gernal" should be -- general --.

Column 6,
Line 49, "invetion" should be -- invention --.
Line 58, "form" should be -- from --.

Column 11,
Line 38, "beat" should be -- beats --.
Lines 58 and 61, "does" should be -- dose --.

Column 16,
Line 25, insert a period at the end of the sentence.

Column 17,
Line 1, "determined" should be -- determine --.
Line 29, "theses" should be -- these --.
Line 64, "abnoraml" should be -- abnormal --.

Column 18,
Line 1, after "$A_8$" insert -- A --.

Column 22,
Line 62, "cause" should be -- caused --.

UNITED STATES PATENT AND TRADEMARK OFFICE
CERTIFICATE OF CORRECTION

PATENT NO.   : 5,713,367
DATED        : February 3, 1998
INVENTOR(S)  : Jeffrey M. Arnold, Paul Albrecht, Kevin S. Librett, and Richard J. Cohen It is certified that error appears in the above-identified patent and that said Letters Patent is hereby corrected as shown below:

Column 23,
Line 44, "belive" should be -- believe --.

Column 24,
Line 1, delete "as".
Line 23, "cause" should be -- caused --.
Line 62, "results" should be -- result --.
Line 63, "patterns" should be -- pattern --.
Line 65, "Beat" should be -- Beats --.

Column 25,
Line 13, before "contain", insert -- to --.
Line 39, "form" should be -- from --.
Line 49, after "503" delete "the".

Column 26,
Line 12, after "to", delete "the".
Line 63, after "used", delete "the".

Column 29,
"2μRMS" should be -- 2μV RMS --.

Column 32,
Line 50, after "may", insert -- be --, and after "from", delete "to".

Column 33,
Line 31, "a" should be -- an --.

Column 39,
Line 65, "an" should be -- and --.

Column 43,
Line 10, "analyze" should be -- analyzing --.

UNITED STATES PATENT AND TRADEMARK OFFICE
CERTIFICATE OF CORRECTION

PATENT NO.   : 5,713,367
DATED        : February 3, 1998
INVENTOR(S)  : Jeffrey M. Arnold, Paul Albrecht, Kevin S. Librett, and Richard J. Cohen It is certified that error appears in the above-identified patent and that said Letters Patent is hereby corrected as shown below:

<u>Column 44,</u>
Line 51, after "to", insert -- reduce --.

<u>Column 45,</u>
Line 34, after "received", insert -- physiologic --.

<u>Column 53,</u>
Line 6, "form" should be -- from --

Signed and Sealed this

Eleventh Day of September, 2001

*Attest:*

*Nicholas P. Godici*

*Attesting Officer*

NICHOLAS P. GODICI
*Acting Director of the United States Patent and Trademark Office*